(12) United States Patent
Belval et al.

(10) Patent No.: US 10,501,501 B2
(45) Date of Patent: Dec. 10, 2019

(54) NEPOVIRUS COAT PROTEIN FUSION POLYPEPTIDES AND THEIR USE

(71) Applicants: INSTITUT NATIONAL DE LA RECHERCHE AGRONOMIQUE, Paris (FR); UNIVERSITE DE STRASBOURG, Strasbourg (FR); CENTRE NATIONAL DE LA RECHERCHE SCIENTIFIQUE, Paris (FR)

(72) Inventors: Lorene Belval, Colmar (FR); Gerard Demangeat, Ostheim (FR); Caroline Hemmer, Colmar (FR); Christophe Ritzenthaler, Selestat (FR)

(73) Assignees: CENTRE NATIONAL DE LA RECHERCHE SCIENTIFIQUE, Paris (FR); UNIVERSITE DE STRASBOURG, Strasbourg (FR); INSTITUT NATIONAL DE LA RECHERCHE AGRONOMIQUE, Paris (FR)

( * ) Notice: Subject to any disclaimer, the term of this patent is extended or adjusted under 35 U.S.C. 154(b) by 0 days.

(21) Appl. No.: 15/758,732

(22) PCT Filed: Sep. 9, 2016

(86) PCT No.: PCT/EP2016/071364
§ 371 (c)(1),
(2) Date: Mar. 9, 2018

(87) PCT Pub. No.: WO2017/042367
PCT Pub. Date: Mar. 16, 2017

(65) Prior Publication Data
US 2018/0265552 A1  Sep. 20, 2018

(30) Foreign Application Priority Data

Sep. 11, 2015  (EP) .................................. 15306396

(51) Int. Cl.
*C07K 16/00* (2006.01)
*C07K 14/005* (2006.01)
*C12N 7/00* (2006.01)

(52) U.S. Cl.
CPC ............ *C07K 14/005* (2013.01); *C07K 16/00* (2013.01); *C12N 7/00* (2013.01);
(Continued)

(58) Field of Classification Search
None
See application file for complete search history.

(56) References Cited

U.S. PATENT DOCUMENTS

2004/0076611 A1* 4/2004 Bachmann ............ A61K 39/00
424/93.2
2010/0292089 A1* 11/2010 Bachmann ............ C07K 16/00
506/9

FOREIGN PATENT DOCUMENTS

WO  WO 2008/058396  5/2008
WO  WO 2010/146359  12/2010
(Continued)

OTHER PUBLICATIONS

NP_619706 Grapevine fanleaf virus, 2018 (Year: 2018).*
(Continued)

*Primary Examiner* — Michelle S Horning
(74) *Attorney, Agent, or Firm* — Saliwanchik, Lloyd & Eisenschenk

(57) ABSTRACT

The present invention relates to novel fusion polypeptides and the uses thereof. The invention particularly relates to conjugated coat proteins derived from nepoviruses, virus-like particles made with such proteins, and the uses thereof. The particles of the invention can expose and/or encage molecules of interest and have utility in various fields such as the pharmaceutical, agro, or veterinary areas.

Figure 1:
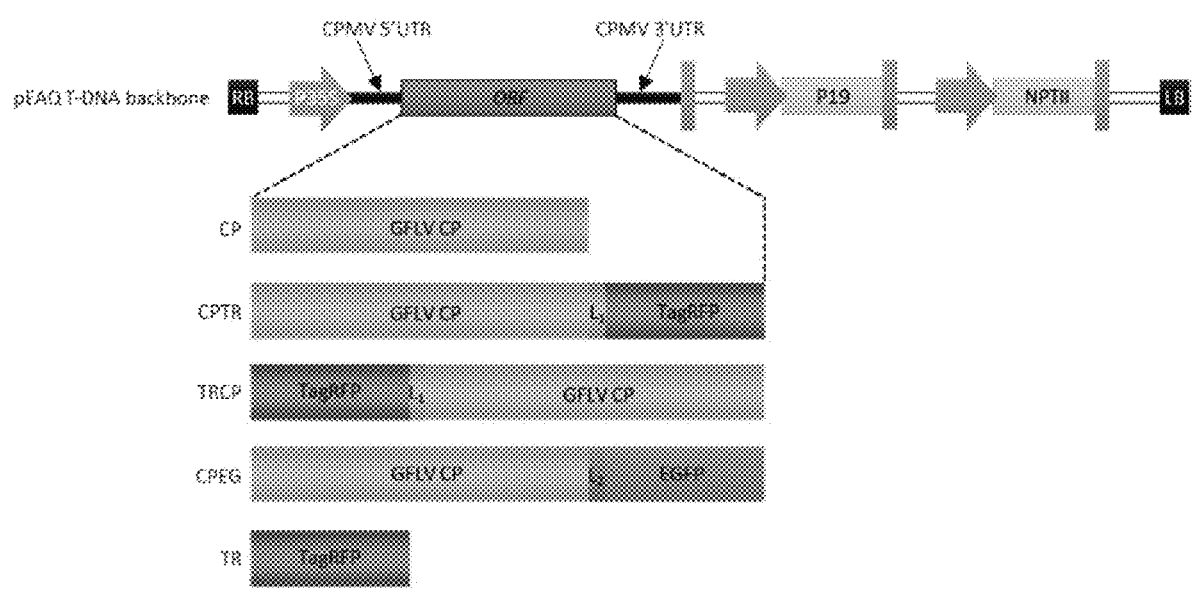

19 Claims, 10 Drawing Sheets
(Continued)

(7 of 10 Drawing Sheet(s) Filed in Color)

Specification includes a Sequence Listing.

(52) U.S. Cl.
CPC .... *C07K 2317/569* (2013.01); *C07K 2319/00* (2013.01); *C07K 2319/60* (2013.01); *C12N 2770/18022* (2013.01); *C12N 2770/18023* (2013.01)

(56) References Cited

FOREIGN PATENT DOCUMENTS

| | | | |
|---|---|---|---|
| WO | WO 2015/110601 | 7/2015 | |
| WO | WO-2018167070 A1 * | 9/2018 | ............. C07K 16/10 |

OTHER PUBLICATIONS

Schellenberger et al. Structural Insights into Viral Determinants of Nematode Mediated Grapevine fanleaf virus Transmission. PLoS Pathog. May 2011;7(5): p. 1-14. (Year: 2011).*

Belin, C. et al. "The nine C-terminal residues of the grapevine fanleaf nepovirus movement protein are critical for systemic virus spread" *Journal of General Virology*, Jun. 1, 1999, pp. 1347-1356, vol. 80, No. 6.

Bertioli, D. J. et al. "Transgenic plants and insect cells expressing the coat protein of arabis mosaic virus produce empty virus-like particles" *Journal of General Virology*, Aug. 1, 1991, pp. 1801-1809, vol. 72, No. 8.

Denis, J. et al. "Immunogenicity of papaya mosaic virus-like particles fused to a hepatitis C virus epitope: Evidence for the critical function of multimerization" *Virology*, May 5, 2007, pp. 59-68, vol. 363, No. 1.

Saunders, K. et al. "Efficient generation of cowpea mosaic virus empty virus-like particles by the proteolytic processing of precursors in insect cells and plants" *Virology*, Oct. 25, 2009, pp. 329-337, vol. 393, No. 2.

Singh, S. et al. "Expression of Tobacco Ringspot Virus Capsid Protein and Satellite RNA in Insect Cells and Three-Dimensional Structure of Tobacco Ringspot Virus-like Particles" *Virology*, Nov. 1, 1995, pp. 472-481, vol. 213, No. 2.

Written Opinion in International Application No. PCT/EP2016/071364, dated Nov. 15, 2016, pp. 1-6.

Spielmann, A. et al. "Analysis of transgenic grapevine (*Vitis rupestris*) and *Nicotiana benthamiana* plants expressing an *Arabis mosaic virus* coat protein gene" *Plant Science*, 2000, pp. 235-244, vol. 156.

* cited by examiner

NEPOVIRUS COAT PROTEIN FUSION POLYPEPTIDES AND THEIR USE

CROSS-REFERENCE TO RELATED APPLICATION

This application is the U.S. national stage application of International Patent Application No. PCT/EP2016/071364, filed Sep. 9, 2016.

The Sequence Listing for this application is labeled "Seq-List.txt" which was created on Feb. 22, 2018 and is 81 KB. The entire content of the sequence listing is incorporated herein by reference in its entirety.

The present invention relates to novel fusion polypeptides and the uses thereof. The invention particularly relates to conjugated coat proteins derived from nepoviruses, virus-like particles made with such proteins, and the uses thereof. The particles of the invention can expose and/or encage molecules of interest and have utility in various fields such as the pharmaceutical, agro, or veterinary areas.

BACKGROUND

The use of virus-like particles ("VLPs") made from virus capsid-derived proteins and their use to deliver or expose antigens has been disclosed in the art.

For instance, VLPs have been made from animal viruses such as retroviruses or AAVs. Such VLPs, however, require complex structures and are not always convenient to produce.

VLPs derived from plant viruses have also been described. For instance, Sainsbury et al. (Annual Review of Phytopathology 2010 48:437-455) reports the production of VLPs from Cowpea Mosaic virus. Such constructs, however, require co-expression and assembly of two distinct subunits (L and S) or expression of a precursor polypeptide and a protease, rendering resulting VLPs difficult to correctly fold and produce.

Denis et al. (Virology 363 (2007) 59-68) have used the capsid protein of *Papaya* mosaic virus to expose short HCV viral epitopes. Similarly, Natilla and Hammond (Journal of Virological Methods 178 (2011) 209-215) have prepared VLPs from a capsid protein of a Maize Rayado Fino virus conjugated to a short (8 amino acids) peptide. Other examples were reported with Tomato Bushy stunt virus (Kumar et al. 2009, Virology 388, 185-190), Potato virus Y (Kalnciema et al 2012 Molecular Biotechnology 52 2,129) or Artichoke mottled crinckle virus (Arcangeli et al Journal of Biomolecular Structure and Dynamics Volume 32, Issue 4, 2014).

In each of these constructs, however, the resulting VLPs allowed coupling of generally only small molecules, and/or required assembly of distinct sub-units, and/or allowed only exposure of a peptide to the exterior of the VLP and/or generated large filamentous rather than icosahedral VLP structures comprising or not nucleic acids.

The present invention provides novel fusion molecules and VLPs derived from nepoviruses, having improved and unexpected properties.

SUMMARY OF THE INVENTION

The present invention relates to fusion molecules and VLPs derived from nepoviruses coat proteins and the uses thereof. The present invention shows that the coat protein of nepoviruses may be used to produce stable VLPs. The invention further shows that nepovirus coat protein is a very versatile protein which allows the fusion of large foreign compounds to the N- and/or C-terminal thereof without losing its ability to form VLPs. In addition, the present invention shows that the fusion of a compound at the C-terminus of the coat protein results in the exposure of the compound on the surface of VLPs, whereas a compound fused to the N-terminal leads to its internalization into the VLPs, making the compound inaccessible to antibodies ("caging"). It is therefore possible to produce VLPs having two distinct properties: the surface exposure and/or the protection by internalization (caging) of compounds of interest. Moreover, the VLPs are produced with a single type of coat protein, are quite small in size and simple in structure and nucleic acid-free. Also and advantageously, the coat proteins of nepoviruses may be fused to very large proteins (above 200 amino acids) without losing their ability to assemble into VLPs. To our knowledge, no viral protein has been described in the art having all of these properties simultaneously.

An object of the invention thus resides in virus-like particles comprising or consisting of nepovirus coat proteins.

A further object of the invention is a virus-like particle comprising or consisting of nepovirus coat proteins conjugated to a compound. Conjugation may be covalent (e.g., through genetic fusion or chemical coupling) and/or non-covalent (e.g., through ligand mediated binding).

Another object of the invention resides in a molecule comprising or consisting of a nepovirus coat protein conjugated to a compound.

Another object of the invention resides in a pharmaceutical composition comprising one or more conjugated nepovirus coat proteins or one or more virus-like particles as defined above.

The invention also relates to the use of nepovirus coat proteins to make virus-like particles.

The present invention also provides a method of producing a molecule as defined above, comprising providing a nepovirus coat protein and conjugating said protein to a compound. In a particular embodiment, the method comprises providing a nucleic acid construct encoding said conjugated molecule and expressing said nucleic acid in a host cell or an in vitro expression system.

The invention also provides a method of producing virus-like particles comprising providing a nepovirus coat protein and allowing said protein to assemble into virus-like particles. In a particular embodiment, the method comprises providing a nepovirus coat protein conjugated to a compound of interest and using such conjugated protein (possibly in mixture with other coat proteins) to make the virus-like particle. Alternatively, or in addition, the method further comprises a step of adding a reactive or active group to the virus-like particle or of incorporating a reactive or active group in the virus-like particle during production or assembly.

The invention also concerns the use of a nepovirus coat protein to deliver a compound to a subject.

Further objects of the invention include a nucleic acid molecule encoding a nepovirus coat protein conjugated to a compound of interest, a vector comprising such a nucleic acid, as well as a host cell containing the same.

The invention has wide utility in the pharmaceutical industry, to produce e.g., vaccines, adjuvants, drugs or imaging agents, for instance, for human or veterinary applications, as well as for research uses.

LEGEND TO THE FIGURES

The patent or application file contains at least one drawing executed in color. Copies of this patent or patent application publication with color drawing(s) will be provided by the Office upon request and payment of the necessary fee.

FIG. 1: Schematic representation of pEAQ vector T-DNA region and constructs derived thereof. The backbone of the T-DNA region, extending from the right border (RB) to the left border (LB), is represented in grey shades. Open reading frame (ORF) of interest is flanked by sequences of Cowpea mosaic virus untranslated regions (CPMV UTRs) under control of Cauliflower mosaic virus 35S promoter (P35S). Native Grapevine fanleaf virus (GFLV) coat protein (CP) as well as its TagRFP- and EGFP-tagged variants were introduced by Gateway cloning as schematically indicated. L1 corresponds to the 7-amino-acid $Gly_3$-Ser-$Gly_3$ linker sequence. L2 corresponds to the 15-amino-acid linker sequence resulting from Gateway recombination. Complete amino-acid-sequences of the expressed proteins are provided at the end of the document (sequence). P19: Tombusvirus P19 silencing suppressor. NPTII: neomycin phosphotransferase II gene.

Figure 2:
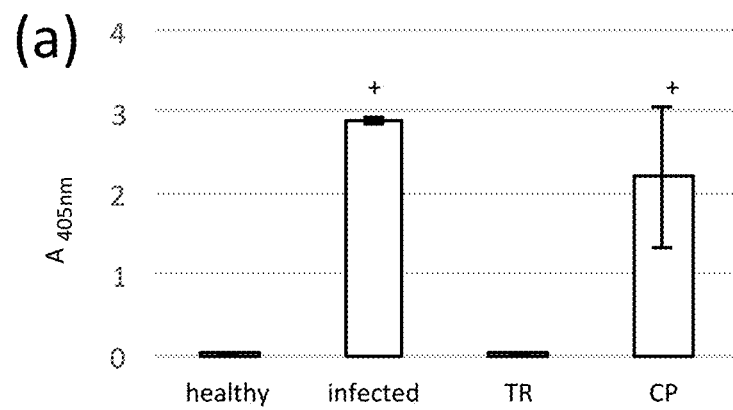
Figure 2:
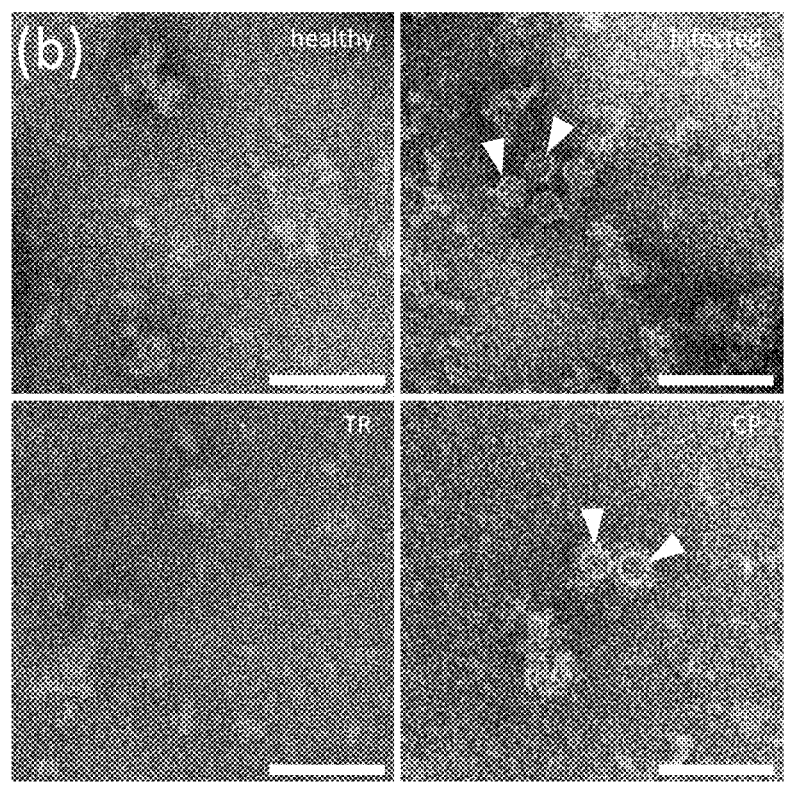

FIG. 2: Transient expression of GFLV CP in N. benthamiana leaves leads to VLP production. (a) Expression of GFLV CP in N. benthamiana leaves at 7 days post-agroinfiltration or at 14 days post-infection was determined by DAS-ELISA using anti-GFLV antibodies for detection and para-nitrophenylphosphate as substrate for alkaline phosphatase. Bars represent the mean absorbance obtained with three different leaves for each condition. Error-bars correspond to 95% confidence intervals. Samples were considered positive (+) when $O.D._{405\ nm}$ exceeded the healthy control sample mean value by at least a factor of three. (b) ISEM micrographs resulting from observations performed on the same extracts than analyzed by DAS-ELISA. Approximately 30 nm particles (arrowheads) were detected only in GFLV-infected and CP expressing samples. Scale bars: 100 nm.

Figure 3:
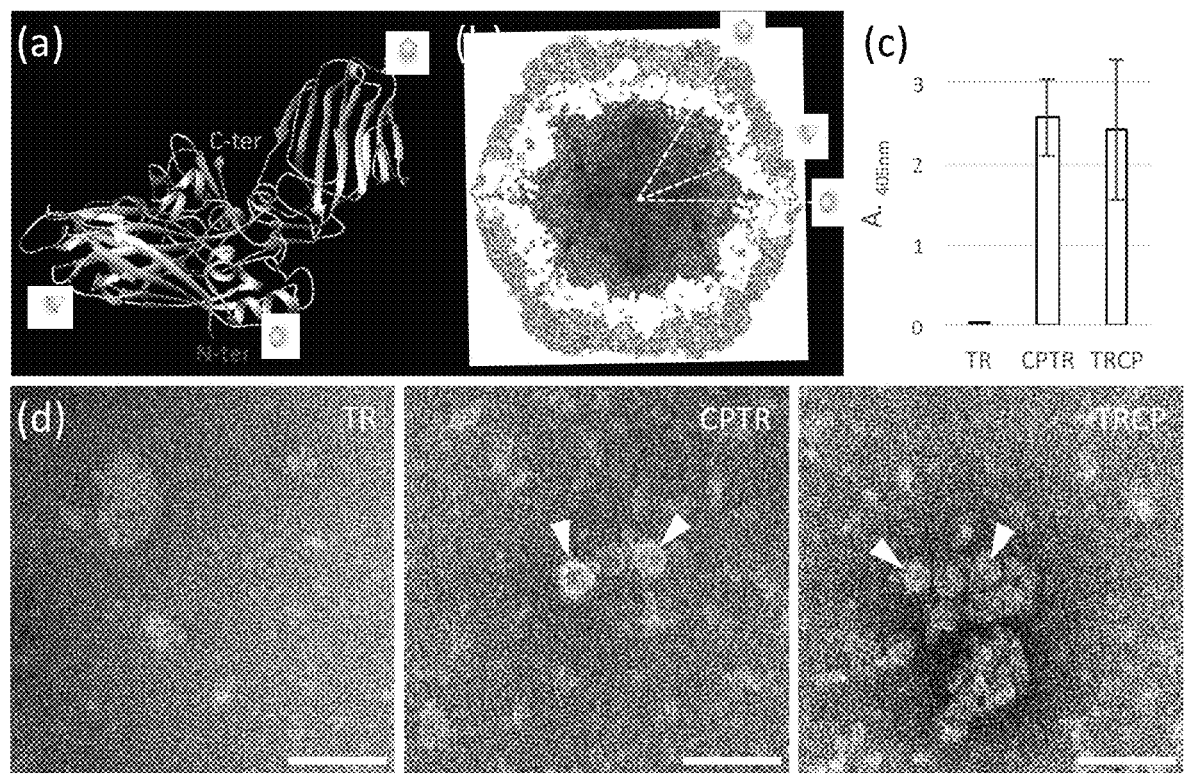

FIG. 3: Fusion of TagRFP (TR) to the N- or C-terminal ends of GFLV CP is compatible with VLP formation. (a) Ribbon diagram view of a GFLV CP subunit and (b) surface-shaded cross-section of a particle according to the 3 Å resolution atomic structure (PDB code 4V5T, Schellenberger et al., 2011). Positions of the CP N- and C-termini are indicated in red and green, respectively. The pentagon, triangle and oval symbolize the icosahedral 5-fold, 3-fold and 2-fold icosahedral symmetry axes, respectively. Residues in the cross-section plane appear in white. (c) Expression of GFLV CP in N. benthamiana crude leaf extracts 7 days after agro-infiltration with TR, CPTR or TRCP. DAS-ELISA was performed using anti-GFLV antibodies and sample considered positive (+) when $O.D._{405\ nm}$ value exceeded the healthy control sample mean value by at least a factor of three. Bars represent the mean absorbance obtained with three different leaves for each condition. Error-bars correspond to 95% confidence intervals (d) ISEM micrographs resulting from observations performed on the same extracts than analyzed by DAS-ELISA. Arrowheads point to VLPs trapped by anti-GFLV antibodies in CPTR and TRCP clarified leaf extracts. Scale bars: 100 nm.

Figure 4:
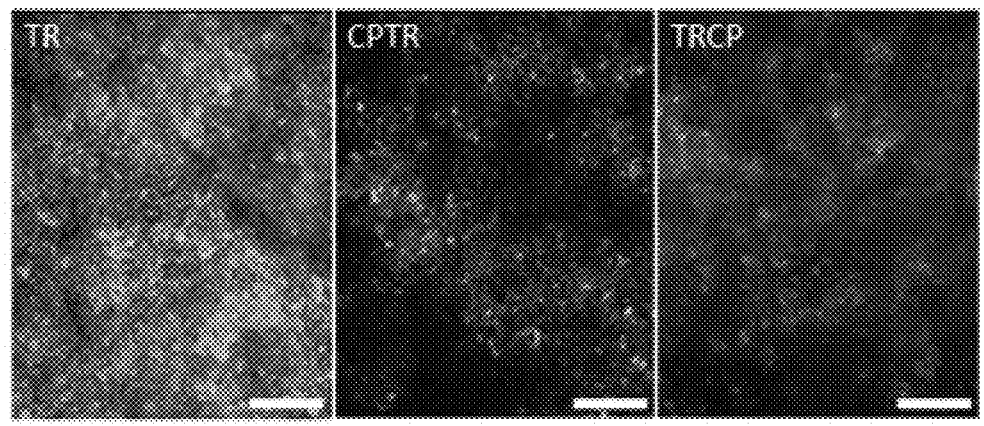

FIG. 4: Epifluorescence macroscopy images of agro-infiltrated Nicotiana benthamiana leaves expressing TR, CPTR or TRCP. Filters used for excitation and emission are as follow: $\lambda_{ex}$625-655-of $\lambda_{em}$665-715 nm. Scale bars: 300 µm.

Figure 5:
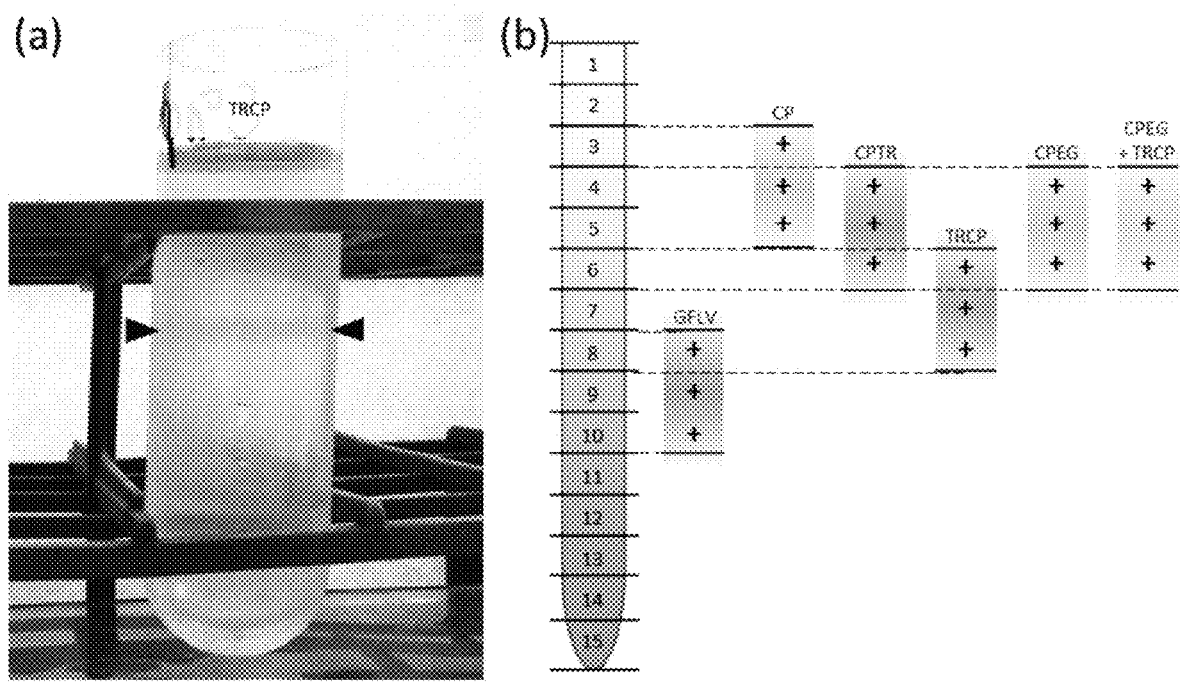

FIG. 5: Additional information concerning the purification of VLPs. (a) Bright pink band after linear sucrose gradient centrifugation of TRCP VLPs. (b) Schematic representation of the location of virus- and VLP-enriched fractions in linear sucrose gradients. The collected 2 mL fractions are numbered from 1 (top of the gradient) to 15 (bottom). RNA-containing virions were localised measuring the $O.D._{260}$ values of the different fractions. VLPs-enriched fractions were identified by semi-quantitative ELISA.

Figure 6:
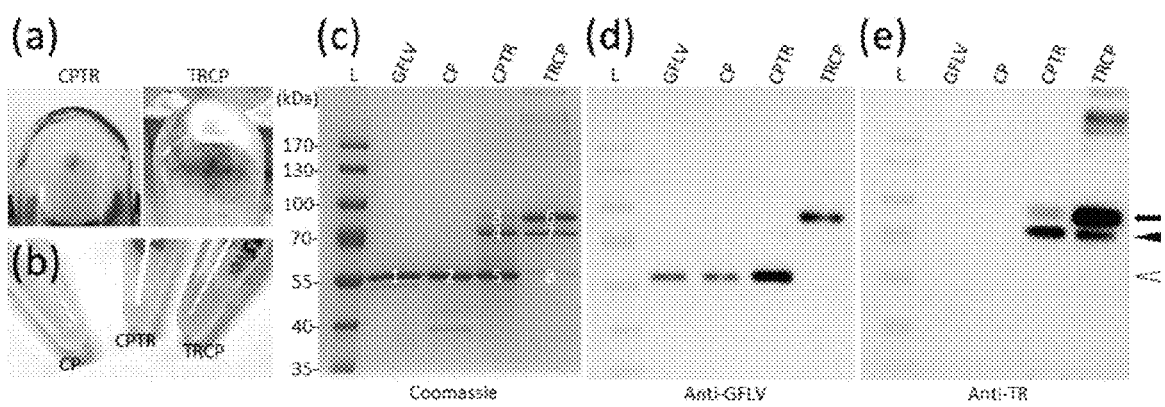

FIG. 6: Recombinant VLPs can be purified from CP, CPTR and TRCP expressing leaves. (a) Pink pellets resulting from CPTR (left panel) and TRCP (right panel) purifications at final ultracentrifugation stage. (b) Purified CP, CPTR and TRCP in solution. Note the pink color of CPTR and TRCP samples. (c) Coomassie-blue stained gel of GFLV, CP, CPTR and TRCP purified particles after SDS-Page. 6 µg of GFLV-particles equivalent were separated in each lane. Major bands in the gel are numbered from 1 to 8. (d and e) Corresponding western blotting analyses of GFLV, CP, CPTR and TRCP samples using anti-GFLV (d) or anti-TagRFP (TR, e) antibodies. 0.05 µg of GFLV-particles equivalent were used in each lane. White arrowhead indicates bands with expected size for CP. Arrow points to bands with expected size for full-length TRCP and CPTR fusions, respectively. Black arrowhead points to major TRCP or CPTR truncated products. L: molecular mass markers. Mass (kDa) are indicated to the left.

Figure 7:
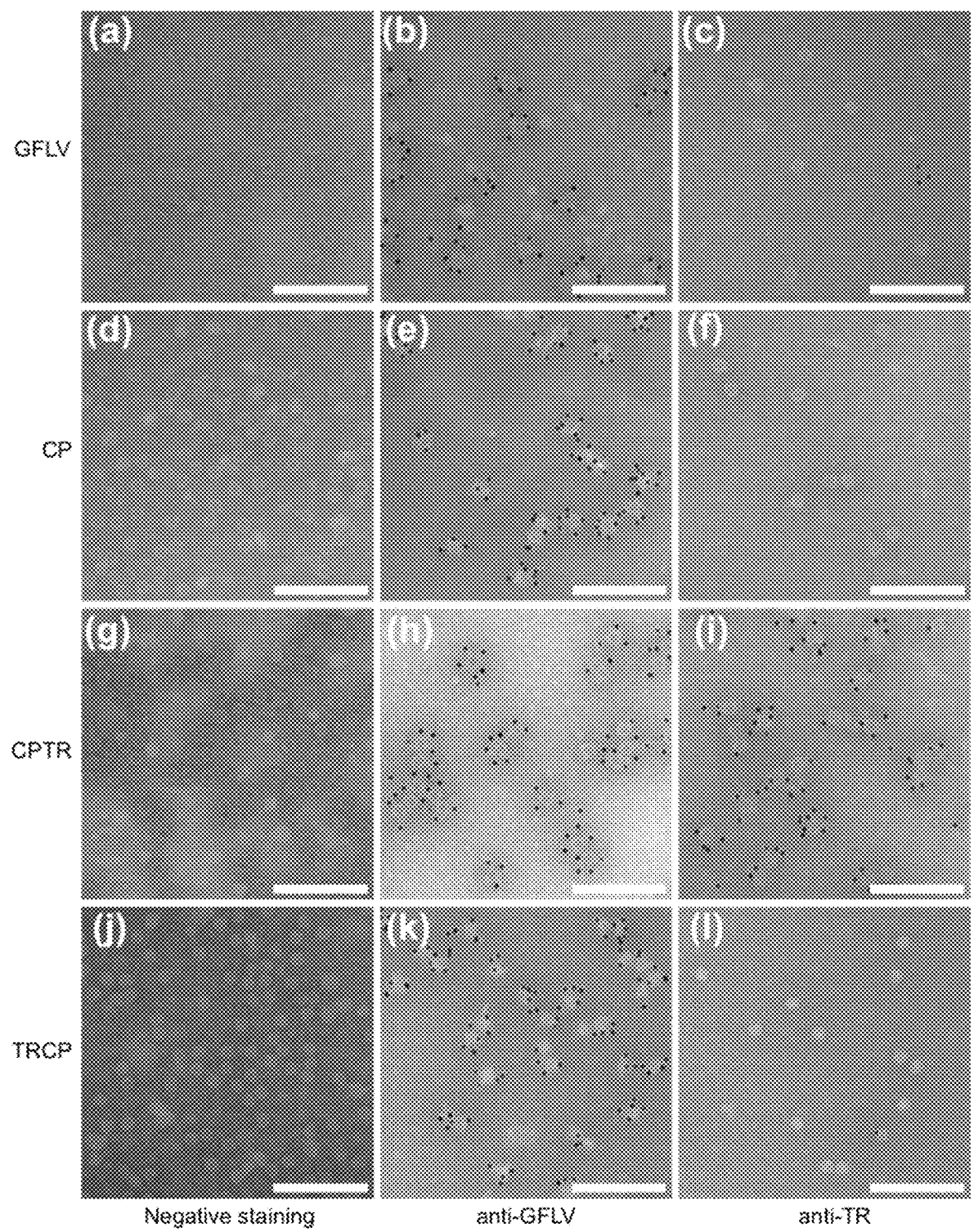

FIG. 7: Protein fused to the N- or C-terminal end of GFLV CPs are encaged or exposed to the outer surface of VLPs, respectively. Electron micrographs of purified GFLV (a, b, c), CP VLPs (d, e, f), CPTR VLPs (g, h, i) and TRCP VLPs (j, k, l). Samples were processed for negative staining only (a, d, g, j) or for ISEM using anti-GFLV (b, e, h, k) or anti-TR (c, f, i, l) antibodies and anti-rabbit antibodies conjugated to 10 nm colloidal gold particles for decoration. Scale bars: 200 nm.

Figure 8:
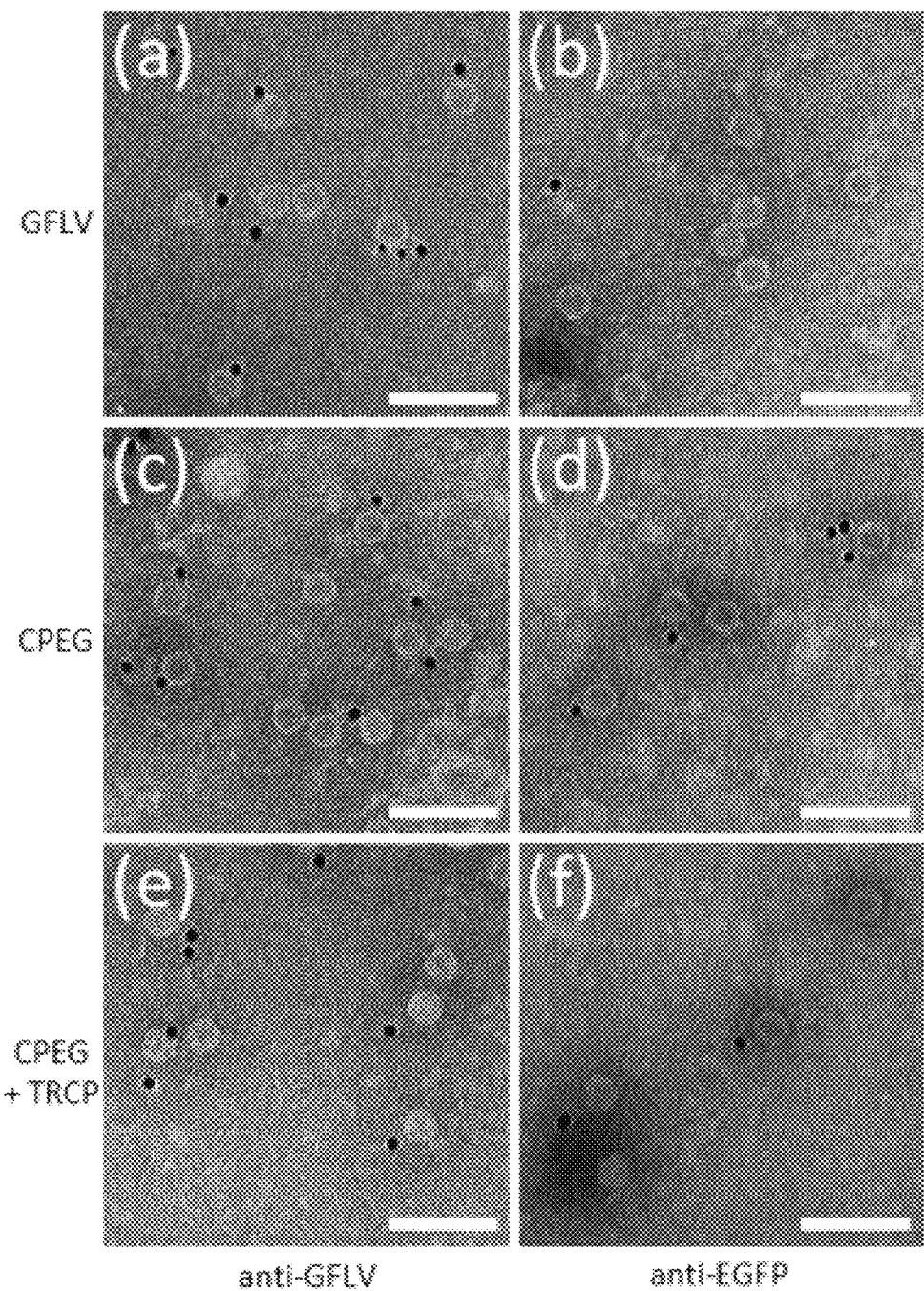

FIG. 8: VLPs can be purified from N. benthamiana leaves coexpressing CPEG and TRCP. Transmission electron micrographs of purified GFLV (a, b), CPEG VLPs (c, d) and CPEG+TRCP VLPs (e, f) after immunogold labeling. Samples were processed for ISEM using anti-GFLV (a, c, e) or anti-EGFP (b, d, f) antibodies and particles decorated using anti-mouse antibodies conjugated to 10 nm colloidal gold. Scale bars: 100 nm.

Figure 9:
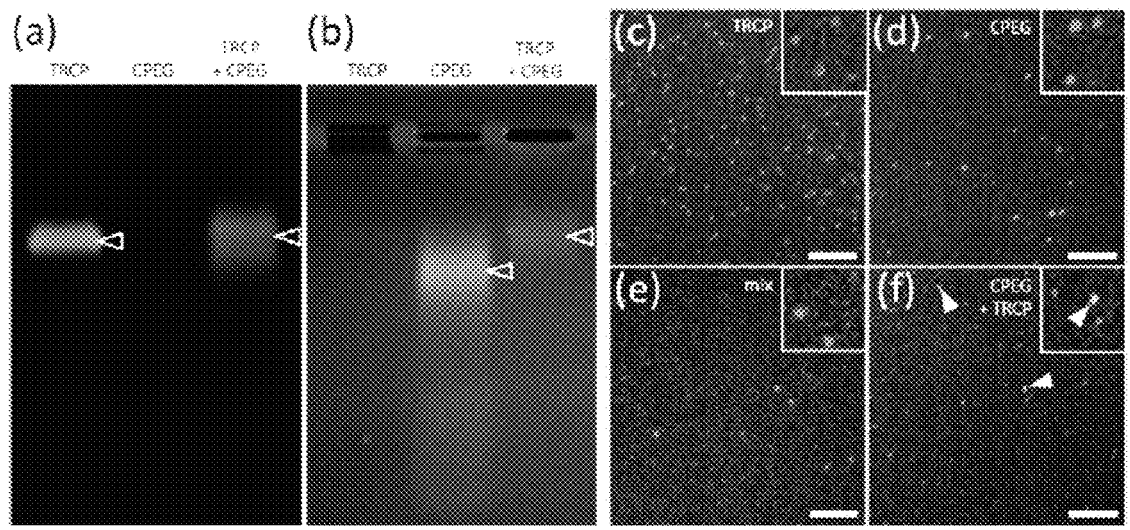

FIG. 9: Hybrid VLPs are produced upon coexpression of CPEG and TRCP. (a, b) Fluorescent imaging of TRCP, CPEG or CPEG+TRCP VLPs separated by native agarose gel electrophoresis. Imaging was done sequentially using a G:box imaging system, first at an excitation of $\lambda_{ex}$480-540 nm and an emission of $\lambda_{em}$590-660 nm to detect TagRFP (a), then at $\lambda_{ex}$450-485 nm and $\lambda_{em}$510-540 nm to detect EGFP (b). Fluorescent VLPs in the gel are indicated by empty arrowheads. (c to f) Single particle microscopy images of purified TRCP (c), CPEG (d), mixed TRCP and CPEG VLPs at 1:1 ratio (e) and coexpressed CPEG+TRCP (f). Epifluorescence imaging was done sequentially at $\lambda_{ex}$455-495 nm-$\lambda_{em}$505-555 nm to detect EGFP and at $\lambda_{ex}$532.5-557.5-$\lambda_{em}$570-640 nm to detect TagRFP. White arrowheads point at hybrid VLPs. Scale bars: 5 µm.

Figure 10:
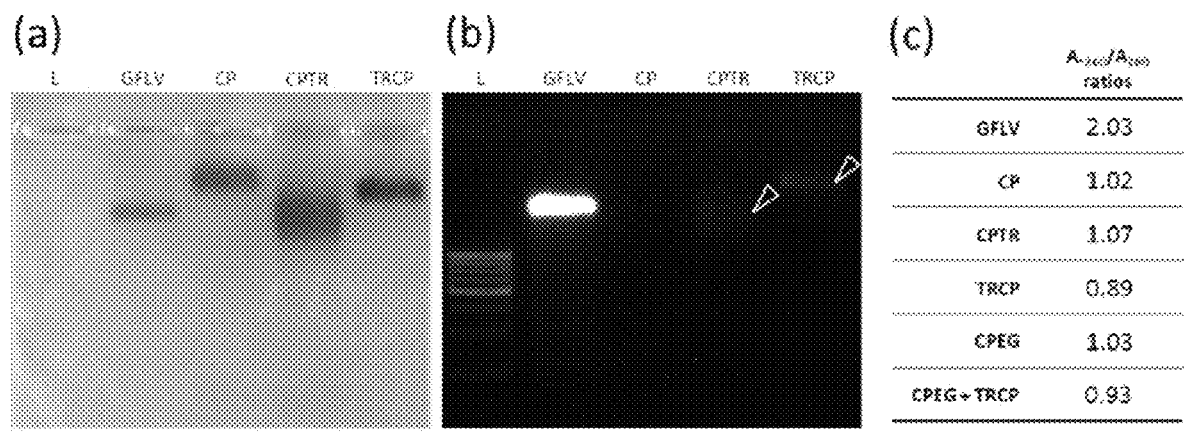

FIG. 10: Purified VLPs are nucleic acids-free. (a and b) Purified GFLV and CP, CPTR and TRCP VLPs separated by native agarose gel electrophoresis after Coomassie blue (a) and ethidium bromide staining (b). Arrowheads point to bands corresponding to cross-talk. (c) $O.D._{260}/O.D._{280}$ ratios of purified samples.

Figure 11:
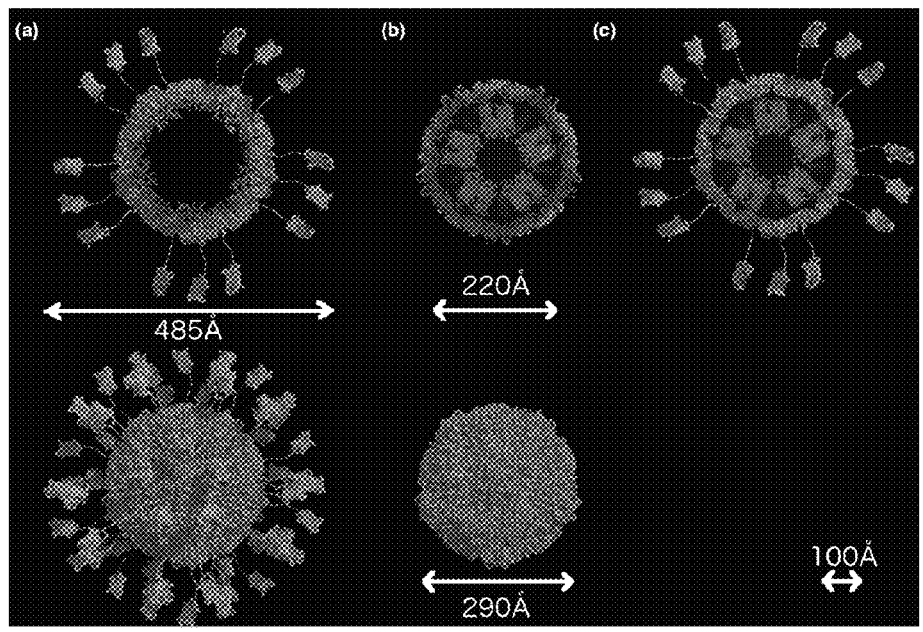

FIG. 11. Molecular models of fluorescent VLPs. (a) CPEG VLP including 60 CPs fused with EGFP in C-terminal position. (b) TRCP VLP including 60 CPs fused with TR in N-terminal position. (c) TRCPEG VLP including 60 CPs fused with EG in C-terminal and with TR in N-terminal positions. All VLPs are depicted in the same orientation in ribbon representation, with the CP in blue, EGFP in green, TagRFP in red and linker peptide in yellow.

Figure 12:
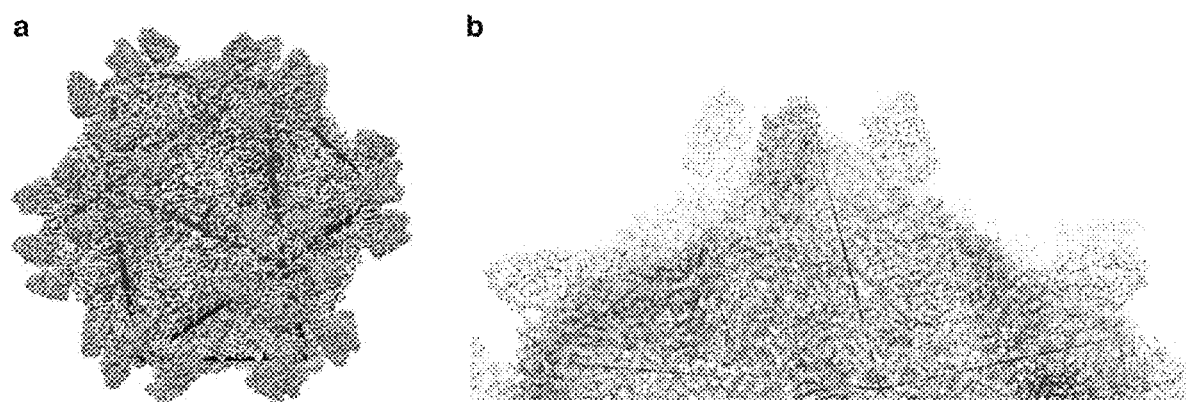

FIG. 12. The 2.8 Å resolution cryo-EM structure of the GFLV-Nb23 complex. a: Global 3D reconstruction of the GFLV-Nb23 complex with Nb23 shown in cyan on the GFLV outer surface. Icosahedral edges are indicated by red triangles. Nb23 forms a stoichiometric 1:1 complex with the viral capsid protein (CP) resulting in 60 Nb23 bound per virion. b: Detailed view of the cryo-EM map with the fitted atomic model showing the three CP and three Nb23 per icosahedron face.

Figure 13:
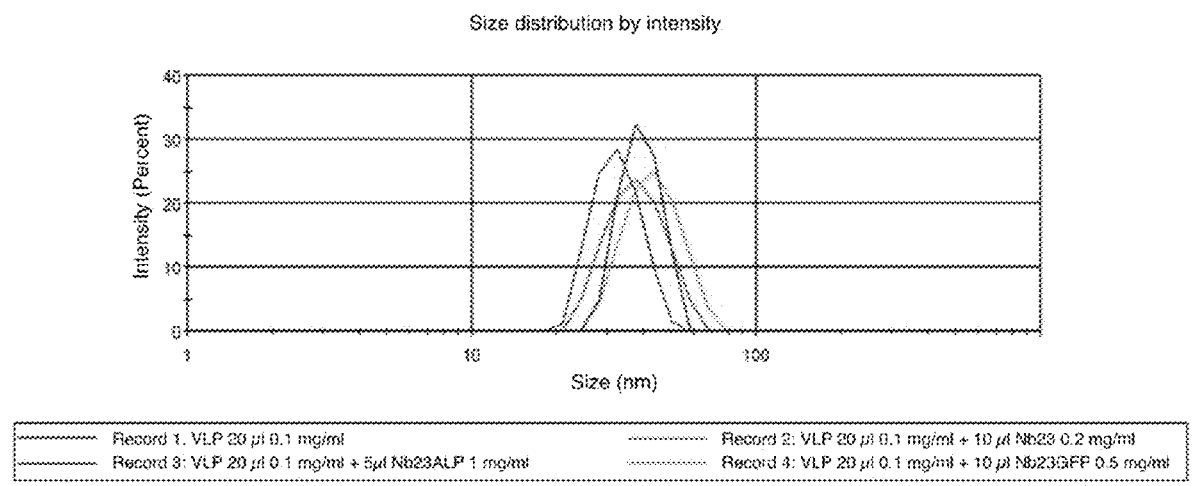

FIG. 13. Nb23-mediated decoration of TRCP VLP measured by dynamic light scattering (DLS). The graph corresponds to the size distribution by intensity of purified TRCP VLPs alone (grey curve) or decorated with either Nb23 (red curve), Nb23GFP (blue curve) or Nb23:ALP (green curve). All particles are monodisperse with diameters of 32.0+/−2 nm (mean+/−SD, n=3) for TRCP VLP, 37.8+/−2 nm (mean+/−SD, n=3) for VLP saturated with Nb23, 43.8+/−2 nm (mean+/−SD, n=3) for VLP saturated with Nb23:GFP and 40.0+/−2 nm (mean+/−SD, n=3) for VLP saturated with Nb23:ALP.

Figure 14:
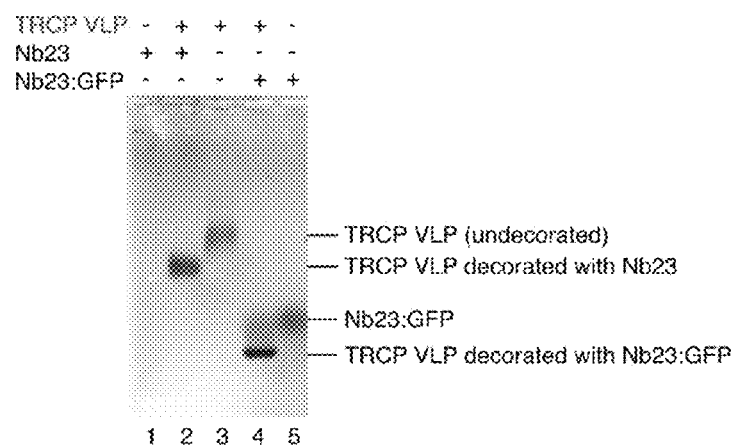

FIG. 14. TRCP VLP can be decorated with Nb23 and Nb23:GFP. TRCP VLP after native agarose gel electrophoresis and Coomassie blue staining. Lane 1: Nb23 alone. Lane 2: TRCP VLP decorated with Nb23. Lane 3: TRCP VLP alone. Lane 4: TRCP VLP decorated with Nb23:GFP. Lane 5: Nb23:GFP.- or Nb23:GFP alone. Note the shifts in migration of the VLP when decorated (lanes 2 and 4 compared to 3). Note also that migration is dependent on the net charge of the complexes rather their molecular masses.

Figure 15:
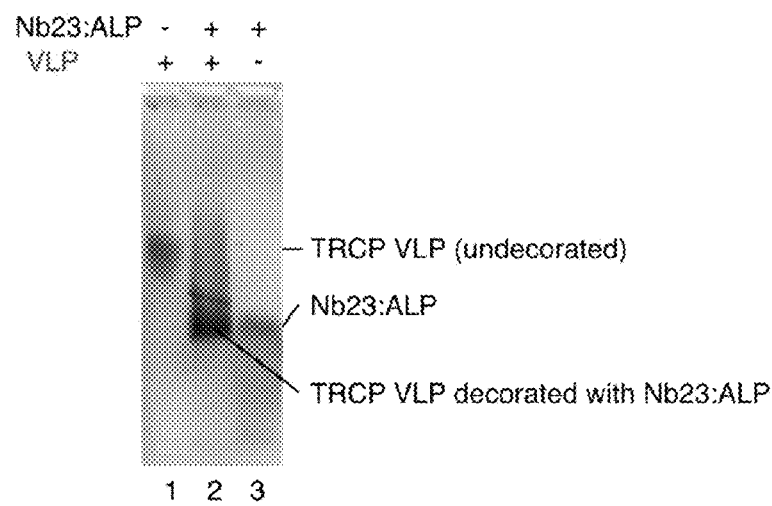

FIG. 15. Efficient display of Nb23ALP at the surface of RFP:CP-derived VLPs. TRCP VLP after native agarose gel electrophoresis, Coomassie blue staining and FastRed staining. Lane 1: TRCP VLP alone. Lane 2: TRCP VLP decorated with Nb23ALP. Lane 3: Nb23ALP alone. Note that Alkaline phosphatase remains functional upon binding to VLPs.

Figure 16:
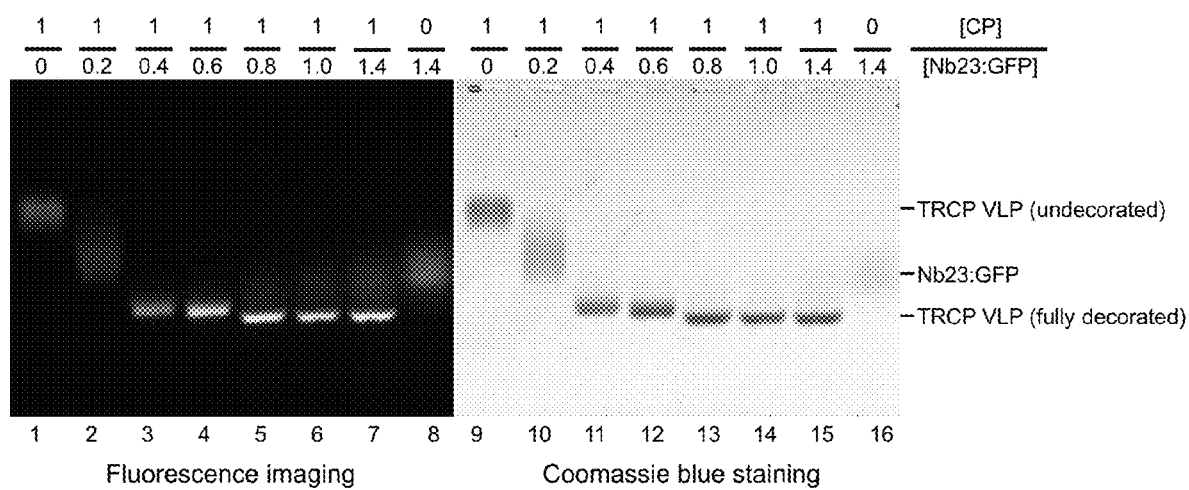

FIG. 16. Nb23GFP forms a stoichiometric 1:1 complex with the viral capsid protein (CP). TRCP VLP was incubated in the presence of increasing amounts of Nb23GFP and separated by native agarose gel electrophoresis. Molecular ratios between GFLV CP and Nb23:GFP are given above each lane. Gel was imaged under epifluorescence illumination (left) and after Coomassie blue staining (right). Note the progressive shift in migration of TRCP VLP that is proportional to the addition of Nb23GFP molecules. Note also that fully decorated TRCP VLP with Nb23GFP appear yellow (lanes 5 and 6) whereas TRCP VLP is red and Nb23GFP is green.

DETAILED DESCRIPTION OF THE INVENTION

The present invention relates to fusion molecules and VLPs derived from nepoviruses coat proteins, and the uses thereof. The invention particularly provides nepovirus coat proteins conjugated to compounds, and their use to produce nucleic-acid-free virus-like particles that either expose and/or encage said compounds. The invention shows that it is possible to produce particles by assembly of a single nepovirus coat protein in such a way that (i) encapsidation of native viral RNA is avoided, (ii) a first compound (e.g., a foreign protein or peptide) is surface exposed and/or (iii) a second compound (e.g., a foreign protein or peptide), which can be the same or different from the first compound, is encaged/protected inside the particle. These conjugated proteins and VLPs may be used to expose and/or encage any compound of interest and have utility in various fields such as the pharmaceutical, agro, or veterinary areas.

An object of the invention thus resides in virus-like particles comprising, or consisting of, or obtainable from nepovirus coat proteins.

A further object of the invention is a virus-like particle comprising or obtainable from nepovirus coat proteins conjugated to a compound. Conjugation may be covalent (e.g., through genetic or chemical coupling) and/or non-covalent (e.g., through ligand mediated binding).

Another object of the invention resides in a molecule comprising or consisting of a nepovirus coat protein conjugated to a compound.

A further object of the invention is a virus-like particle obtainable by assembly of nepovirus coat proteins conjugated to a compound.

VLPs

The term “virus-like-particle” or “VLP” more specifically designates a particle which is essentially made by assembly of coat proteins. VLPs are typically devoid of nucleic acids and not infectious. Preferred unmodified VLPs of the invention are icosahedral. Also, in unmodified form, they usually are small particles having a diameter below 50 nm, typically between 20-40 nm, more preferably between 25-35 nm, such as about 30 nm. The invention indeed shows that nepovirus coat proteins of the invention lead to the production of particles that are small in size and simple in structure. Such characteristics represent a further advantage of the invention. Of course, the size of the VLPs may be modified when large compounds are conjugated to the coat protein, as disclosed in the present application.

In one embodiment, VLPs of the invention are essentially composed of or obtained from several copies of a same nepovirus coat protein (homoVLPs), preferably a nepovirus coat protein conjugated to a compound.

In another embodiment, VLPs of the invention are composed of, or comprise, or are obtained from a mixture of distinct nepovirus coat proteins (heteroVLPs). Examples of such heteroVLPs include (i) VLPs comprising a mixture of a nepovirus coat protein and fragments thereof, or (ii) VLPs comprising a mixture of a conjugated nepovirus coat protein and a non-conjugated nepovirus coat protein.

In a further embodiment, VLPs of the invention are composed of, or comprise, or are obtained from a mixture of a nepovirus coat protein conjugated to a first compound and a nepovirus coat protein conjugated to a second compound (hybridVLPs). In a preferred hybridVLP, a mixture of the same nepovirus coat protein is used fused to a first and second compound, respectively. A most preferred hybridVLP comprises or is obtained from a mixture of a nepovirus coat protein conjugated in C-ter to a first compound and a nepovirus coat protein conjugated in N-ter to a second compound. A second most preferred hybridVLP comprises the nepovirus coat protein and an exposed compound which is conjugated to the surface of the particle by ligand-mediated conjugation. A third most preferred hybridVLP comprises an encaged compound which is N-terminally conjugated to the nepovirus coat protein and an exposed compound which is conjugated to the surface of the particle by ligand-mediated conjugation.

In heteroVLPs or hybridVLPs, the ratio between the various coat proteins may be varied and adjusted by the skilled artisan according to the needs and operating conditions, without affecting the assembly of the VLP.

VLPs of the invention may be prepared using any nepovirus coat protein. In this regard, the term “nepovirus coat protein” designates any coat or capsid protein or polypeptide derived from a nepovirus, e.g., obtained from a nepovirus, or having the sequence of a coat protein of a nepovirus, or having a sequence designed from a sequence of a coat protein of a nepovirus. The term coat protein includes recombinant proteins, synthetic proteins, or purified proteins. The coat protein may be a polypeptide having an amino acid sequence identical to that of a nepovirus or may contain structural modifications such as mutations, deletions and/insertions of one or several amino acid residues, as long as the protein retains the ability to assemble into a particle.

The invention may be implemented with coat proteins derived from any nepovirus. In particular, the invention may use coat proteins derived from a nepovirus selected from GFLV, ArMV, CNSV, BRSV, GBLV, BRV, TRSV, CLRV, RpRSV or any other nepovirus as defined by the International Committee on Taxonomy of Viruses (ICTV, see Worldwide Website: ictvonline.org/virustaxonomy.asp). The amino acid sequences of coat proteins derived from distinct nepoviruses are provided as SEQ ID NO: 1-8.

In a particular embodiment, the nepovirus coat protein is a polypeptide comprising all or part of anyone of SEQ ID NOs: 1 to 8 and able to assemble into a VLP. "Part" of a sequence designates preferably a continuous portion of at least 80% of that sequence, more preferably of at least 85%, even more preferably at least 90%, 95%, or more.

In a preferred embodiment, the nepovirus coat protein for use in the invention is a coat protein derived from a GFLV. Several strains of GFLV have been described in the art and are available, such as GFLV-F13 (Viry et al. 1993), or GFLV-GHu (Vigne et al., 2004). As a particular example, the invention uses a nepovirus coat protein derived from any strain of GFLV such as F13.

In a most preferred embodiment, the nepovirus coat protein for use in the invention is a polypeptide comprising all or part of the amino acid sequence of SEQ ID NO: 1, or a sequence having at least 90% identity to SEQ ID NO: 1. The term "identity" in relation to an amino acid sequence as used herein refers to the degree of correspondence between two amino-acid sequences (no gaps between the sequences). In other terms, it is the extent, expressed as a percentage, to which two amino acid sequences have the same amino acid at equivalent positions. The % identity can be determined by known computer programs such as BLAST, FASTA, etc.

A particular example of a coat protein is a protein comprising or consisting of SEQ ID NO: 1.

Another particular example of a coat protein is a protein comprising or consisting of amino acids 2-505 of SEQ ID NO: 1.

Another particular example of a coat protein is a protein comprising or consisting of amino acids 1-504 or 2-504 of SEQ ID NO: 1.

Another particular example of a coat protein is a protein comprising or consisting of amino acids 1-503 or 2-503 of SEQ ID NO: 1.

Another example of a coat protein is a protein comprising or consisting of SEQ ID NO: 1 with 1-5 amino acid substitutions.

A further particular example of a coat protein for use in the invention is a polypeptide comprising all or part of the amino acid sequence of SEQ ID NO: 2, or a sequence having at least 90% identity to SEQ ID NO: 2. A particular example of a coat protein is a protein comprising or consisting of SEQ ID NO: 2, with or without the N-ter methionine residue.

A further particular example of a coat protein for use in the invention is a polypeptide comprising all or part of the amino acid sequence of SEQ ID NO: 3, or a sequence having at least 90% identity to SEQ ID NO: 3. A particular example of a coat protein is a protein comprising or consisting of SEQ ID NO: 3, with or without the N-ter methionine residue.

A further particular example of a coat protein for use in the invention is a polypeptide comprising all or part of the amino acid sequence of SEQ ID NO: 4, or a sequence having at least 90% identity to SEQ ID NO: 4. A particular example of a coat protein is a protein comprising or consisting of SEQ ID NO: 4, with or without the N-ter methionine residue.

A further particular example of a coat protein for use in the invention is a polypeptide comprising all or part of the amino acid sequence of SEQ ID NO: 5, or a sequence having at least 90% identity to SEQ ID NO: 5. A particular example of a coat protein is a protein comprising or consisting of SEQ ID NO: 5, with or without the N-ter methionine residue.

A further particular example of a coat protein for use in the invention is a polypeptide comprising all or part of the amino acid sequence of SEQ ID NO: 6, or a sequence having at least 90% identity to SEQ ID NO: 6. A particular example of a coat protein is a protein comprising or consisting of SEQ ID NO: 6, with or without the N-ter methionine residue.

A further particular example of a coat protein for use in the invention is a polypeptide comprising all or part of the amino acid sequence of SEQ ID NO: 7, or a sequence having at least 90% identity to SEQ ID NO: 7. A particular example of a coat protein is a protein comprising or consisting of SEQ ID NO: 7, with or without the N-ter methionine residue.

A further particular example of a coat protein for use in the invention is a polypeptide comprising all or part of the amino acid sequence of SEQ ID NO: 8, or a sequence having at least 90% identity to SEQ ID NO: 8. A particular example of a coat protein is a protein comprising or consisting of SEQ ID NO: 8, with or without the N-ter methionine residue.

The proteins may be prepared by recombinant technology (i.e., expression in a cell or in vitro system), by synthesis, purification, or combinations thereof. In this regard, the proteins may be produced by expression in plant cells, in planta, in bacteria (e.g., in $E.\ coli$), or in other eukaryotic cells. Alternatively, expression may be performed in in vitro systems. Also, the proteins may be modified to improve their stability. In particular, the coat proteins may contain one or more peptidomimetic bonds such as for instance intercalation of a methylene ($-CH_2-$) or phosphate ($-PO_2-$) group, secondary amine ($-NH-$) or oxygen ($-O-$), alpha-azapeptides, alpha-alkylpeptides, N-alkylpeptides, phosphonamidates, depsipeptides, hydroxymethylenes, hydroxyethylenes, dihydroxyethylenes, hydroxyethylamines, retro-inverso peptides, esters, phosphinates, phosphinics, phosphonamides and the like.

Nepovirus coat proteins may be used as such to produce VLPs of the invention. Also, as discussed previously, the invention shows that nepovirus coat proteins may be conjugated to large compounds without losing their ability to assemble into VLPs. Moreover, the conjugation strategy allows control of exposure/encaging of the compound. Furthermore, very large compounds can be conjugated (e.g., which can represent at least 50% of the size of the coat protein itself) without affecting the ability of the protein to assemble into VLPs.

An object of the invention thus also resides in a nepovirus coat protein conjugated to a compound.

Conjugation may be covalent or not, direct or not (i.e., via a linker), and/or chemical, enzymatic or genetic. Furthermore, conjugation may involve terminal and/or lateral coupling. Also, a conjugated coat protein of the invention may comprise one or several conjugated compounds.

Conjugation can be carried out by any acceptable means of bonding taking into account the chemical nature and obstruction of the coat protein and compound. In this regards, coupling can thus be performed by one or more covalent, ionic, hydrogen, hydrophobic or Van der Waals bonds, cleavable or non-cleavable in physiological medium or within cells.

Furthermore, while coupling can be performed at any reactive groups of the coat protein, accessibility of the reactive group in a subsequent VLP should be considered. In this regard, the inventors have found that coupling at the N-term and/or C-term ends of the coat protein does not affect the ability of the coat protein to form a particle. Such terminal coupling is thus most preferred for the present invention. In addition, the inventors have surprisingly found that the fusion of a compound at the C-terminus of a nepovirus coat protein results in the exposure of the compound on the surface of particles prepared with the conjugate, whereas a compound fused to the N-terminal leads to its internalization into the VLPs, making the compound inaccessible to antibodies ("caging"). It is therefore possible to adjust the coupling strategy to the type of compound, and also to produce VLPs having two distinct properties: the surface exposure and the protection by internalization (caging) of compounds of interest.

In a first preferred embodiment, conjugation is obtained by covalent coupling to the coat protein, typically by genetic fusion (i.e., by expression in a suitable system of a nucleic acid construct encoding the nepovirus coat protein and the compound as a genetic fusion), most preferably at the N-ter and/or C-ter of the coat protein.

In a particular embodiment, the invention relates to a nepovirus coat protein conjugated at its N-terminal end to a compound (TRCP). A typical structure of such conjugates is Compound-(Linker)$_n$-Coat with n=0 or 1. Conjugation at the N-ter end more preferably comprises conjugation at the first N-ter amino acid of the coat protein. The present invention does indeed show that conjugation at amino acid Met$_1$ of SEQ ID NO: 1 or at amino acid Gly$_1$ of a coat protein comprising amino acids 2-505 of SEQ ID NO: 1 or a variant thereof can generate molecules that can form VLPs and that encage the conjugated compound inside of the VLP.

In another particular embodiment, the invention relates to a nepovirus coat protein conjugated at its C-terminal end to a compound (CPTR). A typical structure of such conjugates is Coat-(Linker)$_n$-Compound with n=0 or 1. Conjugation at the C-ter end more preferably comprises conjugation at anyone of the last three C-ter amino acids of the protein. The present invention does indeed show that conjugation at amino acid Phe$_{503}$, Pro$_{504}$ or Val$_{505}$ of SEQ ID NO: 1 or a variant thereof can generate molecules that can form VLPs and that expose the conjugated compound outside of the VLP. More preferably, C-ter conjugation involves conjugation to the last C-ter amino acid residue of the coat protein.

The compound may be coupled directly to the coat protein, or indirectly by means of a linker. Means of covalent chemical coupling, include e.g., the use of bi- or multifunctional agents containing e.g., alkyl, aryl, peptide or carboxyl groups. Examples of linkers include any neutral amino acid or peptide sequence, such as for instance G$_3$S, G$_3$SG$_3$, or DPAFLYKVVRSFGPA (SEQ ID NO: 13).

In a preferred embodiment, the compound is covalently linked to the coat protein, directly or via a linker.

In a further preferred embodiment, the compound and coat protein are linked by a peptide bond, either directly or via a linker.

In an alternative preferred embodiment, conjugation is obtained by (typically non-covalent) ligand-mediated attachment to the particles. Such mode of conjugation allows efficient exposure of compounds on the surface of the particles. Such mode may also be combined with the genetic coupling, to produce hybridVLPs.

In such an embodiment, a compound is conjugated to the particles after particle assembly, by adding to the VLP a reactive or active group. The active group can be linked to a ligand, and the ligand is allowed to bind the particles, leading to attachment.

The ligand may be any molecule that binds the coat protein by affinity. Examples of suitable ligands include, for instance, anti-coat protein antibodies, or derivatives thereof retaining antigen specificity. Examples of such antibodies include, without limitation, monoclonal antibodies, nanobodies (e.g., derived from the structure of single chain only immunoglobulins found in camelids), single chain antibodies (i.e., ScFv or VNAR fragments), diabodies, etc.

The term nanobody (or VHH, Hamers-Casterman et al., 1993) designates a single chain polypeptide consisting essentially of three CDRs (complementarity-determining regions CDR1, CDR2 and CDR3) separated by four FR domains (for Framework regions) and essentially devoid of a light chain or a constant domain. The terms "nanobodies", "nanobody", "VHH", "VHH antibody fragment" or "single-domain antibody" are used interchangeably. Nanobodies typically have the following structure: FR1-CDR1-FR2-CDR2-FR3-CDR3-FR4. Preferably, the nanobodies of the invention are synthetic molecules produced by recombinant or chemical technologies. Nanobodies present high epitope specificity and affinity. They are about ten times smaller than conventional IgG molecules. They are single-chain polypeptides, very stable, resisting extreme pH and temperature conditions. Moreover, they can resist to the action of proteases.

Specific examples of nanobodies that can be used in the present invention are nanobodies Nb126, Nb101, Nb23, Nbp75 and Nbp71, which have been described in WO2015/110601.

The amino acid sequence of these nanobodies is described as SEQ ID NOs: 14-18, respectively.

In a specific embodiment, the nanobody used in the invention comprises a sequence selected from anyone of SEQ ID NOs: 14-18 or a sequence having at least 80% sequence identity thereto, preferably at least 90%, 92%, 94%, 95%, 96%, 97%, 98%, 99% or more amino-acid sequence identity thereto.

Further nanobodies suitable for use in the invention are nanobodies which bind the same antigen or antigenic domain or epitope as a nanobody of anyone of SEQ ID NO: 14 to 18.

Other nanobodies or antibodies can be produced that bind a nepovirus and/or the cognate coat protein. Antibodies may be prepared by conventional techniques, by immunization of a mammal with the cognate virus or coat protein or an epitope-containing fragment thereof, followed by collection of antibody producing cells. The cells may be used to select clonal antibodies and to generate hybridomas by fusion. The sequence of the antibodies may then be determined and used to produce recombinant antibodies, single chain antibodies, Mabs, CDRs, and the like. Anti-coat protein nanobodies can be generated e.g. by immunization of a camelid animal with the cognate virus or coat protein or an epitope-containing fragment or with purified VLPs. The DNA molecule encoding said nanobodies can be determined or isolated or cloned by methods well-known in the art. Nanobodies having specific sequences as defined above can be produced by artificial synthesis or recombinant DNA technology. Nanobodies may then be tested for their ability to bind the VLP as described in the examples and/or to compete or not with (or displace) Nb126, Nb101, Nb23, Nbp75 or Nbp71.

Another example of ligands for use in the invention are single-domain antibodies VNAR fragments derived from heavy-chain antibodies (IgNAR, 'immunoglobulin new antigen receptor') of cartilaginous fishes.

The compound may be linked to the ligand through known techniques such as genetic fusion, chemical coupling, affinity binding via affinity tags (such as Strep tag or PolyHis Tag), for instance, that cause covalent or non-covalent coupling. A preferred way is by genetic fusion or chemical coupling, most preferably by genetic fusion when the compound is a polypeptide. In a particular embodiment, the compound is coupled to the ligand at an end of the ligand, most preferably covalently, such as by genetic fusion or chemical coupling. Such coupling does not substantially affect or prevent binding of the ligand to the virus coat protein or particle.

In a preferred embodiment, the invention thus relates to virus-like particles comprising or obtainable from nepovirus coat proteins, wherein said particles comprise at least one compound of interest conjugated to the coat protein by ligand-mediated attachment. Such compound is exposed at the surface of the particles. The particle may have several distinct compounds exposed on its surface through conjugation with the same or a distinct ligand. In a preferred embodiment, conjugation is performed using an anti-coat protein antibody or a derivative thereof, coupled to the compound, even more preferably using a nanobody.

In another preferred embodiment, the invention relates to virus-like particles comprising or obtainable from nepovirus coat proteins, wherein said particles comprise an encaged compound conjugated to the N-ter of the coat protein, and an exposed compound, conjugated to the surface of the particle by ligand-mediated attachment, more preferably by antibody-mediated attachment, even more preferably by nanobody-mediated attachment.

According to a further alternative embodiment, chemical conjugation to VLPs can be contemplated, such as conjugation through an exposed sulfhydryl group (Cys), attachment of an affinity tag (i.e. 6 Histidine, Flag Tag, Strep Tag, SpyCatcher etc.) to the particles for subsequent binding of compounds, or incorporation of unnatural amino acids into the VLP and compound for click chemistry conjugation.

The invention also relates to a method of producing a conjugated molecule as defined above, comprising providing a nepovirus coat protein and conjugating said protein to a compound. In a particular embodiment, providing the nepovirus coat protein comprises expressing a nucleic acid construct encoding said protein in a host cell or an in vitro expression system, and collecting the expressed protein. Subsequently, the protein may be conjugated to a compound. In an alternative route, the conjugated protein is expressed directly using a recombinant fusion nucleic acid. In this regard, in a particular embodiment, the invention relates to a method of producing a conjugated molecule as defined above comprising providing a nucleic acid construct encoding said molecule and expressing said nucleic acid in a host cell or an in vitro expression system. Recombinant production may be performed in any suitable host such as plant cells, in planta, in bacteria, yeasts, insects or in an in vitro transcription system. The expressed conjugate may be collected and stored as free molecules in any suitable medium or state. It may also be allowed to assemble into VLPs, which can then be collected and stored under suitable conditions.

Further objects of the invention also reside in a nucleic acid molecule (e.g., DNA, RNA) encoding a molecule as defined above; a vector comprising such a nucleic acid; and a host cell containing such a nucleic acid or vector.

The invention also provides a method of producing virus-like particles. The method generally comprises (i) providing a nepovirus coat protein and (ii) forming VLPs with said protein, for instance by allowing said protein to assemble into virus-like particles. In a typical embodiment, the coat proteins are maintained under conditions allowing self-assembly into particles. Such conditions include in solution at a pH comprised typically between 5 and 9, more typically between 6 and 8, and at a temperature comprised between 4° C. and 50° C., more preferably around room temperature.

In a particular embodiment, the method comprises (i) providing a nepovirus coat protein conjugated to a compound of interest and (ii) using such conjugated protein (possibly in mixture with other coat proteins) to make virus-like particles.

The nepovirus coat protein may be provided by artificial synthesis, enzymatic production/assembly, purification, and/or recombinant technology. In this respect, in a preferred embodiment, the method comprises:

providing a nucleic acid construct encoding a nepovirus coat protein, preferably conjugated to a compound,
expressing said nucleic acid in a host cell or an in vitro expression system,
optionally purifying the protein,
forming VLPs from the expressed and optionally purified proteins, and
collecting or purifying the VLPs.

In a particular embodiment, the method comprises a further step of adding to the VLPs a reactive or active group, to confer on the VLP a selected property. The active group can be linked to a ligand, and the ligand is allowed to bind the particles, leading to attachment.

In another particular embodiment, the step of forming the VLP is performed in the presence of a reactive or active group, allowing said group to be incorporated into the VLP.

In a further particular embodiment, the invention relates to a method of producing a VLP, comprising:

providing a nucleic acid construct encoding a nepovirus coat protein conjugated to a tag,
expressing said nucleic acid in a host cell or an in vitro expression system,
optionally purifying the protein,
forming VLPs from the expressed and optionally purified protein,
optionally collecting or purifying the VLPs, and
adding to the VLP a compound that binds the tag.

In the above methods, recombinant production may be performed in any suitable host such as plant cells, in planta, in bacteria, yeasts, or in an in vitro transcription system.

The VLPs may be collected and purified by conventional techniques such as, for instance, chromatography, centrifugation, and the like. Because VLPs are stable under physiological conditions, they may be stored in solution or frozen or lyophilized, according to conventional techniques.

Compounds

The compound for use in a conjugate or VLP of the invention may be any compound of interest, such as a therapeutic, diagnostic or imaging agent. The compound may also be a tag, allowing subsequent attachment of any agent of interest by exposing the conjugated coat protein or VLP to said agent under suitable conditions.

In a particular embodiment, the compound is a chemical entity of biological interest such as a small chemical molecule (e.g., antibiotic, antiviral, immunomodulator, antineoplastic, etc.), a peptide or polypeptide (such as a cytokine, a hormone, a toxin, an antigen), a protein (such as an enzyme, an antibody (such as a nanobody) or a part of an antibody), a nucleic acid (e.g., a siRNA or miRNA), or a marker (such as a fluorescent or luminescent agent).

In a particular embodiment, the compound is a protein, polypeptide or peptide. With such type of compound, the conjugates of the invention can be produced by genetic fusion.

Particular examples of such compounds include, for instance antibodies or nanobodies, or fragments or derivatives thereof. In this regard, the invention surprisingly shows that coat proteins of nepoviruses may be fused to very large proteins (above 200 amino acids) without losing their ability to assemble into VLPs. The conjugates of the invention may thus be used to expose or encage very large proteins.

Other examples of such compounds include, for instance peptide or protein antigens. Such compounds are typically conjugated in C-terminal, so as to allow their exposure at the surface of a resulting particle. In this manner, the conjugate or resulting VLP can be used as a vaccine or immunogenic composition, to induce or stimulate an immune response against the antigen.

Specific examples of conjugation in C-terminal is non-covalent (ligand-mediated) conjugation, preferably a conjugation with at least one nanobody.

Another example of such compounds include peptides or proteins with affinity to metal or tracer molecules such as gadolinium, silver, gold etc.

Another example of such compounds include toxins, enzymes or toxic molecules which should preferably not be exposed in the organism before they have reached their target tissue. Examples of such toxic compounds include, for instance, caspases, the cytosine deaminase and uracil phospho-ribosyltransferase Fcy and Fur, ribosome inactivating proteins, and bacterial and plant toxins, which act by inhibiting protein synthesis in eukaryotic cells. The toxins of the Shiga and ricin family inactivate 60S ribosomal subunits by an N-glycosidic cleavage, which releases a specific adenine base from the sugar-phosphate backbone of 28S rRNA. Members of the family include shiga and shiga-like toxins, and type I (e.g. trichosanthin and luffin) and type II (e.g. ricin, agglutinin and abrin) ribosome inactivating proteins (RIPs). All these toxins are structurally related. RIPs have been of considerable interest because of their potential use, conjugated with monoclonal antibodies, as immunotoxins to treat cancers. Further, trichosanthin has been shown to have potent activity against HIV-1-infected T cells and macrophages.

Another example of such compounds includes cell targeting ligands. Such compounds allows specific or targeted binding to cell receptors or structures, thus allowing targeting of the conjugate or VLP to a preferred target cell or tissue. Examples of such targeting ligands include ligands of cell surface receptors, or receptors of cell surface proteins, or antibodies (such as nanobodies) or fragments thereof.

Another example of such compounds includes cell-penetrating peptides and transduction domains. Such compounds allows internalization of conjugate or VLP in the cell. Examples of such peptides include tat peptide of HIV-1.

In a particular embodiment, a conjugate of the invention comprises a nepovirus coat protein conjugated at the C-term end to a targeting ligand and conjugated at the N-term end to a toxic compound. Such conjugate allows formation of a VLP having the targeting ligand exposed at the surface and the toxic compound encaged.

Pharmaceutical Compositions and Methods

The invention also relates to a pharmaceutical composition comprising at least one VLP as defined above and, preferably, one or more pharmaceutically acceptable excipients.

The invention also relates to a pharmaceutical composition comprising at least one conjugated nepovirus coat protein as defined above and, preferably, one or more pharmaceutically acceptable excipients.

Depending on the presence or absence, and on the nature of a compound or active group bound to the coat protein, the compositions of the invention may have various utilities such as therapeutic compositions, vaccines, adjuvants, diagnostic compositions, immunogenic compositions, research samples, etc.

The compositions of the invention advantageously comprise a pharmaceutically acceptable vector or excipient. The pharmaceutically acceptable excipient can be selected from any suitable and conventional excipient, depending on the form of the composition. In particular, for solid compositions such as tablets, pills, powders, or granules, the composition may comprise e.g., lactose, dextrose, sucrose, mannitol, or sorbitol. A lubricant, such as talc or stearic acid, a binder, such as starch or gelatin, a disintegrant such as agar, and/or a sweetener may be further added to the composition as well. For semi-solid compositions, the excipient can, for example, be an emulsion or oily suspension. Liquid compositions, in particular injectables or those included in a soft capsule, can include a diluent or solvent such as, for example, water, physiological saline solution, aqueous dextrose, an alcohol, an oil and analogues thereof.

The compositions or conjugates of the invention can be administered by any suitable route such as, without limitation, by parenteral (e.g., subcutaneous, intravenous or intramuscular route), oral, rectal, ocular or intranasal routes. The pharmaceutical compositions typically comprise an effective dose of a VP or conjugate or compound, e.g., any dose that gives a therapeutic effect for a given condition and administration schedule.

Depending on the nature of the compound conjugated to the coat protein, the VLPs and compositions of the invention can be used for treating, preventing, diagnosing or imaging various pathologies.

In this respect, the invention relates to VLPs or conjugates as defined above for use as a medicament.

The invention relates to VLPs or conjugates as defined above for use as a vaccine.

The invention relates to VLPs as defined above for use as an adjuvant or immunomodulator. Indeed, VLPs of the invention prepared e.g., from non-conjugated nepovirus coat proteins may be used as suitable adjuvants or immunomodulatory compositions to stimulate an immune response in a mammal.

The invention relates to VLPs or conjugates as defined above for use as a diagnostic agent.

The invention relates to VLPs or conjugates as defined above for use as a tracer.

The present invention also relates to the use of a nepovirus coat protein to reduce exposure of a compound in vivo.

The present invention also relates to the use of a nepovirus coat protein to improve exposure of a compound in vivo.

Further aspects and advantages of the invention will be disclosed in the following experimental section, which shall be considered as illustrative.

Examples

A. Experimental Procedures

Construction of Binary Plasmids

Coding sequences for GFLV-$CP_{F13}$, TagRFP and EGFP were amplified by PCR using Phusion high fidelity DNA polymerase according to the manufacturer's instructions (New England Biolabs, Thermo Fisher Scientific, Massachusetts) using pVec2ABC (Virg et al., 1993; Schellenberger et al., 2010; Vigne et al., 2013), pTagRFP-C (Evrogen, Russia) and pEGFP-N1 (Clontech, California) as templates, respectively. The translational fusions TRCP and CPTR, corresponding respectively to N- or C-terminal fusions of GFLV-$CP_{F13}$ with TagRFP, were obtained by overlapping PCRs (Ho et al., 1989) using above described PCR products as templates and overlapping primers encoding the $Gly_3$-Ser-$Gly_3$ peptide linker sequence. The attB-flancked CP, TR, CPTR and TRCP PCR products were cloned by Gateway recombination into the pDONR/Zeo entry vector (Invitrogen, Thermo Fisher Scientific, Massachusetts) and further recombined into the pEAQ-HT-DEST1 binary plasmid (Sainsbury et al., 2009). For CPEG, in which the C-terminus of GFLV-$CP_{F13}$ is fused to EGFP, a pDONR™/Zeo vector containing the CP coding sequence devoid of stop codon was used for cloning by recombination in a homemade Gateway expression vector deriving from the pEAQ-HT-DEST1 (Sainsbury et al., 2009) vector by the introduction of the EGFP encoding sequence (Clontech, California) downstream of the attR2 recombination site. Recombination resulted in the introduction of the DPAFLYKVVRSFGPA linker peptide between GFLV-$CP_{F13}$ C-terminal residue and EGFP (FIG. 1 and List of sequences). Sequences of Nanobodies derived constructs can be found in WO2015/110601.

Plant Material, Virus Infection and Virus-Like Particles Production

C. quinoa and N. benthamiana plants were grown in greenhouses at 22/18° C. (day/night) temperatures. GFLV-$CP_{F13}$ infectious crude sap derived from pMV13+ pVec$_{Acc65I}$2ABC-infected material (Schellenberger et al., 2010) was used to mechanically inoculate a large number of three weeks old C. quinoa plants. Plant were harvested 14 days post-inoculation and used for virus purification. For mechanical inoculations of N. benthamiana, three weeks old plants were inoculated with purified GFLV-$CP_{F13}$. VLPs were produced by transient expression after agro-infiltration of N. benthamiana leaves. Binary plasmids were introduced by electroporation and maintained in Agrobacterium tumefaciens strain GV3101::pMP90. Cultures were grown to stable phase in Luria-Bertani media with appropriated antibiotics, pelleted and then resuspended in sterile water, alone or in a 1:1 ratio for coexpression, to a final optical density of 0.5 at 600 nm. Suspensions were infiltrated into four weeks old N. benthamiana leaves with 2 ml plastic syringes. Healthy, infected and agro-infiltrated N. benthamiana plants were maintained in a growth chamber set at 14/10 photoperiod (4800 1x) with a temperature setting of 21/18° C. (day/night) for 7 days before leaf harvesting.

Agro-Infiltrated-Leaves Observation

Fluorescent proteins visualisation was realised 5 days post-agro-infiltration. Leaves were imaged with an Axio-Zoom V16 macroscope (Zeiss, Germany) using excitation and emission wavelength filters of 450-490 nm and 500-550 nm for EGFP imaging and of 625-655 nm and 665-715 nm for TagRFP visualization. Images were processed using Image) (Schneider et al., 2012) and GNU Image Manipulation Program (GIMP, see Worldwide Website: gimp.org) softwares.

DAS-ELISA

Healthy, infected and agro-infiltrated leaves were grinded at 1:5 w/v ratio in HEPES 100 mM pH8 and clarified for 5 min at 3000 g. GFLV or VLPs detection was performed using commercial DAS-ELISA kit (Bioreba, Switzerland) according the manufacturer's instructions. Briefly, plates were coated with polyclonal anti-GFLV antibodies diluted in coating buffer at 1:1000 dilution, incubated with clarified extracts before the addition of anti-GFLV monoclonal antibodies coupled to alkaline phosphatase at 1:1000 dilution in conjugate buffer. Three washings were done between each step of the DAS-ELISA procedure. Detection was realised using para-nitrophenylphosphate as substrate that produces a yellow water-soluble reaction product in alkaline media. Absorbance at 405 nm was measured with the Titertek Multican MCC/340 reader (Labsystems, France). Samples were considered to be positive when the absorbance values exceed the control samples by at least a factor of three after substrate incubation period.

Negative Staining, Immunocapture and Immunosorbent Electron Microscopy (ISEM)

Healthy, infected and agro-infiltrated leaves were grinded in 100 mM pH 8 HEPES buffer, clarified by centrifugation at 3000 g for 5 min and either processed for simple negative staining, for immunocapture or for ISEM. For all the grids, negative staining was performed on 300 mesh nickel grids covered with carbon-coated Formvar (Electron Microscopy Science, Pennsylvania) by incubation with 1% ammonium molybdate solution for 90 sec. For immunocaptures performed on clarified saps, grids were coated with polyclonal antibodies (Bioreba, Switzerland) at 1:100 dilution, incubated with plant extracts for 2 h at 4° C., washed in HEPES 25 mM pH 8 buffer and finally processed for negative staining. For ISEM on purified CP, CPTR and TRCP VLPs, grids were coated with homemade monoclonal antibodies against GFLV at a 0.05 mg/mL concentration and incubated with VLPs for 1 h at room temperature. After blocking with 2% w/v BSA, 10% v/v normal goat serum, 0.05% TRITON-X100 in 22.5 mM HEPES pH 8, grids were further incubated with either anti-GFLV (Bioreba, Switzerland) at 1:100 dilution or anti-TR polyclonal antibodies at 0.01 mg/mL concentration (Evrogen, Russia) for 1 h at room temperature. Immunogold labelling was performed using anti-rabbit antibodies conjugated to 10 nm colloidal gold particles at 1:50 dilution (British Biocell International, Wales). Washes with 25 mM pH8 HEPES buffer were done between all steps. ISEM on purified CPEG and CPEG+TRCP VLPs were performed in a similar manner except that polyclonal antibodies against GFLV (Bioreba, Switzerland) were used for capture and either home-made monoclonal antibodies mix against GFLV or monoclonal anti-EG antibodies (Roche, Germany) employed for detection. Finally, immunogold labelling was performed using anti-mouse antibodies conjugated with 10 nm colloidal gold particles (British Biocell International, Wales). Observations were realised using a Philips EM208 transmission electron microscope. Film-based photographs were acquired onto Kodak Electron Image Films SO-163 (Electron Microscopy Science, Pennsylvania) and revealed with the adapted chemicals (Electron Microscopy Science, Pennsylvania). Finally, photographs were scanned to obtain digital electron microscope images and processed using GNU Image Manipulation Program (GIMP, see Worldwide Website: gimp.org).

GFLV-CP Structure Representation and Analysis

CP subunit and capsid representations were made using the previously 3 Å resolved GFLV-F13 atomic structure (PDB ID: 4V5T, Schellenberger, Sauter, et al., 2011) with the UCSF Chimera package (Pettersen et al., 2004). The CP subunit ends accessibility data were obtained using VIPERdb (Carrillo-Tripp et al., 2009).

Virus and Virus-Like Particles Purification

GFLV-CP$_{F13}$ virus particles were purified from *C. quinoa* infected-plants according to Schellenberger, et al., 2011. VLPs were purified from agro-infiltrated *N. benthamiana* leaves following the same experimental procedure, except that the final discontinuous sucrose gradient was omitted. Briefly, a minimum of 350 grams of leaves were grinded in extraction buffer, filtered, incubated with bentonite and finally clarified by centrifugation for 15 min at 1900 g. VLPs were then precipitated from clarified crude sap by adding PEG-20000 and sodium chloride. Contaminating elements were removed by centrifugation on a sucrose cushion followed by a sucrose density gradient fractionation. 2 ml fractions were collected from which aliquots at 1:500, 1:5000 and 1:10000 dilutions were processed for a semi-quantitative DAS-ELISA assay to identify VLP-enriched fractions that were further pooled before final ultracentrifugation at 290,000 g for 2 hours. After resuspension in HEPES 25 mM pH8, VLPs aliquots were diluted for quantification by a quantitative DAS-ELISA assay (Vigne et al. 2013) using the GFLV-CP$_{F13}$ virus particles as a standard.

SDS-Page Electrophoresis, Western-Blot and Mass Spectrometry

For SDS-Page analysis, 6 μg of GFLV-particles equivalent from each purified sample were separated on an 8% acrylamide gel and stained with Coomassie blue using Instant Blue (Expedeon, England). For mass spectrometry, SDS-Page bands of interest were excised and proteins destained, reduced, alkyled, trypsin-digested overnight, chemotrypsin-digested and finally processed for nanoLC-MSMS analysis on a nanoU3000 (Dionex, Thermo Fisher Scientific, Massachusetts)-ESI-MicroTOFQII (Bruker, Massachusetts). Mass spectrometry data were analysed with the help of Mascot (Matrix Science Limited, England) and Proteinscape (Bruker, Massachusetts). For Western-Blot analyses, 0.05 μg of each sample were resolved on an 8% acrylamide gel and denatured proteins electrotransferred onto Immobilon PVDF membranes. Membranes were incubated either with rabbit polyclonal anti-GFLV antibodies at a 1:1000 dilution or with commercial polyclonal anti-TR antibodies (Evrogen, Russia) at a 1:5000 dilution. Proteins were revealed by chemiluminescence after incubation with goat anti-rabbit conjugated to horseradish peroxydase at a 1:12500 dilution (Thermo Fisher Scientific, Massachusetts) and Lumi-Light solution (Roche, Germany). Images were taken with a G:Box imaging system (Syngene, England), analysed with GeneTools (Syngene, England) and finally processed with GIMP (see Worldwide Website: gimp.org).

Single-Particle Epifluorescence Microscopy

Purified particles from TRCP, CPEG or CPEG+TRCP samples were diluted in HEPES 25 mM pH8 in order to obtain individual spots upon imaging on an inverted epifluorescence microscope Axio Abserver Z1 (Zeiss, Germany) equipped with an Orca Flash4.0 camera (Hamamatsu, Japan) and Spectra X light engine (Lumencor, Oregon). Excitation and emission wavelength filters were 455-495 nm and 505-555 nm for EGFP and of 532.5-557.5 nm and 570-640 nm for TagRFP. Images were finally processed using Image) (Schneider et al., 2012) and GIMP softwares (see Worldwide Website: gimp.org).

Native Agarose Gel Electrophoreses

Native gel electrophoreses of purified virions and VLPs was done in 1% w/v agarose gels in 0.5× Tris Acetate EDTA (TAE) or Tris-Acetate (TA) buffers at pH ranging between 8.0 and 9.0. For nucleic-acids detection, 5 μg of virus particles or VLPs were diluted in loading buffer (10% v/v glycerol, HEPES 25 mM pH 8) supplemented with EtBr at 0.1 μg/mL. After electrophoretic separation, the EtBr-pre-stained gel was first processed for nucleic-acid content using the Gel Doc system (Bio-Rad, California) equipped with a 302 nm excitation source and a 520-640 nm band-pass filter for emission. In a second step, gel was processed for Coomassie blue staining as mentioned previously.

For fluorescence imaging of native gels, 3 μg of purified VLP samples were diluted in the loading buffer and native gel electrophoresis performed in the absence of EtBr. Imaging was done with a G:Box imaging system (Syngene, England) equipped with 450-485 nm excitation LED module and a 510-540 nm band-pass filter for emission for EGFP visualisation. TR excitation was realised with a 480-540 nm LED module and fluorescence emission collected after filtering through a 590-660 nm band-pass filter. For FastRed staining, gels were incubated in FastRed solution in the presence of 1 mM MgCl$_2$ according to manufacturer instruction (Sigma).

Modeling

The crystal structures of GFLV (PDBid 4V5T), EG (PD-Bid 1GFL) and TR (PDBid 3M22) were used to model the CPEG, TRCP or TRCPEG VLPs. Chimeric CPs were created with Modeller (Eswar et al., 2006) by appending the linker and corresponding FP sequences to the free C- and N-terminal ends of the CP pointing outside and inside the VLP, respectively. Full capsids were reconstituted using the icosahedral symmetry in PyMOL (The PyMOL Molecular Graphics System, Version 1.7.4 Schrödinger, LLC). The position of the FP in the TRCP capsid was adjusted to avoid steric clashes using Coot (Emsley et al., 2010).

Dynamic Light Scattering (DLS).

Mean particle diameters and polydispersity of TRCP VLP alone or complexed to Nb23 to Nb23:EGFP or to Nb23:ALP was estimated by DLS using a Zetasizer NanoZS (Malvern) and Nanostar (Wyatt). Five successive measurements were performed using three independent virus and protein preparations with virus at 0.1 mg/ml in Tris buffer (50 mM Tris, 100 mM NaCl, pH 8.3), Nb23 at 0.2 mg/ml, Nb23:EGFP at 0.5 mg/ml and Nb23:ALP at 1 mg/ml. Scattered intensities were recorded at 20° C. and data processed with DTS software (version 6.01) or DYMAMICS (version 7.1.8.93), respectively. All particles were monodisperse.

B—Results

1. GFLV Coat Protein Self-Assembles into Virus-Like Particles

To address the ability of GFLV coat protein (CP) to produce VLPs in planta, the sequence encoding the CP of GFLV isolate F13 (SEQ ID NO: 1 with no N-ter methionine) was introduced in the pEAQ-HT-DEST1 binary vector (Sainsbury et al., 2009) (FIG. 1) and used for transient expression in *Nicotiana benthamiana* leaves upon agro-infiltration. Samples were analysed by direct double-antibody sandwich ELISA (DAS-ELISA) at 7 days post agro-infiltration (dpi) using as positive control *N. benthamiana* leaves from GFLV-F13 infected plants at 14 days post-inoculation (dpi), and as negative controls pEAQ-HT-DEST1-driven TagRFP (TR, Merzlyak et al., 2007) agroinfiltrated leaves at 7 dpi and healthy leaves. A strong positive signal was detected in both CP-expressing and GFLV-infected samples but not in extracts from TR-infiltrated or healthy leaf material (FIG. 2a). To test the ability of transiently expressed CP to self-assemble into VLPs, the same leaf extracts were further analysed by transmission electron microscopy (TEM) after immunocapture on grids using as capture antibodies, the same polyclonal antibodies than used for coating in DAS-ELISA. Observation of negatively stained material (FIG. 2b) revealed the presence of icosahedral particles of about 30 nm in diameter in CP expressing samples but not in TR-infiltrated or healthy negative controls (FIG. 2b). Although not very abundant on grids, icosahedral particles seen in CP-expressing crude samples were very similar to GFLV-F13 particles observed under identical conditions (FIG. 2b). This indicates that GFLV CP is able to self-assemble into VLPs upon transient expression in *N. benthamiana*.

2. GFLV CP Maintains its Capacity to Assemble into VLPs Upon Fusion of its N- or C-Terminal Ends to Foreign Proteins Analysis of the GFLV atomic structure (Schellenberger et al. 2011b) reveals that the GFLV CP amino-terminal residue $Gly_1$ and the three carboxy-terminal residues $Phe_{502}$, $Pro_{503}$ and $Val_{504}$ do not contribute to the final quaternary structure of the virus capsid and are exposed at the inner and outer surfaces of the GFLV particle, respectively (FIGS. 3a and 3b). In this respect, both extremities were tested for the addition of extra residues and their impact of the capacity of the CP to form a capsid. To test this hypothesis, N- or C-terminal CP fusions to TR were produced and, respectively, named TRCP (SEQ ID NO: 10) and CPTR (SEQ ID NO: 9) hereafter (FIG. 1). Both fusions included a $Gly_3$-Ser-$Gly_3$ linker peptide (FIG. 1) to maintain flexibility between the CP and TR domains (Zilian and Maiss, 2011) and were transiently expressed in *N. benthamiana* leaves. Samples were analysed by epifluorescence macroscopy for TR expression at 5 dpa (FIG. 4), and 2 days later by DAS-ELISA for CP expression (FIG. 3c) and TEM for VLPs (FIG. 3d). While TR fluorescence was observed in all samples (FIG. 4) suggesting proper expression of the different proteins, CP was detected only in CPTR and TRCP crude extracts by DAS-ELISA (FIG. 3c), which correlated with the presence of VLPs as seen upon TEM (FIG. 3d). These results suggest that GFLV CP retains its capacity to form VLPs upon fusion of its N- or C-terminal end to TR.

To confirm our results and to gain insights into the biochemical properties of such VLPs, large-scale production in *N. benthamiana* leaves was carried out followed by purification using standard GFLV purification procedure that includes clarification and ultracentrifugation steps in the absence of protease inhibitors (see methods). In parallel, GFLV-$CP_{F13}$ virions were purified from infected *C. quinoa* leaves at 14 dpi. After linear sucrose gradient, a sharp pink band was observed in the TRCP gradient (FIG. 5a) as well as a faint pink band in the CPTR gradient (not shown), but not in infected samples (not shown). 2 mL sucrose gradient fractions were collected and those enriched in VLPs identified by semi-quantitative DAS-ELISA. While bona fide GFLV particles sedimented towards the bottom of the gradient in fractions 8-10, other particles (CP, CPTR and TRCP) located to the lighter fractions 3-5, 4-6 and 6-8, respectively (FIG. 5b). This is in agreement with previous report indicating that empty GFLV particles purified from infected plants display lower density than native RNA-containing virions (Quacquarelli et al., 1976). DAS-ELISA positive fractions were further pooled and processed for final concentration by ultracentrifugation. Remarkably, pink pellets were observed in both TRCP and CPTR samples (FIG. 6a). The final concentration of purified material (FIG. 6b) was determined by quantitative DAS-ELISA using purified GFLV-$CP_{F13}$ virions as a standard. Yields ranged from 386 to 445 µg GFLV-particles equivalent per kg of fresh leaves for the three purifications which is in the same order of magnitude than GFLV purification yields from infected *N. benthamiana* (Schellenberger, Demangeat, et al., 2011).

To assess their quality and purity, purified samples were analysed by Coomassie blue staining after SDS-PAGE (FIG. 6c), immunoblotting using anti-GFLV or anti-TR antibodies (FIGS. 6d and 6e) and mass spectrometry (data not shown). For Coomassie blue staining, 6 µg of particles equivalent of each sample were loaded on SDS-denaturing gel. In agreement with the purification of VLPs, one major protein with an observed mass of 57 kDa and co-migrating with the CP of GFLV (calculated mass 56 kDa) was present in purified samples from CP-expressing leaves (FIG. 6c, bands 1 and 2). For CPTR and TRCP samples, profiles were more complex with three major proteins of observed molecular mass of approximately 87, 73 and 57 kDa being detected (FIG. 6c, bands 3-5 for CPTR and 6-8 for TRCP) but in inverse proportions: the larger product being the most abundant and the shorter being the least abundant for TRCP (respectively approximately 69%, 24% and 7% respective abundance), the opposite for CPTR (respectively approximately 2%, 35% and 63%). Upon immunoblotting with anti-GFLV antibodies, the shorter product present in CPTR sample (FIG. 6c, band 5) was clearly revealed (FIG. 6d), strongly suggesting that band 5 corresponds to the CP of GFLV and probably represents a cleavage product of CPTR. In the TRCP sample, the larger product (FIG. 6c, band 6) immunoreacted clearly with anti-GFLV antibodies (FIG. 6d). Considering this band is about the expected size of TRCP (calculated mass: 82.8 kDa), our results suggest that the full-length TRCP is the principal protein present in the purified TRCP sample. Accordingly, band 6 gave also a strong signal upon immunodetection with anti-TR antibodies (FIG. 6e). Anti-TR antibodies immunoreacted also but weakly with the larger product present in the CPTR sample (band 3) and with the 73 kDa truncated products observed in CPTR and TRCP samples (FIG. 6e). Altogether our results suggest that the principal proteins present in purified TRCP and CPTR samples are derived from GFLV CP and thus likely represent VLPs.

To gain insights into the composition of the purified products, Coomassie-stained bands were subjected to mass spectrometry analysis leading to the identification of peptides covering nearly the entire CP for all bands analysed (FIG. 6c, data not shown). Peptides corresponding to TR were only observed for bands 3, 4, 6 and 7 and nearly full-coverage of the CPTR or TRCP proteins strictly restricted to bands 3 and 6. The 73 kDa products corresponding to band 4 and 7 displayed only partial coverage of the TR and thus represent truncated version of CPTR or TRCP, possibly due to proteolytic degradation during the purification process carried out in the absence of protease inhibitors. Altogether our results demonstrate that the full-length chimeric protein CPTR or TRCP can be purified following standard virus purification procedures and are therefore fully compatible with VLPs production. They also reveal that the CPTR fusion is more labile than TRCP, possibly as a consequence of a different orientation of TR towards the internal or external surface of VLPs upon N- or C-terminal fusion, respectively.

3. N- and C-Terminal CP Fusions are Oriented Towards the Interior or Exterior of VLPs, Respectively.

To gain insights into the orientation of N- and C-terminal CP fusions, VLPs were further subjected to negative staining and immuno-sorbent electron microscopy analyses. As expected, direct coating of purified material onto nickel grids followed by negative staining revealed the presence of numerous VLPs in all samples (FIGS. 7d, 7g and 7j) that clearly resembled GFLV particles (FIG. 7a). Under such conditions, CP and CPTR particles appeared electron-dense (FIGS. 7d and 7g) similarly to GFLV-virions (FIG. 7a). In contrast, TRCP particles were electron-lucent (FIG. 7j), possibly reflecting the orientation of TR toward the interior of the TRCP VLPs that is likely to increase the inner density of particles and decrease the penetrability to heavy metals (FIGS. 7a and 7b). To verify these hypotheses, decoration assays were performed with anti-GFLV (FIGS. 7b, 7e, 7h and 7k) or anti-TR antibodies (FIGS. 7c, 7f, 7i and 7l). While all purified particles were labelled with anti-GFLV antibodies as expected (FIGS. 7b, 7e, 7h and 7k), only CPTR particles were decorated with anti-TR antibodies (FIG. 7i), in spite of the significantly greater proportion of full-length chimeric protein present in TRCP versus CPTR particles (FIG. 6). This clearly demonstrates that CPTR and TRCP are both compatible with VLP formation that differ however in architecture. In CPTR VLPs, TR is accessible to anti-TR antibodies, highlighting the exposure of the protein towards the outer surface of particles. In contrast, in TRCP VLPs, TR is totally inaccessible to anti-TR antibodies, most likely as a consequence of the encaging of TR inside the particles. Perhaps most importantly, our results also clearly show that GFLV CP can accommodate the fusion of foreign proteins as large as fluorescent proteins that represent 50% of its own length without altering the capacity of the protein to self-assemble into VLPs.

4. Hybrid VLPs can be Produced

In view of our results, we next tested the capacity of GFLV CP to form hybrid VLPs upon co-expression of N- and C-terminal CP fusions. To do so, EGFP was selected as reporter protein and fused to the CP N-terminus as indicated in FIG. 1 (construct CPEG, SEQ ID NO: 11). As before, agro-infiltrated N. benthamiana leaves were used for expression assays and purification of VLPs carried out in the absence of protease inhibitors. CPEG expressing leaves were used as negative control and compared to leaves coexpressing CPEG and TRCP (CPEG+TRCP). In compliance with our previous results, CPEG VLPs could be purified and located to the same linear sucrose gradient fractions than CPTR VLPs (FIG. 5b). Coexpressed CPEG and TRCP also enabled the purification of DAS-ELISA immunoreactive material cosedimenting with CPEG VLPs in linear sucrose gradient (FIG. 5b). ISEM analysis confirmed the presence of VLPs in both CPEG and CPEG+TRCP samples that clearly immunoreacted with both anti-GFLV and anti-EGFP antibodies (FIG. 8), well in agreement with the predicted exposure of EGFP towards the external surface of VLPs. Considering TR is inaccessible to antibodies in ISEM upon fusion to the CP N-terminus, we further assessed the presence of EGFP and TagRFP by fluorescence imaging of VLPs separated by electrophoresis on a native agarose gel (FIG. 9). Under such conditions, distinct bands with specific migration profiles were detected in TRCP, CPEG and CPEG+TRCP samples, TRCP VLPs being visible only in the red channel ($\lambda_{excitation}$ 480-540/$\lambda_{emission}$ 590-660 nm, FIG. 9a), CPEG VLPs only in the green channel ($\lambda_{excitation}$ 450-485/$\lambda_{emission}$ 510-540 nm, FIG. 9b) and CPEG+TRCP VLPs emitting in both channels as expected for hybrid particles (FIGS. 9a and 9b, empty arrowheads).

To confirm the production of bona fide hybrid VLPs and hence the presence of particles that emit simultaneously in green and red, purified samples were further processed for single particle imaging by epifluorescence microscopy. In this manner, numerous TRCP VLPs were observed that appeared as individual spots emitting only in the red channel (FIG. 9c). Similarly, individual spots emitting only in the green channel and corresponding to CPEG VLPs were also detected but in lower density (FIG. 9d), likely reflecting the low abundance of full-length protein in purified CPEG VLPs samples (FIG. 6c). Importantly, a mix of separately purified CPEG and TRCP VLPs led to the observation of individual VLPs that were always exclusively either red or green (FIG. 9e). In contrast, yellow particles were clearly detected in CPEG+TRCP VLPs (FIG. 9f, filled arrowheads). Altogether, our results demonstrate that GFLV CP is fully compatible with the production of hybrid VLPs in which exogenous proteins as large as fluorescent proteins can be simultaneously exposed to the outer surface and encaged in the inner lumen of individual VLPs pending their fusion to either the N- or C-terminus of the CP.

5. The GFLV VLPs are Free from Nucleic Acids

To examine the content of the VLPs, native agarose gel electrophoresis was performed and gel stained either with Coomassie blue for protein content (FIG. 10a) or with ethidium bromide (EtBr) for nucleic acids (FIG. 10b). As already noticed upon fluorescence imaging of VLPs in native agarose gels (FIGS. 9a and 9b), the migration profiles of CP, CPTR and TRCP VLPs as well as purified GFLV differed significantly (FIG. 10a), probably as a consequence of difference in net charges, density and mass of the various particles. Possibly due to the rather labile nature of TagRFP when exposed at the outer surface of particles, CPTR VLPs formed a smear on the gel rather than a clear band as seen with other samples (FIG. 10a). Under UV-illumination after EtBr staining, nucleic acids were clearly detected in GFLV virions and below detectable level in CP VLPs, suggesting that such particles are, within the limits of detection of this assay, nucleic acid-free (FIG. 10b). In contrast, under identical conditions, both CPTR and the TRCP VLPs generated a weak signal likely as a consequence of the slight TR protein excitation under UV illumination (Merzlyak et al., 2007) and the use of filters incompatible with the full discrimination of TR and nucleic acid spectra rather than to the presence of nucleic acids (FIG. 10b, arrowheads). In this respect, only purified virus led to high $O.D._{260}/O.D._{280}$ values compatible with the presence of nucleic acids, whereas those measured for the different VLPs (CP, CPTR, TRCP, CPEG and CPEG+TRCP) ranged from 0.89 to 1.07 indicative of their very low or nucleic acid-free content (FIG. 10c).

6. GFLV CP-Derived VLPs are Compatible with the Simultaneous Encapsidation and Exposure of Up to 120 FPs To estimate the maximum number of FPs that could be incorporated in VLPs upon genetic fusion to the CP, we modeled CPEG- and TRCP-derived particles (see experimental procedures). Both fusions turned out to be fully compatible with the formation of VLPs (FIG. 11). According to our models, CPEG that includes the gateway-derived linker peptide leads to the formation of VLPs with an apparent diameter of 48.5 Å in which the FP is evenly distributed and floating at the particle outer surface (FIG. 11a). In contrast, TRCP results in the formation of VLPs with an outer diameter of 29.0 Å identical to the one of virions, but in which the FP forms a tightly packed layer inside particles (FIG. 11b). We also modeled TRCPEG (SEQ ID NO: 19), a theoretical CP (1000 residues) in which both termini are fused to FPs (Figure H c) revealing that, at least in silico, GFLV CP is compatible with the simultaneous encapsidation and exposure of FPs, representing altogether 120 FP per VLP. The calculated mass of such a TRCPEG VLP (6.69 MDa) is nearly twice that of a CP-only VLP (3.37 MDa).

7. Nanobodies are Versatile Tools for the Display of Foreign Proteins at the Surface of GFLV CP-Derived VLPs Nb23 which has been described in WO2015/110601 can efficiently bind to purified GFLV particles allowing the structure of the GFLV-Nb23 complex to be determined by single particle cryo-electron microscopy at 2.8 Å resolution (FIG. 12; Cryo-EM map and coordinates of the atomic model have been deposited under pdb accession code SFOJ). The structure reveals that Nb23 binds at the surface of GFLV in the vicinity of the 5-fold axis (FIGS. 12a and 12b). The outer isocontour surface of the GFLV-Nb23 reconstruction (FIGS. 12a and 12b) shows that the Nb23 molecules are positioned far enough from each other allowing 60 of them to attach per virion and reach full 1:1 stoichiometric binding with the CP without bridging neighboring CPs.

To test whether GFLV CP-derived VLPs are compatible with the binding of Nb23 similarly to viral particles, dynamic light scattering (dls) and native agarose gel electrophoresis analyses were performed. Dls revealed that TRCP VLPs alone are monodisperse with a particle diameter of 32.0 nm±2 nm (mean±SD) whereas in the presence of saturating concentration of Nb23, the diameter of TRCP VLPs increased to 37.8±2 nm (FIG. 13). Native gel electrophoresis revealed that addition of Nb23 to TRCP VLP induced a significant shift in mobility of the VLP (FIG. 14 lanes 1 to 3), we assume as a consequence in changes of the net electric charge density and mass of the various particles upon Nb23 binding to the VLPs. Altogether our results demonstrate that TRCP VLPs can be efficiently decorated with Nb23. They also reveal that Nb23 epitope is conserved suggesting that the TRCP VLP outer surface is structurally identical to that of GFLV particles.

To assess whether VLP can be decorated with larger molecules, TRCP VLP where incubated in the presence of purified Nb23 fused to EGFP (27 kDa) (SEQ ID NO: 20) or to bacterial alkaline phosphatase (ALP) (SEQ ID NO: 21), a homo-dimeric protein of approximately 58 kDa for each monomer (Muller et al., 2001), and tested by dls and native agarose gel electrophoresis. Similarly to our previous results with Nb23, a significant increase of the apparent diameter of the VLPs was observed in the presence of either Nb23:GFP (43.8+/−2 nm (mean+/−SD, n=3)) or Nb23ALP (40.0+/−2 nm (mean+/−SD, n=3)) (FIG. 13). In agreement with the efficient binding of Nb23:GFP and Nb23ALP to TRCP VLPs as suggested by our dls results, a significant shift in mobility of the VLPs was also observed upon decoration of the VLPs by Nb23:GFP (FIG. 14 lanes 3 to 5) or Nb23ALP (FIG. 15). Under these conditions, ALP was still enzymatically active as seen by the specific FastRed-staining of decorated VLP (FIG. 15).

Finally we could demonstrate that Nb23:GFP binding to VLPs is saturable since shift in VLP mobility progressively increased upon addition of increasing amount of Nb23:GFP (FIG. 16). Maximum mobility shift was observed at approximately one to one molecular ratio between GFLV CP and Nb23:GFP suggesting that up to 60 molecules of Nb23:GFP can be bound per individual VLP. Observation of the gel by fluorescence imaging further revealed that both encaged TagRFP and exposed EGFP remained fluorescent demonstrating that Nb23-mediated binding activity does not affect the activity and integrity of the latter proteins.

Altogether our results demonstrate that nanobodies allow efficient and rapid display of foreign proteins at the surface of GFLV CP-derived VLPs. They also show that molecules as large as Nb23:GFP ($\cong$42 Kda) and Nb23:ALP ($\cong$=73 kDa in its monomeric form) can be bound to VLP without loss of activity.

```
Sequences

SEQ ID NO: 1: GFLV Coat Protein amino acid sequence
MGLAGRGVIYIPKDCQANRYLGTLNIRDMISDFKGVQYEKWITAGLVMPTFKIVIRLPANAFTGLTWVMSFDAYNRIT
SRITASADPVYTLSVPHWLIHHKLGTFSCEIDYGELCGHAMWFKSTTFESPRLHFTCLTGNNKELAADWQAVVELYAE
LEEATSFLGKPTLVFDDPGVFNGKFQFLTCPPIFFDLTAVTALRSAGLTLGQVPMVGTTKVYNLNSTLVSCVLGMGGTV
RGRVHICAPIFYSIVLWVVSEWNGTTMDWNELFKYPGVYVEEDGSFEVKIRSPYHRTPARLLAGQSQRDMSSLNFYAI
AGPIAPSGETAQLPIVVQIDEIVRPDLSLPSFEDDYFVWVDFSEFTLDKEEIEIGSRFFDFTSNTCRVSMGENPFAAM
IACHGLHSGVLDLKLQWSLNTEFGKSSGSVTITKLVGDKAMGLDGPSHVFAIQKLEGTTELLVGNFAGANPNTRFSLY
SRWMAIKLDQAKSIKVLRVLCKPRPGFSFYGRTSFPV SEQ ID NO: 2: TRSV Coat Protein amino acid sequence
MGGSWQEGTEAAYLGKVTCAKDAKGGTLLHTLDIIKECKSQNLLRYKEWQRQGFLHGKLRLRCFIPTNIFCGHSMMCS
LDAFGRYDSNVLGASFPVKLASLLPTEVISLADGPVVTWTFDIGRLCGHGLYYSEGAYARPKIYFLVLSDNDVPAEAD
WQFTYQLLFEDHTFSNSFGAVPFITLPHIFNRLDIGYWRGPTEIDLTSTPAPNAYRLLFGLSTVISGNMSTLNANQAL
LRFFQGSNGTLHGRIKKIGTALTTCSLLLSLRHKDASLTLETAYQRPHYILADGQGAFSLPISTPHAATSFLEDMLRL
EIFAIAGPFSPKDNKAKYQFMCYFDHIELVEGVPRTIAGEQQFNWCSFRNFKIDDWKFEWPARLPDILDDKSEVLLRQ
HPLSLLISSTGFFTGRAIFVFQWGLNTTAGNMKGSFSARLAFGKGVEEIEQTSTVQPLVGACEARIPVEFKTYTGYTT
SGPPGSMEPYIYVRLTQAKLVDRLSVNVILQEGFSFYGPSVKHFKKEVGTPSATLGTNNPVGRPPENVDTGGPGGQYA
AALQAAQQAGKNPFGRG SEQ ID NO: 3: ArMV Coat Protein amino acid sequence
MGLAGRGSVQVPKDCQAGRYLKTLDLRDMVSGFSGIQYEKWITAGLVMPDFKVVIRYPANAFTGITWVMSFDAYNRIT
SSITTTASPAYTLSVPHWLLHHKNGTTSCDIDYGELCGHAMWFNATTFESPKLHFTCLTGNNKELAADWEFVVELYAE
FEAAKTFLGRPNFVYSADAFNGSFKFLTIPPLEYDLSTTSAYKSVSLLLGQTLIDGTHKVYNYNNTLLSYYLGIGGVV
KGRVHICSPCTYGIVLRVVSEWNGVTNNWNQLFKYPGCYIGEDGNFEIEIRSPYHRTPLRLLDAQAASAFTSTLNFYA
ISGPIAPSGETAKMPVVVQIDEIALPDLSVPSFPNDYFLWVDFSAFTVDAEEYVIGSRFFDISSTTSTVHLGDNPFAH
MIACHGLHHGILDLKLMWDLEGEFGKSSGGVTITKLCGDKATGMDGASRVCALQNMGCETELYIGNFAGANPNSALSL
YSRWLAIKLDKARSMKMLRILCKPRGNFEFYGRTCFRV
```

-continued

Sequences

SEQ ID NO: 4: TRSV2 Coat Protein amino acid sequence
MAVTVVPDPTCCGTLSFKVPKDAKKGKHLGTFDIRQAIMEYGGLHSQEWCAKGIVNPTFTVRMHAPRNAFAGLSIACT
FDDYKRIDLPALGNECPPSEMFELPTKVFMLKDADVHEWQFNYGELTGHGLCNWANVVTQPTLYFFVASTNQVTMAAD
WQCIVTMHVDMGPVIDRFELVPTMTWPIQLGDTFAIDRYYEAKEIKLDGSTSMLSISYNFGGPVKHSKKHAISYSRAV
MSRNLGWSGTISGSVKSVSSLFCTASFVIFPWEHEAPPTLRQVLWGPHQIMHGDGQFEIAIKTRLHSAATTEEGFGRL
GILPLSGPIAPDAHVGSYEFIVHIDTWRPDSQVHPPMFSSAELYNWFPTLTNLKPDANTGVVNFDIPGYIHDFASKDAT
VTLASNPLSWLVAATGWHYGEVDLCISWPRSKQAQAQEGSVSITTNYRDWGAYWQGQARIYDLRRTEAEIPIFLGSYA
GATPSGALGKQNYVRISIVNAKDIVALRVCLRPKSIKFWGRSATLF SEQ ID NO: 5: CNSV Coat Protein amino acid sequence
MSAENFVFTQLITVPAASTKGNVLAGVDILANARTTMSGFYMRWLQKGYIDTNLKLICHLPRAPFAGMSFFVLIDGTG
YLAKDAPTSLNEEEILSYPLHLVTTSDVSSYEFVLDWHRYIGQVPFAEENAFLRPTLFLVACVSSTLALSAKVEFYLE
AQSVGEELPRTLAPSPVLSYPFQNSFLEDLDLFLPPKRLTLGERETTIIPLSFAKSKKSGDAVLYSHAAARLAHFQGI
GGVLHGVVYLVGSQLVASQSRISMWSKEQHIQHQAVNVHVDTDTGVAFDLPIKDAFYASSVYGDSGAVIQVTCLCSPM
SPNAIKAPFDMIFKIRGFTPDAPMCRTINFTQRFGWFAVEPTTSTGAIKLKIWPVSNHLESEDMKVTGYTNAFLQMCQ
TSTMHFGSVIIHFSWTLFGGTTNAATAGGVVTIAEGFGPEEENFRGHCRNLSIYEGRATVPLELGTFAGPTPLKKLDF
KYRNWIRFTTPKGRNISSIFCAIEVLPGFSFYGRTGSPRLSVVGTTVPPTADASTSNSQGGDMKILEINILLPWAGGE
DEARVQDQAPLGLMFLGIS SEQ ID NO: 6: GBLV Coat Protein amino acid sequence
MGWCPKDATAGRVLEAINLREEIATGDNLVKYDWLAKGMIEPDMSVRLTVGQNPFVGISIGVCCDFSGRLAQYYDGAT
AIPIEICNQLPNFVCPISERSVFVHKINMLLAGYNLFQTQKHFADPYILVYIIDTNTLSASDEWGYTIELCVHSSVHT
TQFARTPFLTLPGTFDGTLPLDLWRGPFSFKTGKSAPREERIGINFGSKRTYNSGAKEFYSLPAAHIQLLQSVGGILH
GSVIQTGSRAISCELYMILQPDKTANNLEQAVKLPGCRVPTGGGPFSLRIQSAFLRSQIYETGVQLVIYALGGPLGAA
TISAPYQYMVHFSHITEEEGFVPRPIGTILEFNWATLAQLTLKDRFQIPARLSDLVIPGVSVHMRSNPLASIIGACGF
FRGHVTFILQWSLNVEHVKPKTYMQVQTCVGTFIPAPVKHSQILQSWVVPISQRFELRVPFDLVDYPGFNSSGGIGLD
HMQPFIDIACGDFSQLEYFNINVELKPGFEIYGRSVTPLK SEQ ID NO: 7: BRV Coat Protein amino acid sequence
MSGLVADTTLAFAKMYQCKKDAKAGHVLATIDIQECVFEDNRRVALDWLAHGLASFKYDLQLTVDSNPFVGVTLGITV
DAFDRLLPQISDEVIAVPLAFQLPTYLFPISKKGFTFQTIDFAAIAGYNFFPHVAAFGRPKIIVYIVSDNDLPASDTW
MCLVELHMTRLESSTLACSPTLVLPQAFGGDLPLDLWRGPYTFPLGGGTKRLSTSLDIGTSTTTVSGWRTVSFPAAYA
LFLQGHGGSLVGEVVHTGSAAVSCALHLCISFGGAPPTLEEALVFPGFRLPSGEGKFHIKVQTPYGRLSTLTPDCALY
VYLAGGPIAVAPMSVPYQFCIHLERLVDDGAPPRTIGLIREFNWATINNFKSDDITFAIPARLSDLVLTCGDVTMSTN
PLALLIGSCGFFRGNLTVVLEWATFLKAGDKEGTVQLTTCRGMINNVKGVRNAIQKKVVNLSLVGSVSRYLNVGDFTG
FAQSGGQVGYDEIFLEFSTNKAKQIRYLNINVELDENFELYGRTIIPLKNTAPAFASTSASAPNES SEQ ID NO: 8: BRSV Coat Protein amino acid sequence
MAGGSYAFGETIELPATVTPGTVLAVFNIFDKIQETNTKVCSKWLEQGYVSQNLTAISHLAPNAFSGIAIWYIFDAYG
KIPGDVTTTFELEMARSFDPHVQVLRDVSTSTWVIDFHKICGQTLNFSGQGYCVPKIWVIAASTFQLARSTATKFRLE
FYTRGEKLVRGLAEQPLSYPIEARHLTDLNLMLAPKQIAVGTYAMITFPVSLAAKLQSTSGRTAYSYAAGLLSHFLGV
GGTIHFVVRTTSSAFVTSKLRIALWGTVPETDQLAQMPHVDVEVNVDASLQIQSPFFSTANFGNSGSAFYVSTLCAPM
APETVETGSEYYIQIKGIEANPGLCREINYKQRFAWCLLECLDNSKASPIKVKIPSRIGNLSSKHVKVTNFVNALAIL
CATTGMHHGNCTIHFSWLWHPAELGKQLGRLKFVQGMGINNNEHIGDTMCYNSLSNTHSVPFQGSFAGPITSGGKADE
AENWIEIQSPDFSWVASLHVSIEVHEGFKFYGRSAGPLTIPATVADVSAVSGS SEQ ID NO: 9: CPTR
<u>MGLAGRGVIYIPKDCQANRYLGTLNIRDMISDFKGVQYEKWITAGLVMPTFKIVIRLPANAFTGLTWVMSFDAYNRIT
SRITASADPVYTLSVPHWLIHHKLGTFSCEIDYGELCGHAMWFKSTTFESPRLHFTCLTGNNKELAADWQAVVELYAE
LEEEATSFLGKPTLVFDPGVFNGKFQFLTCPPIFFDLTAVTALRSAGLTLGQVPMVGTTKVYNLSTLVSCVLGMGGTV
RGRVHICAPIFYSIVLWVVSEWNGTTMDWNELFKYPGVYVEEDGSFEVKIRSPYHRTPARLLAGQSQRDMSSLNFYAI
AGPIAPSGETAQLPIVVQIDEIVRPDLSLPSFEDDYFVWVDFSEFTLDKEEIEIGSRFFDFTSNTCRVSMGENPFAAM
IACHGLHSGVLDLKLQWSLNTEFGKSSGSVTITKLVGDKAMGLDGPSHVFAIQKLEGTTELLVGNFAGANPNTRFSLY
SRWMAIKLDQAKSIKVLRVLCKPRPGFSFYGRTSFPV</u>GGGSGGGMSELIKENMHMKLYMEGTVNNHHFKCTSEGEGKP
YEGTQTMRIKVVEGGPLPFAFDILATSFMYGSRTFINHTQGIPDFFKQSFPEGFTWERVTTYEDGGVLTATQDTSLQD
GCLIYNVKIRGVNFPSNGPVMQKKTLGWEANTEMLYPADGGLEGRSDMALKLVGGGHLICNFKTTYRSKKPAKNLKMP
GVYYVDHRLERIKEADKETYVEQHEVAVARYCDLPSKLGHKLN Bold: linker
underlined: coat protein SEQ ID NO: 10: TRCP
MSELIKENMHMKLYMEGTVNNHHFKCTSEGEGKPYEGTQTMRIKVVEGGPLPFAFDILATSFMYGSRTFINHTQGIPD
FFKQSFPEGFTWERVTTYEDGGVLTATQDTSLQDGCLIYNVKIRGVNFPSNGPVMQKKTLGWEANTEMLYPADGGLEG
RSDMALKLVGGGHLICNFKTTYRSKKPAKNLKMPGVYYVDHRLERIKEADKETYVEQHEVAVARYCDLPSKLGH**KLNG
GGSGGGG**<u>LAGRGVIYIPKDCQANRYLGTLNIRDMISDFKGVQYEKWITAGLVMPTFKIVIRLPANAFTGLTWVMSFDA
YNRITSRITASADPVYTLSVPHWLIHHKLGTFSCEIDYGELCGHAMWFKSTTFESPRLHFTCLTGNNKELAADWQAVV
ELYAELEEATSFLGKPTLVFDPGVFNGKFQFLTCPPIFFDLTAVTALRSAGLTLGQVPMVGTTKVYNLSTLVSCVLG
MGGTVRGRVHICAPIFYSIVLWVVSEWNGTTMDWNELFKYPGVYVEEDGSFEVKIRSPYHRTPARLLAGQSQRDMSSL
NFYAIAGPIAPSGETAQLPIVVQIDEIVRPDLSLPSFEDDYFVWVDFSEFTLDKEEIEIGSRFFDFTSNTCRVSMGEN
PFAAMIACHGLHSGVLDLKLQWSLNTEFGKSSGSVTITKLVGDKAMGLDGPSHVFAIQKLEGTTELLVGNFAGANPNT
RFSLYSRWMAIKLDQAKSIKVLRVLCKPRPGFSFYGRTSFPV</u>

Bold: linker
underlined: coat protein

-continued

Sequences

SEQ ID NO: 11: CPEG
MGLAGRGVIYIPKDCQANRYLGTLNIRDMISDFKGVQYEKWITAGLVMPTFKIVIRLPANAFTGLTWVMSFDAYNRIT
SRITASADPVYTLSVPHWLIHHKLGTFSCEIDYGELCGHAMWFKSTTFESPRLHFTCLTGNNKELAADWQAVVELYAE
LEEATSFLGKPTLVFDPGVFNGKFQFLTCPPIFFDLTAVTALRSAGLTLGQVPMVGTTKVYNLNSTLVSCVLGMGGTV
RGRVHICAPIFYSIVLWVVSEWNGTTMDWNELFKYPGVYVEEDGSFEVKIRSPYHRTPARLLAGQSQRDMSSLNFYAI
AGPIAPSGETAQLPIVVQIDEIVRPDLSLPSFEDDYFVWVDFSEFTLDKEEIEIGSRFFDFTSNTCRVSMGENPFAAM
IACHGLHSGVLDLKLQWSLNTEFGKSSGSVTITKLVGDKAMGLDGPSHVFAIQKLEGTTELLVGNFAGANPNTRFSLY
SRWMAIKLDQAKSIKVLRVLCKPRPGFSFYGRTSFPVDPAFLYKVVRSFGPAMVSKGEELFTGVVPILVELDGDVNGH
KFSVSGEGEGDATYGKLTLKFICTTGKLPVPWPTLVTTLTYGVQCFSRYPDHMKQHDFFKSAMPEGYVQERTIFFKDD
GNYKTRAEVKFEGDTLVNRIELKGIDFKEDGNILGHKLEYNYNSHNVYIMADKQKNGIKVNFKIRHNIEDGSVQLADH
YQQNTPIGDGPVLLPDNHYLSTQSALSKDPNEKRDHMVLLEFVTAAGITLGMDELYKTS

Bold: linker
underlined: coat protein

SEQ ID NO: 12: TR
MSELIKENMHMKLYMEGTVNNHHFKCTSEGEGKPYEGTQTMRIKVVEGGPLPFAFDILATSFMYGSRTFINHTQGIPD
FFKQSFPEGFTWERVTTYEDGGVLTATQDTSLQDGCLIYNVKIRGVNFPSNGPVMQKKTLGWEANTEMLYPADGGLEG
RSDMALKLVGGGHLICNFKTTYRSKKPAKNLKMPGVYYVDHRLERIKEADKETYVEQHEVAVARYCDLPSKLGHN

SEQ ID NO: 13: LINKER
DPAFLYKVVRSFGPA

SEQ ID NO: 14: Nb126
Gln Val Gln Leu Gln Glu Ser Gly Gly Gly Ser Val Gln Val Gly Gly Ser Leu Arg
Leu Ala Cys Ala Ala Ser Gly Asp Thr Phe Ser Gly Tyr Leu Ala Ala Trp Phe Arg
Gln Ala Pro Gly Lys Glu Arg Glu Gly Val Ala Ala Ile Asn Ser Val Arg His Thr
Thr Ser Tyr Ala Asn Ser Val Lys Gly Arg Phe Thr Ile Ser Lys Asp Asn Ala Asp
Asn Met Met Tyr Leu Glu Met Asn Ser Leu Lys Pro Glu Asp Thr Ala Ile Tyr Tyr
Cys Ala Ala Ala Asp Ala Ile Gly Leu Ala Glu Tyr Trp Ser Thr Pro Thr Leu Ser
Ala Ala Arg Tyr Lys Tyr Trp Gly Gln Gly Thr Gln Val Thr Val Ser Ser

SEQ ID NO: 15: Nb101
Gln Val Gln Leu Gln Glu Ser Gly Gly Gly Ser Val Gln Val Gly Gly Ser Leu Arg
Leu Ala Cys Ala Ala Ser Gly Asp Thr Phe Ser Gly Tyr Leu Ala Ala Trp Phe Arg
Gln Ala Pro Gly Lys Glu Arg Gly Val Ala Ala Ile Asn Ser Val Arg His Thr
Thr Ser Tyr Ala Asp Ser Val Lys Gly Arg Phe Thr Ile Ser Lys Asn Ala Asp
Asn Met Met Tyr Leu Glu Met Asn Gly Leu Lys Pro Glu Asp Thr Ala Ile Tyr Tyr
Cys Ala Ala Ala Asp Ala Ile Gly Leu Ala Glu Tyr Trp Ser Thr Pro Thr Leu Ser
Ala Ala Arg Tyr Lys Tyr Trp Gly Gln Gly Thr Gln Val Thr Val Ser Ser

SEQ ID NO: 16: Nb23
Gln Val Gln Leu Gln Glu Ser Gly Gly Gly Ser Val Gln Val Gly Gly Ser Leu Arg
Val Ala Cys Ala Ala Ser Gly Asp Thr Phe Ser Gly Tyr Leu Ala Ala Trp Phe Arg
Gln Ala Pro Gly Lys Glu Arg Gly Val Ala Ala Ile Asn Ser Lys Arg His Thr
Thr Ser Tyr Ala Asp Ser Val Lys Gly Arg Phe Thr Ile Ser Lys Asp Asn Ala Asp
Asn Ile Met Tyr Leu Glu Met Asn Ser Leu Lys Pro Glu Asp Thr Ala Ile Tyr Tyr
Cys Ala Ala Ala Asp Ala Ile Gly Leu Ala Glu Tyr Trp Ser Thr Pro Thr Leu Ser
Ala Ala Arg Tyr Lys Tyr Trp Gly Gln Gly Thr Gln Val Thr Val Ser Ser

SEQ ID NO: 17: Nb75
Gln Val Gln Leu Gln Glu Ser Gly Gly Gly Ser Val Gln Ala Gly Gly Ser Leu Arg
Leu Cys Val Ala Ser Glu Tyr Pro Ser Ser Thr Met Ala Trp Phe Arg
Gln Ala Pro Gly Lys Glu Arg Glu Gly Val Ala Ala Ile Asn Ser Val Arg His Thr
Thr Ser Tyr Ala Asp Ser Val Lys Gly Arg Phe Thr Ile Ser Lys Asp Asn Ala Asp
Asn Met Met Tyr Leu Glu Met Asn Ser Leu Lys Pro Glu Asp Thr Ala Ile Tyr Tyr
Cys Ala Ala Ala Asp Ala Ile Gly Leu Ala Glu Tyr Trp Ser Thr Pro Thr Leu Ser
Ala Ala Arg Tyr Lys Tyr Trp Gly Gln Gly Thr Gln Val Thr Val Ser Ser

SEQ ID NO: 18: Nb71
Gln Val Gln Leu Gln Glu Ser Gly Gly Gly Ala Val Gln Pro Gly Gly Ser Leu Lys
Leu Ser Cys Glu Ala Ser Gly Asp Val Pro Glu Asn Gly Tyr Met Ala Trp Phe Arg
Gln Ala Pro Gly Lys Glu Arg Glu Gly Val Ala Ala Ile Asn Ser Val Arg His Thr
Thr Ser Tyr Ala Asp Ser Val Lys Gly Arg Phe Thr Ile Ser Lys Asp Asn Ala Asp
Asn Met Met Tyr Leu Glu Met Asn Ser Leu Lys Pro Glu Asp Thr Ala Ile Tyr Tyr
Cys Ala Ala Ala Asp Ala Ile Gly Leu Ala Glu Tyr Trp Ser Thr Pro Thr Leu Ser
Ala Ala Arg Tyr Lys Tyr Trp Gly Gln Gly Thr Gln Val Thr Val Ser Ser

SEQ ID NO: 19: TRCPEG
MSELIKENMHMKLYMEGTVNNHHFKCTSEGEGKPYEGTQTMRIKVVEGGPLPFAFDILATSFMYGSRTFINHTQGIPD
FFKQSFPEGFTWERVTTYEDGGVLTATQDTSLQDGCLIYNVKIRGVNFPSNGPVMQKKTLGWEANTEMLYPADGGLEG
RSDMALKLVGGGHLICNFKTTYRSKKPAKNLKMPGVYYVDHRLERIKEADKETYVEQHEVAVARYCDLPSKLGHKLNG
GGSGGGG**GLAGRGVIYIPKDCQANRYLGTLNIRDMISDFKGVQYEKWITAGLVMPTFKIVIRLPANAFTGLTWVMSFDA
YNRITSRITASADPVYTLSVPHWLIHHKLGTFSCEIDYGELCGHAMWFKSTTFESPRLHFTCLTGNNKELAADWQAVV
ELYAELEEATSFLGKPTLVFDPGVFNGKFQFLTCPPIFFDLTAVTALRSAGLTLGQVPMVGTTKVYNLNSTLVSCVLG
MGGTVRGRVHICAPIFYSIVLWVVSEWNGTTMDWNELFKYPGVYVEEDGSFEVKIRSPYHRTPARLLAGQSQRDMSSL
NFYAIAGPIAPSGETAQLPIVVQIDEIVRPDLSLPSFEDDYFVWVDFSEFTLDKEEIEIGSRFFDFTSNTCRVSMGEN**

-continued

Sequences

PFAAMIACHGLHSGVLDLKLQWSLNTEFGKSSGSVTITKLVGDKAMGLDGPSHVFAIQKLEGTTELLVGNFAGANPNT
RFSLYSRWMAIKLDQAKSIKVLRVLCKPRPGFSFYGRTSFPVDPAFLYKVVRSFGPAMVSKGEELFTGVVPILVELDG
DVNGHKFSVSGEGEGDATYGKLTLKFICTTGKLPVPWPTLVTTLTYGVQCFSRYPDHMKQHDFFKSAMPEGYVQERTI
FFKDDGNYKTRAEVKFEGDTLVNRIELKGIDFKEDGNILGHKLEYNYNSHNVYIMADKQKNGIKVNFKIRHNIEDGSV
QLADHYQQNTPIGDGPVLLPDNHYLSTQSALSKDPNEKRDHMVLLEFVTAAGITLGMDELYKTS

The protein weighs 111.52 kilodaltons. In bold the CP of GFLV.

SEQ ID NO: 20: Nb23EGFP
QVQLQESGGGSVQVGGSLRVACAASGDTFSGYLAAWFRQAPGKGREGVAAINSKRHTTSYADSVKGRFTISKDNADNI
MYLEMNSLKPEDTAIYYCAAADAIGLAEYWSTPTLSAARYKYWGQGTQVTVSSGGGSGGGMVSKGEELFTGVVPILVE
LDGDVNGHKFSVSGEGEGDATYGKLTLKFICTTGKLPVPWPTLVTTLTYGVQCFSRYPDHMKQHDFFKSAMPEGYVQE
RTIFFKDDGNYKTRAEVKFEGDTLVNRIELKGIDFKEDGNILGHKLEYNYNSHNVYIMADKQKNGIKVNFKIRHNIED
GSVQLADHYQQNTPIGDGPVLLPDNHYLSTQSALSKDPNEKRDHMVLLEFVTAAGITLGMDELYKTSHHHHHH

In bold the sequence of EGFP. Underlined: Nb23

SEQ ID NO: 21: Nb23ALP
QVQLQESGGGSVQVGGSLRVACAASGDTFSGYLAAWFRQAPGKGREGVAAINSKRHTTSYADSVKGRFTISKDNADNI
MYLEMNSLKPEDTAIYYCAAADAIGLAEYWSTPTLSAARYKYWGQGTQVTVSSGGGSGGGVKQSTIALALLPLLFTPV
TKARTPEMPLQTQATSREEPPRLPSKHRPGVKTQATSREEPPRLPSKHRPGVKTQATSREEPPRLPSKHRPGVKTQAT
SREEPPRLPSKHRPGVKTQATSLEVLENRAAQGDITAPGGARRLTGDQTAALRDSLSDKPAKNIILLIGDGMGDSEIT
AARNYAEGAGGFFKGIDALPLTGQYTHYALNKKTGKPDYVTDSAASATAWSTGVKTYNGALGVDIHEKDHPTILEMAK
AAGLATGNVSTAELQDATPAALVAHVTSRKCYGPSATSEKCPGNALEKGGKGSITEQLLNARADVTLGGGAKTFAETA
TAGEWQGKTLREQAQARGYQLVSDAASLNSVTEANQQKPLLGLFADGNMPVRWLGPKATYHGNIDKPAVTCTPNPQRN
DSVPTLAQMTDKAIELLSKNEKGFFLQVEGASIDKQDHAANPCGQIGETVDLDEAVQRALEFAKKEGNTLVIVTADHA
HASQIVAPDTKAPGLTQALNTKDGAVMVMSYGNSEEDSQEHTGSQLRIAAYGPHAAHHHHHH

In bold the sequence of ALP. Underlined: Nb23

REFERENCES

Carrillo-Tripp, M., Shepherd, C. M., Borelli, I. a., Venkataraman, S., Lander, G., Natarajan, P., Johnson, J. E., Brooks, C. I. and Reddy, V. S. (2009) VIPERdb2: An enhanced and web API enabled relational database for structural virology. *Nucleic Acids Res.*, 37, 436-442.

Ho, S. N., Hunt, H. D., Horton, R. M., Pullen, J. K. and Pease, L. R. (1989) Site-directed mutagenesis by overlap extension using the polymerase chain reaction. *Gene*, 77, 51-59.

Merzlyak, E. M., Goedhart, J., Shcherbo, D., et al. (2007) Bright monomeric red fluorescent protein with an extended fluorescence lifetime. *Nat. Methods*, 4, 555-557.

Muller, B. H., Lamoure, C., Le Du, M. H., Cattolico, L., Lajeunesse, E., Lemaître, F., Pearson, A., Ducancel, F., Ménez, A. and Boulain, J. C. (2001) Improving *Escherichia coli* alkaline phosphatase efficacy by additional mutations inside and outside the catalytic pocket. *Chembiochem* 2, 517-523.

Pettersen, E. F., Goddard, T. D., Huang, C. C., Couch, G. S., Greenblatt, D. M., Meng, E. C. and Ferrin, T. E. (2004) UCSF Chimera—A visualization system for exploratory research and analysis. *J. Comput. Chem.*, 25, 1605-1612.

Quacquarelli, a., Gallitelli, D., Savino, V. and Martelli, G. P. (1976) Properties of grapevine fanleaf virus. *J. Gen. Virol.*, 32, 349-360.

Reddy Chichili, V. P., Kumar, V. and Sivaraman, J. (2013) Linkers in the structural biology of protein-protein interactions. *Protein Sci.*, 22, 153-167.

Sainsbury, F., Thuenemann, E. C. and Lomonossoff, G. P. (2009) pEAQ: versatile expression vectors for easy and quick transient expression of heterologous proteins in plants. *Plant Biotechnol. J.*, 7, 682-93. Available at: (see Worldwide Website: ncbi.nlm.nih.gov/pubmed/19627561) [Accessed Mar. 15, 2012].

Schellenberger, P., Andret-Link, P., Schmitt-Keichinger, C., et al. (2010) A stretch of 11 amino acids in the betaB-betaC loop of the coat protein of grapevine fanleaf virus is essential for transmission by the nematode *Xiphinema index*. *J. Virol.*

Schellenberger, P., Demangeat, G., Lemaire, O., Ritzenthaler, C., Bergdoll, M., Oliéric, V., Sauter, C. and Lorber, B. (2011) Strategies for the crystallization of viruses: Using phase diagrams and gels to produce 3D crystals of Grapevine fanleaf virus. *J. Struct. Biol.*, 174, 344-351.

Schellenberger, P., Sauter, C., Lorber, B., et al. (2011) Structural insights into viral determinants of nematode mediated grapevine fanleaf virus transmission. *PLoS Pathog.*, 7.

Schneider, C. a, Rasband, W. S. and Eliceiri, K. W. (2012) NIH Image to ImageJ: 25 years of image analysis. *Nat. Methods*, 9, 671-675. Available at: http://dx.doi.org/10.1038/nmeth.2089.

Vigne, E., Gottula, J., Schmitt-Keichinger, C., et al. (2013) A strain-specific segment of the RNA-dependent RNA polymerase of grapevine fanleaf virus determines symptoms in *Nicotiana* species. *J. Gen. Virol.*, 94, 2803-2813.

Viry, M., Serghini, M. A., Hans, F., et al. (1993) Biologically active transcripts from cloned eDNA of genomic grapevine fanleaf nepovirus RNAs. *In Vitro*, 4207, 169-174.

Zilian, E. and Maiss, E. (2011) An optimized mRFP-based bimolecular fluorescence complementation system for the detection of protein-protein interactions in planta. *J. Virol. Methods*, 174, 158-165. Available at: http://dx.doi.org/10.1016/j.jviromet.2011.03.032.

The invention claimed is:

1. A virus-like particle comprising a nepovirus coat protein fused to a compound, wherein the compound is fused to the N-terminus of the nepovirus coat protein and the nepovirus coat protein is a grapevine fanleaf virus (GFLV) coat protein.

2. The particle of claim 1, further comprising a compound conjugated to a nepovirus coat protein by an anti-coat protein antibody or antibody derivative.

3. The particle of claim 2, wherein the antibody derivative is a nanobody or an ScFv.

4. The particle of claim 1, said particle comprising a mixture of nepovirus coat proteins fused to compounds, said mixture comprising a nepovirus coat protein fused via its N-terminus to a compound and a nepovirus coat protein fused to via its C-terminus to a compound.

5. The particle of claim 1, which comprises an encaged compound fused to the N-terminus of the coat protein, and an exposed compound, conjugated to the surface of the particle by antibody-mediated attachment to a nepovirus coat protein.

6. The particle of claim 1, said particle being nucleic acid-free.

7. The particle of claim 1, wherein the coat protein comprises SEQ ID NO: 1.

8. The particle of claim 1, wherein the first compound is a therapeutic, diagnostic or imaging agent, or a tag.

9. A molecule comprising a nepovirus GFLV coat protein fused to a compound, wherein the compound is fused to the N-terminus of the nepovirus GFLV coat protein and the nepovirus GFLV coat protein comprises SEQ ID NO: 1.

10. A pharmaceutical composition comprising one or more virus-like particles of claim 1.

11. A pharmaceutical composition comprising the molecule of claim 9.

12. A method of producing virus-like particles comprising (i) providing a nepovirus GFLV coat protein comprising SEQ ID NO: 1 that is N-terminally fused to a compound, and (ii) allowing said protein, alone or in mixture with other proteins, to assemble into the virus-like particles.

13. The method of claim 12, further comprising a step (iii) of adding a reactive or active group to the virus-like particles.

14. The method of claim 12, said method comprising:
(i) providing a nepovirus GFLV coat protein comprising SEQ ID NO: 1 that is N-terminally fused to a first compound,
(ii) allowing said protein, alone or in mixture with other proteins, to assemble into virus-like particles, and
(iii) coupling the particles of (ii) to at least one second compound by antibody-mediated attachment using an anti-coat antibody, or a derivative thereof, conjugated to said second compound.

15. A nucleic acid molecule encoding a molecule of claim 9.

16. A vector comprising a nucleic acid of claim 15.

17. A recombinant host cell containing a nucleic acid of claim 15 or a vector comprising said nucleic acid.

18. The particle of claim 2, wherein the compound is a therapeutic, diagnostic or imaging agent, or a tag.

19. The particle of claim 4, wherein the compound is a therapeutic, diagnostic or imaging agent, or a tag.

\* \* \* \* \*

UNITED STATES PATENT AND TRADEMARK OFFICE
CERTIFICATE OF CORRECTION

PATENT NO. : 10,501,501 B2
APPLICATION NO. : 15/758732
DATED : December 10, 2019
INVENTOR(S) : Lorène Belval et al.

It is certified that error appears in the above-identified patent and that said Letters Patent is hereby corrected as shown below:

In the Specification

Column 16,
Line 8, "Image)" should read --ImageJ--.

Column 18,
Line 4, "Image)" should read --ImageJ--.

Column 23,
Line 5, "(Figure H c)" should read --(Figure 11c)--.

Signed and Sealed this
Sixteenth Day of June, 2020

Andrei Iancu
*Director of the United States Patent and Trademark Office*

SEQUENCE LISTING

<160> NUMBER OF SEQ ID NOS: 21

<210> SEQ ID NO 1
<211> LENGTH: 505
<212> TYPE: PRT
<213> ORGANISM: Artificial
<220> FEATURE:
<223> OTHER INFORMATION: GFLV Coat Protein

<400> SEQUENCE: 1

```
Met Gly Leu Ala Gly Arg Gly Val Ile Tyr Ile Pro Lys Asp Cys Gln
1               5                   10                  15

Ala Asn Arg Tyr Leu Gly Thr Leu Asn Ile Arg Asp Met Ile Ser Asp
            20                  25                  30

Phe Lys Gly Val Gln Tyr Glu Lys Trp Ile Thr Ala Gly Leu Val Met
        35                  40                  45

Pro Thr Phe Lys Ile Val Ile Arg Leu Pro Ala Asn Ala Phe Thr Gly
    50                  55                  60

Leu Thr Trp Val Met Ser Phe Asp Ala Tyr Asn Arg Ile Thr Ser Arg
65                  70                  75                  80

Ile Thr Ala Ser Ala Asp Pro Val Tyr Thr Leu Ser Val Pro His Trp
                85                  90                  95

Leu Ile His His Lys Leu Gly Thr Phe Ser Cys Glu Ile Asp Tyr Gly
            100                 105                 110

Glu Leu Cys Gly His Ala Met Trp Phe Lys Ser Thr Thr Phe Glu Ser
        115                 120                 125

Pro Arg Leu His Phe Thr Cys Leu Thr Gly Asn Asn Lys Glu Leu Ala
    130                 135                 140

Ala Asp Trp Gln Ala Val Val Glu Leu Tyr Ala Glu Leu Glu Glu Ala
145                 150                 155                 160

Thr Ser Phe Leu Gly Lys Pro Thr Leu Val Phe Asp Pro Gly Val Phe
                165                 170                 175

Asn Gly Lys Phe Gln Phe Leu Thr Cys Pro Pro Ile Phe Phe Asp Leu
            180                 185                 190

Thr Ala Val Thr Ala Leu Arg Ser Ala Gly Leu Thr Leu Gly Gln Val
        195                 200                 205

Pro Met Val Gly Thr Thr Lys Val Tyr Asn Leu Asn Ser Thr Leu Val
    210                 215                 220

Ser Cys Val Leu Gly Met Gly Gly Thr Val Arg Gly Arg Val His Ile
225                 230                 235                 240

Cys Ala Pro Ile Phe Tyr Ser Ile Val Leu Trp Val Val Ser Glu Trp
                245                 250                 255

Asn Gly Thr Thr Met Asp Trp Asn Glu Leu Phe Lys Tyr Pro Gly Val
            260                 265                 270

Tyr Val Glu Glu Asp Gly Ser Phe Glu Val Lys Ile Arg Ser Pro Tyr
        275                 280                 285

His Arg Thr Pro Ala Arg Leu Leu Ala Gly Gln Ser Gln Arg Asp Met
    290                 295                 300

Ser Ser Leu Asn Phe Tyr Ala Ile Ala Gly Pro Ile Ala Pro Ser Gly
305                 310                 315                 320

Glu Thr Ala Gln Leu Pro Ile Val Val Gln Ile Asp Glu Ile Val Arg
                325                 330                 335

Pro Asp Leu Ser Leu Pro Ser Phe Glu Asp Asp Tyr Phe Val Trp Val
            340                 345                 350

Asp Phe Ser Glu Phe Thr Leu Asp Lys Glu Glu Ile Glu Ile Gly Ser
```

-continued

```
                355                 360                 365
Arg Phe Phe Asp Phe Thr Ser Asn Thr Cys Arg Val Ser Met Gly Glu
    370                 375                 380

Asn Pro Phe Ala Ala Met Ile Ala Cys His Gly Leu His Ser Gly Val
385                 390                 395                 400

Leu Asp Leu Lys Leu Gln Trp Ser Leu Asn Thr Glu Phe Gly Lys Ser
                405                 410                 415

Ser Gly Ser Val Thr Ile Thr Lys Leu Val Gly Asp Lys Ala Met Gly
            420                 425                 430

Leu Asp Gly Pro Ser His Val Phe Ala Ile Gln Lys Leu Glu Gly Thr
                435                 440                 445

Thr Glu Leu Leu Val Gly Asn Phe Ala Gly Ala Asn Pro Asn Thr Arg
            450                 455                 460

Phe Ser Leu Tyr Ser Arg Trp Met Ala Ile Lys Leu Asp Gln Ala Lys
465                 470                 475                 480

Ser Ile Lys Val Leu Arg Val Leu Cys Lys Pro Arg Pro Gly Phe Ser
                485                 490                 495

Phe Tyr Gly Arg Thr Ser Phe Pro Val
                500                 505

<210> SEQ ID NO 2
<211> LENGTH: 563
<212> TYPE: PRT
<213> ORGANISM: Artificial
<220> FEATURE:
<223> OTHER INFORMATION: TRSV Coat Protein

<400> SEQUENCE: 2

Met Gly Gly Ser Trp Gln Glu Gly Thr Glu Ala Ala Tyr Leu Gly Lys
1               5                   10                  15

Val Thr Cys Ala Lys Asp Ala Lys Gly Gly Thr Leu Leu His Thr Leu
                20                  25                  30

Asp Ile Ile Lys Glu Cys Lys Ser Gln Asn Leu Leu Arg Tyr Lys Glu
            35                  40                  45

Trp Gln Arg Gln Gly Phe Leu His Gly Lys Leu Arg Leu Arg Cys Phe
50                  55                  60

Ile Pro Thr Asn Ile Phe Cys Gly His Ser Met Met Cys Ser Leu Asp
65                  70                  75                  80

Ala Phe Gly Arg Tyr Asp Ser Asn Val Leu Gly Ala Ser Phe Pro Val
                85                  90                  95

Lys Leu Ala Ser Leu Leu Pro Thr Glu Val Ile Ser Leu Ala Asp Gly
            100                 105                 110

Pro Val Val Thr Trp Thr Phe Asp Ile Gly Arg Leu Cys Gly His Gly
                115                 120                 125

Leu Tyr Tyr Ser Glu Gly Ala Tyr Ala Arg Pro Lys Ile Tyr Phe Leu
        130                 135                 140

Val Leu Ser Asp Asn Asp Val Pro Ala Glu Ala Asp Trp Gln Phe Thr
145                 150                 155                 160

Tyr Gln Leu Leu Phe Glu Asp His Thr Phe Ser Asn Ser Phe Gly Ala
                165                 170                 175

Val Pro Phe Ile Thr Leu Pro His Ile Phe Asn Arg Leu Asp Ile Gly
            180                 185                 190

Tyr Trp Arg Gly Pro Thr Glu Ile Asp Leu Thr Ser Thr Pro Ala Pro
        195                 200                 205

Asn Ala Tyr Arg Leu Leu Phe Gly Leu Ser Thr Val Ile Ser Gly Asn
```

```
                210                 215                 220
Met Ser Thr Leu Asn Ala Asn Gln Ala Leu Leu Arg Phe Phe Gln Gly
225                 230                 235                 240

Ser Asn Gly Thr Leu His Gly Arg Ile Lys Lys Ile Gly Thr Ala Leu
                245                 250                 255

Thr Thr Cys Ser Leu Leu Leu Ser Leu Arg His Lys Asp Ala Ser Leu
                260                 265                 270

Thr Leu Glu Thr Ala Tyr Gln Arg Pro His Tyr Ile Leu Ala Asp Gly
                275                 280                 285

Gln Gly Ala Phe Ser Leu Pro Ile Ser Thr Pro His Ala Ala Thr Ser
                290                 295                 300

Phe Leu Glu Asp Met Leu Arg Leu Glu Ile Phe Ala Ile Ala Gly Pro
305                 310                 315                 320

Phe Ser Pro Lys Asp Asn Lys Ala Lys Tyr Gln Phe Met Cys Tyr Phe
                325                 330                 335

Asp His Ile Glu Leu Val Glu Gly Val Pro Arg Thr Ile Ala Gly Glu
                340                 345                 350

Gln Gln Phe Asn Trp Cys Ser Phe Arg Asn Phe Lys Ile Asp Asp Trp
                355                 360                 365

Lys Phe Glu Trp Pro Ala Arg Leu Pro Asp Ile Leu Asp Asp Lys Ser
                370                 375                 380

Glu Val Leu Leu Arg Gln His Pro Leu Ser Leu Leu Ile Ser Ser Thr
385                 390                 395                 400

Gly Phe Phe Thr Gly Arg Ala Ile Phe Val Phe Gln Trp Gly Leu Asn
                405                 410                 415

Thr Thr Ala Gly Asn Met Lys Gly Ser Phe Ser Ala Arg Leu Ala Phe
                420                 425                 430

Gly Lys Gly Val Glu Glu Ile Glu Gln Thr Ser Thr Val Gln Pro Leu
                435                 440                 445

Val Gly Ala Cys Glu Ala Arg Ile Pro Val Glu Phe Lys Thr Tyr Thr
450                 455                 460

Gly Tyr Thr Thr Ser Gly Pro Pro Gly Ser Met Glu Pro Tyr Ile Tyr
465                 470                 475                 480

Val Arg Leu Thr Gln Ala Lys Leu Val Asp Arg Leu Ser Val Asn Val
                485                 490                 495

Ile Leu Gln Glu Gly Phe Ser Phe Tyr Gly Pro Ser Val Lys His Phe
                500                 505                 510

Lys Lys Glu Val Gly Thr Pro Ser Ala Thr Leu Gly Thr Asn Asn Pro
                515                 520                 525

Val Gly Arg Pro Pro Glu Asn Val Asp Thr Gly Pro Gly Gly Gln
                530                 535                 540

Tyr Ala Ala Ala Leu Gln Ala Ala Gln Gln Ala Gly Lys Asn Pro Phe
545                 550                 555                 560

Gly Arg Gly

<210> SEQ ID NO 3
<211> LENGTH: 506
<212> TYPE: PRT
<213> ORGANISM: Artificial
<220> FEATURE:
<223> OTHER INFORMATION: ArMV Coat Protein

<400> SEQUENCE: 3

Met Gly Leu Ala Gly Arg Gly Ser Val Gln Val Pro Lys Asp Cys Gln
1               5                   10                  15
```

```
Ala Gly Arg Tyr Leu Lys Thr Leu Asp Leu Arg Asp Met Val Ser Gly
            20                  25                  30

Phe Ser Gly Ile Gln Tyr Glu Lys Trp Ile Thr Ala Gly Leu Val Met
        35                  40                  45

Pro Asp Phe Lys Val Val Ile Arg Tyr Pro Ala Asn Ala Phe Thr Gly
50                  55                  60

Ile Thr Trp Val Met Ser Phe Asp Ala Tyr Asn Arg Ile Thr Ser Ser
65                  70                  75                  80

Ile Thr Thr Thr Ala Ser Pro Ala Tyr Thr Leu Ser Val Pro His Trp
                85                  90                  95

Leu Leu His His Lys Asn Gly Thr Thr Ser Cys Asp Ile Asp Tyr Gly
            100                 105                 110

Glu Leu Cys Gly His Ala Met Trp Phe Asn Ala Thr Thr Phe Glu Ser
        115                 120                 125

Pro Lys Leu His Phe Thr Cys Leu Thr Gly Asn Asn Lys Glu Leu Ala
    130                 135                 140

Ala Asp Trp Glu Phe Val Val Glu Leu Tyr Ala Glu Phe Glu Ala Ala
145                 150                 155                 160

Lys Thr Phe Leu Gly Arg Pro Asn Phe Val Tyr Ser Ala Asp Ala Phe
                165                 170                 175

Asn Gly Ser Phe Lys Phe Leu Thr Ile Pro Pro Leu Glu Tyr Asp Leu
            180                 185                 190

Ser Thr Thr Ser Ala Tyr Lys Ser Val Ser Leu Leu Gly Gln Thr
        195                 200                 205

Leu Ile Asp Gly Thr His Lys Val Tyr Asn Tyr Asn Thr Leu Leu
    210                 215                 220

Ser Tyr Tyr Leu Gly Ile Gly Gly Val Val Lys Gly Arg Val His Ile
225                 230                 235                 240

Cys Ser Pro Cys Thr Tyr Gly Ile Val Leu Arg Val Val Ser Glu Trp
                245                 250                 255

Asn Gly Val Thr Asn Asn Trp Asn Gln Leu Phe Lys Tyr Pro Gly Cys
            260                 265                 270

Tyr Ile Gly Glu Asp Gly Asn Phe Glu Ile Glu Ile Arg Ser Pro Tyr
        275                 280                 285

His Arg Thr Pro Leu Arg Leu Leu Asp Ala Gln Ala Ala Ser Ala Phe
    290                 295                 300

Thr Ser Thr Leu Asn Phe Tyr Ala Ile Ser Gly Pro Ile Ala Pro Ser
305                 310                 315                 320

Gly Glu Thr Ala Lys Met Pro Val Val Val Gln Ile Asp Glu Ile Ala
                325                 330                 335

Leu Pro Asp Leu Ser Val Pro Ser Phe Pro Asn Asp Tyr Phe Leu Trp
            340                 345                 350

Val Asp Phe Ser Ala Phe Thr Val Asp Ala Glu Glu Tyr Val Ile Gly
        355                 360                 365

Ser Arg Phe Phe Asp Ile Ser Ser Thr Thr Ser Thr Val His Leu Gly
    370                 375                 380

Asp Asn Pro Phe Ala His Met Ile Ala Cys His Gly Leu His Gly
385                 390                 395                 400

Ile Leu Asp Leu Lys Leu Met Trp Asp Leu Glu Gly Glu Phe Gly Lys
                405                 410                 415

Ser Ser Gly Gly Val Thr Ile Thr Lys Leu Cys Gly Asp Lys Ala Thr
            420                 425                 430
```

```
Gly Met Asp Gly Ala Ser Arg Val Cys Ala Leu Gln Asn Met Gly Cys
            435                 440                 445

Glu Thr Glu Leu Tyr Ile Gly Asn Phe Ala Gly Ala Asn Pro Asn Ser
    450                 455                 460

Ala Leu Ser Leu Tyr Ser Arg Trp Leu Ala Ile Lys Leu Asp Lys Ala
465                 470                 475                 480

Arg Ser Met Lys Met Leu Arg Ile Leu Cys Lys Pro Arg Gly Asn Phe
                485                 490                 495

Glu Phe Tyr Gly Arg Thr Cys Phe Arg Val
            500                 505

<210> SEQ ID NO 4
<211> LENGTH: 514
<212> TYPE: PRT
<213> ORGANISM: Artificial
<220> FEATURE:
<223> OTHER INFORMATION: TRSV2 Coat Protein

<400> SEQUENCE: 4

Met Ala Val Thr Val Pro Asp Pro Thr Cys Cys Gly Thr Leu Ser
1               5                   10                  15

Phe Lys Val Pro Lys Asp Ala Lys Lys Gly Lys His Leu Gly Thr Phe
                20                  25                  30

Asp Ile Arg Gln Ala Ile Met Glu Tyr Gly Gly Leu His Ser Gln Glu
            35                  40                  45

Trp Cys Ala Lys Gly Ile Val Asn Pro Thr Phe Thr Val Arg Met His
    50                  55                  60

Ala Pro Arg Asn Ala Phe Ala Gly Leu Ser Ile Ala Cys Thr Phe Asp
65                  70                  75                  80

Asp Tyr Lys Arg Ile Asp Leu Pro Ala Leu Gly Asn Glu Cys Pro Pro
                85                  90                  95

Ser Glu Met Phe Glu Leu Pro Thr Lys Val Phe Met Leu Lys Asp Ala
            100                 105                 110

Asp Val His Glu Trp Gln Phe Asn Tyr Gly Glu Leu Thr Gly His Gly
        115                 120                 125

Leu Cys Asn Trp Ala Asn Val Val Thr Gln Pro Thr Leu Tyr Phe Phe
    130                 135                 140

Val Ala Ser Thr Asn Gln Val Thr Met Ala Ala Asp Trp Gln Cys Ile
145                 150                 155                 160

Val Thr Met His Val Asp Met Gly Pro Val Ile Asp Arg Phe Glu Leu
                165                 170                 175

Val Pro Thr Met Thr Trp Pro Ile Gln Leu Gly Asp Thr Phe Ala Ile
            180                 185                 190

Asp Arg Tyr Tyr Glu Ala Lys Glu Ile Lys Leu Asp Gly Ser Thr Ser
        195                 200                 205

Met Leu Ser Ile Ser Tyr Asn Phe Gly Gly Pro Val Lys His Ser Lys
    210                 215                 220

Lys His Ala Ile Ser Tyr Ser Arg Ala Val Met Ser Arg Asn Leu Gly
225                 230                 235                 240

Trp Ser Gly Thr Ile Ser Gly Ser Val Lys Ser Val Ser Ser Leu Phe
                245                 250                 255

Cys Thr Ala Ser Phe Val Ile Phe Pro Trp Glu His Glu Ala Pro Pro
            260                 265                 270

Thr Leu Arg Gln Val Leu Trp Gly Pro His Gln Ile Met His Gly Asp
        275                 280                 285
```

-continued

```
Gly Gln Phe Glu Ile Ala Ile Lys Thr Arg Leu His Ser Ala Ala Thr
    290                 295                 300

Thr Glu Glu Gly Phe Gly Arg Leu Gly Ile Leu Pro Leu Ser Gly Pro
305                 310                 315                 320

Ile Ala Pro Asp Ala His Val Gly Ser Tyr Glu Phe Ile Val His Ile
                325                 330                 335

Asp Thr Trp Arg Pro Asp Ser Gln Val His Pro Pro Met Phe Ser Ser
            340                 345                 350

Ala Glu Leu Tyr Asn Trp Phe Thr Leu Thr Asn Leu Lys Pro Asp Ala
        355                 360                 365

Asn Thr Gly Val Val Asn Phe Asp Ile Pro Gly Tyr Ile His Asp Phe
370                 375                 380

Ala Ser Lys Asp Ala Thr Val Thr Leu Ala Ser Asn Pro Leu Ser Trp
385                 390                 395                 400

Leu Val Ala Ala Thr Gly Trp His Tyr Gly Glu Val Asp Leu Cys Ile
                405                 410                 415

Ser Trp Pro Arg Ser Lys Gln Ala Gln Ala Gln Glu Gly Ser Val Ser
            420                 425                 430

Ile Thr Thr Asn Tyr Arg Asp Trp Gly Ala Tyr Trp Gln Gly Gln Ala
        435                 440                 445

Arg Ile Tyr Asp Leu Arg Thr Glu Ala Glu Ile Pro Ile Phe Leu
450                 455                 460

Gly Ser Tyr Ala Gly Ala Thr Pro Ser Gly Ala Leu Gly Lys Gln Asn
465                 470                 475                 480

Tyr Val Arg Ile Ser Ile Val Asn Ala Lys Asp Ile Val Ala Leu Arg
                485                 490                 495

Val Cys Leu Arg Pro Lys Ser Ile Lys Phe Trp Gly Arg Ser Ala Thr
            500                 505                 510

Leu Phe
```

<210> SEQ ID NO 5
<211> LENGTH: 565
<212> TYPE: PRT
<213> ORGANISM: Artificial
<220> FEATURE:
<223> OTHER INFORMATION: CNSV Coat Protein

<400> SEQUENCE: 5

```
Met Ser Ala Glu Asn Phe Val Phe Thr Gln Leu Ile Thr Val Pro Ala
1               5                   10                  15

Ala Ser Thr Lys Gly Asn Val Leu Ala Gly Val Asp Ile Leu Ala Asn
            20                  25                  30

Ala Arg Thr Thr Met Ser Gly Phe Tyr Met Arg Trp Leu Gln Lys Gly
        35                  40                  45

Tyr Ile Asp Thr Asn Leu Lys Leu Ile Cys His Leu Pro Arg Ala Pro
50                  55                  60

Phe Ala Gly Met Ser Phe Phe Val Leu Ile Asp Gly Thr Gly Tyr Leu
65                  70                  75                  80

Ala Lys Asp Ala Pro Thr Ser Leu Asn Glu Glu Ile Leu Ser Tyr
                85                  90                  95

Pro Leu His Leu Val Thr Thr Ser Asp Val Ser Ser Tyr Glu Phe Val
            100                 105                 110

Leu Asp Trp His Arg Tyr Ile Gly Gln Val Pro Phe Ala Glu Glu Asn
        115                 120                 125

Ala Phe Leu Arg Pro Thr Leu Phe Leu Val Ala Cys Val Ser Ser Thr
```

-continued

```
            130                 135                 140
Leu Ala Leu Ser Ala Lys Val Glu Phe Tyr Leu Glu Ala Gln Ser Val
145                 150                 155                 160

Gly Glu Glu Leu Pro Arg Thr Leu Ala Pro Ser Pro Val Leu Ser Tyr
                    165                 170                 175

Pro Phe Gln Asn Ser Phe Leu Glu Asp Leu Asp Leu Phe Leu Pro Pro
                180                 185                 190

Lys Arg Leu Thr Leu Gly Glu Arg Glu Thr Thr Ile Ile Pro Leu Ser
            195                 200                 205

Phe Ala Lys Ser Lys Lys Ser Gly Asp Ala Val Leu Tyr Ser His Ala
        210                 215                 220

Ala Ala Arg Leu Ala His Phe Gln Gly Ile Gly Gly Val Leu His Gly
225                 230                 235                 240

Val Val Tyr Leu Val Gly Ser Gln Leu Val Ala Ser Gln Ser Arg Ile
                245                 250                 255

Ser Met Trp Ser Lys Glu Gln His Ile Gln His Gln Ala Val Asn Val
                260                 265                 270

His Val Asp Thr Asp Thr Gly Val Ala Phe Asp Leu Pro Ile Lys Asp
            275                 280                 285

Ala Phe Tyr Ala Ser Ser Val Tyr Gly Asp Ser Gly Ala Val Ile Gln
        290                 295                 300

Val Thr Cys Leu Cys Ser Pro Met Ser Pro Asn Ala Ile Lys Ala Pro
305                 310                 315                 320

Phe Asp Met Ile Phe Lys Ile Arg Gly Phe Thr Pro Asp Ala Pro Met
                325                 330                 335

Cys Arg Thr Ile Asn Phe Thr Gln Arg Phe Gly Trp Phe Ala Val Glu
                340                 345                 350

Pro Thr Thr Ser Thr Gly Ala Ile Lys Leu Lys Ile Trp Pro Val Ser
            355                 360                 365

Asn His Leu Glu Ser Glu Asp Met Lys Val Thr Gly Tyr Thr Asn Ala
        370                 375                 380

Phe Leu Gln Met Cys Gln Thr Ser Thr Met His Phe Gly Ser Val Ile
385                 390                 395                 400

Ile His Phe Ser Trp Thr Leu Phe Gly Gly Thr Thr Asn Ala Ala Thr
                405                 410                 415

Ala Gly Gly Val Val Thr Ile Ala Glu Gly Phe Gly Pro Glu Glu Glu
                420                 425                 430

Asn Phe Arg Gly His Cys Arg Asn Leu Ser Ile Tyr Glu Gly Arg Ala
            435                 440                 445

Thr Val Pro Leu Glu Leu Gly Thr Phe Ala Gly Pro Thr Pro Leu Lys
        450                 455                 460

Lys Leu Asp Phe Lys Tyr Arg Asn Trp Ile Arg Phe Thr Thr Pro Lys
465                 470                 475                 480

Gly Arg Asn Ile Ser Ser Ile Phe Cys Ala Ile Glu Val Leu Pro Gly
                485                 490                 495

Phe Ser Phe Tyr Gly Arg Thr Gly Ser Pro Arg Leu Ser Val Val Gly
                500                 505                 510

Thr Thr Val Pro Pro Thr Ala Asp Ala Ser Thr Ser Asn Ser Gln Gly
            515                 520                 525

Gly Asp Met Lys Ile Leu Glu Ile Asn Ile Leu Leu Pro Trp Ala Gly
        530                 535                 540

Gly Glu Asp Glu Ala Arg Val Gln Asp Gln Ala Pro Leu Gly Leu Met
545                 550                 555                 560
```

```
Phe Leu Gly Ile Ser
                565

<210> SEQ ID NO 6
<211> LENGTH: 508
<212> TYPE: PRT
<213> ORGANISM: Artificial
<220> FEATURE:
<223> OTHER INFORMATION: GBLV Coat Protein

<400> SEQUENCE: 6

Met Gly Trp Cys Pro Lys Asp Ala Thr Ala Gly Arg Val Leu Glu Ala
1               5                   10                  15

Ile Asn Leu Arg Glu Glu Ile Ala Thr Gly Asp Asn Leu Val Lys Tyr
            20                  25                  30

Asp Trp Leu Ala Lys Gly Met Ile Glu Pro Asp Met Ser Val Arg Leu
        35                  40                  45

Thr Val Gly Gln Asn Pro Phe Val Gly Ile Ser Ile Gly Val Cys Cys
    50                  55                  60

Asp Phe Ser Gly Arg Leu Ala Gln Tyr Tyr Asp Gly Ala Thr Ala Ile
65                  70                  75                  80

Pro Ile Glu Ile Cys Asn Gln Leu Pro Asn Phe Val Cys Pro Ile Ser
                85                  90                  95

Glu Arg Ser Val Phe Val His Lys Ile Asn Met Leu Leu Ala Gly Tyr
            100                 105                 110

Asn Leu Phe Gln Thr Gln Lys His Phe Ala Asp Pro Tyr Ile Leu Val
        115                 120                 125

Tyr Ile Ile Asp Thr Asn Thr Leu Ser Ala Ser Asp Glu Trp Gly Tyr
    130                 135                 140

Thr Ile Glu Leu Cys Val His Ser Ser Val His Thr Thr Gln Phe Ala
145                 150                 155                 160

Arg Thr Pro Phe Leu Thr Leu Pro Gly Thr Phe Asp Gly Thr Leu Pro
                165                 170                 175

Leu Asp Leu Trp Arg Gly Pro Phe Ser Phe Lys Thr Gly Lys Ser Ala
            180                 185                 190

Pro Arg Glu Glu Arg Ile Gly Ile Asn Phe Gly Ser Lys Arg Thr Tyr
        195                 200                 205

Asn Ser Gly Ala Lys Glu Phe Tyr Ser Leu Pro Ala Ala His Ile Gln
    210                 215                 220

Leu Leu Gln Ser Val Gly Gly Ile Leu His Gly Ser Val Ile Gln Thr
225                 230                 235                 240

Gly Ser Arg Ala Ile Ser Cys Glu Leu Tyr Met Ile Leu Gln Pro Asp
                245                 250                 255

Lys Thr Ala Asn Asn Leu Glu Gln Ala Val Lys Leu Pro Gly Cys Arg
            260                 265                 270

Val Pro Thr Gly Gly Gly Pro Phe Ser Leu Arg Ile Gln Ser Ala Phe
        275                 280                 285

Leu Arg Ser Gln Ile Tyr Glu Thr Gly Val Gln Leu Val Ile Tyr Ala
    290                 295                 300

Leu Gly Gly Pro Leu Gly Ala Ala Thr Ile Ser Ala Pro Tyr Gln Tyr
305                 310                 315                 320

Met Val His Phe Ser His Ile Thr Glu Glu Gly Phe Val Pro Arg
                325                 330                 335

Pro Ile Gly Thr Ile Leu Glu Phe Asn Trp Ala Thr Leu Ala Gln Leu
            340                 345                 350
```

```
Thr Leu Lys Asp Arg Phe Gln Ile Pro Ala Arg Leu Ser Asp Leu Val
        355                 360                 365

Ile Pro Gly Val Ser Val His Met Arg Ser Asn Pro Leu Ala Ser Ile
    370                 375                 380

Ile Gly Ala Cys Gly Phe Phe Arg Gly His Val Thr Phe Ile Leu Gln
385                 390                 395                 400

Trp Ser Leu Asn Val Glu His Val Lys Pro Lys Thr Tyr Met Gln Val
                405                 410                 415

Gln Thr Cys Val Gly Thr Phe Ile Pro Ala Pro Val Lys His Ser Gln
            420                 425                 430

Ile Leu Gln Ser Trp Val Val Pro Ile Ser Gln Arg Phe Glu Leu Arg
        435                 440                 445

Val Pro Phe Asp Leu Val Asp Tyr Pro Gly Phe Asn Ser Ser Gly Gly
    450                 455                 460

Ile Gly Leu Asp His Met Gln Pro Phe Ile Asp Ile Ala Cys Gly Asp
465                 470                 475                 480

Phe Ser Gln Leu Glu Tyr Phe Asn Ile Asn Val Glu Leu Lys Pro Gly
                485                 490                 495

Phe Glu Ile Tyr Gly Arg Ser Val Thr Pro Leu Lys
            500                 505

<210> SEQ ID NO 7
<211> LENGTH: 534
<212> TYPE: PRT
<213> ORGANISM: Artificial
<220> FEATURE:
<223> OTHER INFORMATION: BRV Coat Protein

<400> SEQUENCE: 7

Met Ser Gly Leu Val Ala Asp Thr Thr Leu Ala Phe Ala Lys Met Tyr
1               5                   10                  15

Gln Cys Lys Lys Asp Ala Lys Ala Gly His Val Leu Ala Thr Ile Asp
            20                  25                  30

Ile Gln Glu Cys Val Phe Glu Asp Asn Arg Arg Val Ala Leu Asp Trp
        35                  40                  45

Leu Ala His Gly Leu Ala Ser Phe Lys Tyr Asp Leu Gln Leu Thr Val
    50                  55                  60

Asp Ser Asn Pro Phe Val Gly Val Thr Leu Gly Ile Thr Val Asp Ala
65                  70                  75                  80

Phe Asp Arg Leu Leu Pro Gln Ile Ser Asp Glu Val Ile Ala Val Pro
                85                  90                  95

Leu Ala Phe Gln Leu Pro Thr Tyr Leu Phe Pro Ile Ser Lys Lys Gly
            100                 105                 110

Thr Phe Thr Gln Thr Ile Asp Phe Ala Ala Ile Ala Gly Tyr Asn Phe
        115                 120                 125

Phe Pro His Val Ala Ala Phe Gly Arg Pro Lys Ile Ile Val Tyr Ile
    130                 135                 140

Val Ser Asp Asn Asp Leu Pro Ala Ser Asp Thr Trp Met Cys Leu Val
145                 150                 155                 160

Glu Leu His Met Thr Arg Leu Glu Ser Ser Thr Leu Ala Cys Ser Pro
                165                 170                 175

Thr Leu Val Leu Pro Gln Ala Phe Gly Gly Asp Leu Pro Leu Asp Leu
            180                 185                 190

Trp Arg Gly Pro Tyr Thr Phe Pro Leu Gly Gly Gly Thr Lys Arg Leu
        195                 200                 205
```

Ser Thr Ser Leu Asp Ile Gly Thr Ser Thr Thr Val Ser Gly Trp
    210                 215                 220

Arg Thr Val Ser Phe Pro Ala Ala Tyr Ala Leu Phe Leu Gln Gly His
225                 230                 235                 240

Gly Gly Ser Leu Val Gly Glu Val Val His Thr Gly Ser Ala Ala Val
                245                 250                 255

Ser Cys Ala Leu His Leu Cys Ile Ser Phe Gly Gly Ala Pro Pro Thr
                260                 265                 270

Leu Glu Glu Ala Leu Val Phe Pro Gly Phe Arg Leu Pro Ser Gly Glu
            275                 280                 285

Gly Lys Phe His Ile Lys Val Gln Thr Pro Tyr Gly Arg Leu Ser Thr
        290                 295                 300

Leu Thr Pro Asp Cys Ala Leu Tyr Val Tyr Leu Ala Gly Gly Pro Ile
305                 310                 315                 320

Ala Val Ala Pro Met Ser Val Pro Tyr Gln Phe Cys Ile His Leu Glu
                325                 330                 335

Arg Leu Val Asp Asp Gly Ala Pro Pro Arg Thr Ile Gly Leu Ile Arg
            340                 345                 350

Glu Phe Asn Trp Ala Thr Ile Asn Asn Phe Lys Ser Asp Asp Ile Thr
        355                 360                 365

Phe Ala Ile Pro Ala Arg Leu Ser Asp Leu Val Leu Thr Cys Gly Asp
370                 375                 380

Val Thr Met Ser Thr Asn Pro Leu Ala Leu Leu Ile Gly Ser Cys Gly
385                 390                 395                 400

Phe Phe Arg Gly Asn Leu Thr Val Val Leu Glu Trp Ala Thr Phe Leu
                405                 410                 415

Lys Ala Gly Asp Lys Glu Gly Thr Val Gln Leu Thr Thr Cys Arg Gly
            420                 425                 430

Met Ile Asn Asn Val Lys Gly Val Arg Asn Ala Ile Gln Lys Lys Val
        435                 440                 445

Val Asn Leu Ser Leu Val Gly Ser Val Ser Arg Tyr Leu Asn Val Gly
450                 455                 460

Asp Phe Thr Gly Phe Ala Gln Ser Gly Gly Gln Val Gly Tyr Asp Glu
465                 470                 475                 480

Ile Phe Leu Glu Phe Ser Thr Asn Lys Ala Lys Gln Ile Arg Tyr Leu
                485                 490                 495

Asn Ile Asn Val Glu Leu Asp Glu Asn Phe Glu Leu Tyr Gly Arg Thr
            500                 505                 510

Ile Ile Pro Leu Lys Asn Thr Ala Pro Ala Phe Ala Ser Thr Ser Ala
        515                 520                 525

Ser Ala Pro Asn Glu Ser
    530

<210> SEQ ID NO 8
<211> LENGTH: 521
<212> TYPE: PRT
<213> ORGANISM: Artificial
<220> FEATURE:
<223> OTHER INFORMATION: BRSV Coat Protein

<400> SEQUENCE: 8

Met Ala Gly Gly Ser Tyr Ala Phe Gly Glu Thr Ile Glu Leu Pro Ala
1               5                   10                  15

Thr Val Thr Pro Gly Thr Val Leu Ala Val Phe Asn Ile Phe Asp Lys
            20                  25                  30

Ile Gln Glu Thr Asn Thr Lys Val Cys Ser Lys Trp Leu Glu Gln Gly
         35                  40                  45

Tyr Val Ser Gln Asn Leu Thr Ala Ile Ser His Leu Ala Pro Asn Ala
         50                  55                  60

Phe Ser Gly Ile Ala Ile Trp Tyr Ile Phe Asp Ala Tyr Gly Lys Ile
 65                  70                  75                  80

Pro Gly Asp Val Thr Thr Thr Phe Glu Leu Glu Met Ala Arg Ser Phe
                     85                  90                  95

Asp Pro His Val Gln Val Leu Arg Asp Val Ser Thr Ser Thr Trp Val
                 100                 105                 110

Ile Asp Phe His Lys Ile Cys Gly Gln Thr Leu Asn Phe Ser Gly Gln
                 115                 120                 125

Gly Tyr Cys Val Pro Lys Ile Trp Val Ile Ala Ala Ser Thr Phe Gln
         130                 135                 140

Leu Ala Arg Ser Thr Ala Thr Lys Phe Arg Leu Glu Phe Tyr Thr Arg
145                 150                 155                 160

Gly Glu Lys Leu Val Arg Gly Leu Ala Glu Gln Pro Leu Ser Tyr Pro
                 165                 170                 175

Ile Glu Ala Arg His Leu Thr Asp Leu Asn Leu Met Leu Ala Pro Lys
                 180                 185                 190

Gln Ile Ala Val Gly Thr Tyr Ala Met Ile Thr Phe Pro Val Ser Leu
         195                 200                 205

Ala Ala Lys Leu Gln Ser Thr Ser Gly Arg Thr Ala Tyr Ser Tyr Ala
         210                 215                 220

Ala Gly Leu Leu Ser His Phe Leu Gly Val Gly Gly Thr Ile His Phe
225                 230                 235                 240

Val Val Arg Thr Thr Ser Ser Ala Phe Val Thr Ser Lys Leu Arg Ile
                 245                 250                 255

Ala Leu Trp Gly Thr Val Pro Glu Thr Asp Gln Leu Ala Gln Met Pro
                 260                 265                 270

His Val Asp Val Glu Val Asn Val Asp Ala Ser Leu Gln Ile Gln Ser
         275                 280                 285

Pro Phe Phe Ser Thr Ala Asn Phe Gly Asn Ser Gly Ser Ala Phe Tyr
         290                 295                 300

Val Ser Thr Leu Cys Ala Pro Met Ala Pro Glu Thr Val Glu Thr Gly
305                 310                 315                 320

Ser Glu Tyr Tyr Ile Gln Ile Lys Gly Ile Glu Ala Asn Pro Gly Leu
                 325                 330                 335

Cys Arg Glu Ile Asn Tyr Lys Gln Arg Phe Ala Trp Cys Leu Leu Glu
                 340                 345                 350

Cys Leu Asp Asn Ser Lys Ala Ser Pro Ile Lys Val Lys Ile Pro Ser
         355                 360                 365

Arg Ile Gly Asn Leu Ser Ser Lys His Val Lys Val Thr Asn Phe Val
370                 375                 380

Asn Ala Leu Ala Ile Leu Cys Ala Thr Thr Gly Met His His Gly Asn
385                 390                 395                 400

Cys Thr Ile His Phe Ser Trp Leu Trp His Pro Ala Glu Leu Gly Lys
                 405                 410                 415

Gln Leu Gly Arg Leu Lys Phe Val Gln Gly Met Gly Ile Asn Asn Glu
                 420                 425                 430

His Ile Gly Asp Thr Met Cys Tyr Asn Ser Leu Ser Asn Thr His Ser
                 435                 440                 445

```
Val Pro Phe Gln Phe Gly Ser Phe Ala Gly Pro Ile Thr Ser Gly Gly
    450                 455                 460

Lys Ala Asp Glu Ala Glu Asn Trp Ile Glu Ile Gln Ser Pro Asp Phe
465                 470                 475                 480

Ser Trp Val Ala Ser Leu His Val Ser Ile Glu Val His Glu Gly Phe
                485                 490                 495

Lys Phe Tyr Gly Arg Ser Ala Gly Pro Leu Thr Ile Pro Ala Thr Val
            500                 505                 510

Ala Asp Val Ser Ala Val Ser Gly Ser
            515                 520
```

<210> SEQ ID NO 9
<211> LENGTH: 745
<212> TYPE: PRT
<213> ORGANISM: Artificial
<220> FEATURE:
<223> OTHER INFORMATION: CPTR

<400> SEQUENCE: 9

```
Met Gly Leu Ala Gly Arg Gly Val Ile Tyr Ile Pro Lys Asp Cys Gln
1               5                   10                  15

Ala Asn Arg Tyr Leu Gly Thr Leu Asn Ile Arg Asp Met Ile Ser Asp
            20                  25                  30

Phe Lys Gly Val Gln Tyr Glu Lys Trp Ile Thr Ala Gly Leu Val Met
        35                  40                  45

Pro Thr Phe Lys Ile Val Ile Arg Leu Pro Ala Asn Ala Phe Thr Gly
    50                  55                  60

Leu Thr Trp Val Met Ser Phe Asp Ala Tyr Asn Arg Ile Thr Ser Arg
65                  70                  75                  80

Ile Thr Ala Ser Ala Asp Pro Val Tyr Thr Leu Ser Val Pro His Trp
                85                  90                  95

Leu Ile His His Lys Leu Gly Thr Phe Ser Cys Glu Ile Asp Tyr Gly
            100                 105                 110

Glu Leu Cys Gly His Ala Met Trp Phe Lys Ser Thr Thr Phe Glu Ser
        115                 120                 125

Pro Arg Leu His Phe Thr Cys Leu Thr Gly Asn Asn Lys Glu Leu Ala
    130                 135                 140

Ala Asp Trp Gln Ala Val Val Glu Leu Tyr Ala Glu Leu Glu Glu Ala
145                 150                 155                 160

Thr Ser Phe Leu Gly Lys Pro Thr Leu Val Phe Asp Pro Gly Val Phe
                165                 170                 175

Asn Gly Lys Phe Gln Phe Leu Thr Cys Pro Pro Ile Phe Phe Asp Leu
            180                 185                 190

Thr Ala Val Thr Ala Leu Arg Ser Ala Gly Leu Thr Leu Gly Gln Val
        195                 200                 205

Pro Met Val Gly Thr Thr Lys Val Tyr Asn Leu Asn Ser Thr Leu Val
    210                 215                 220

Ser Cys Val Leu Gly Met Gly Gly Thr Val Arg Gly Arg Val His Ile
225                 230                 235                 240

Cys Ala Pro Ile Phe Tyr Ser Ile Val Leu Trp Val Ser Glu Trp
                245                 250                 255

Asn Gly Thr Thr Met Asp Trp Asn Glu Leu Phe Lys Tyr Pro Gly Val
            260                 265                 270

Tyr Val Glu Glu Asp Gly Ser Phe Glu Val Lys Ile Arg Ser Pro Tyr
        275                 280                 285
```

```
His Arg Thr Pro Ala Arg Leu Leu Ala Gly Gln Ser Gln Arg Asp Met
    290                 295                 300

Ser Ser Leu Asn Phe Tyr Ala Ile Ala Gly Pro Ile Ala Pro Ser Gly
305                 310                 315                 320

Glu Thr Ala Gln Leu Pro Ile Val Val Gln Ile Asp Glu Ile Val Arg
                325                 330                 335

Pro Asp Leu Ser Leu Pro Ser Phe Glu Asp Asp Tyr Phe Val Trp Val
                340                 345                 350

Asp Phe Ser Glu Phe Thr Leu Asp Lys Glu Glu Ile Glu Ile Gly Ser
        355                 360                 365

Arg Phe Phe Asp Phe Thr Ser Asn Thr Cys Arg Val Ser Met Gly Glu
370                 375                 380

Asn Pro Phe Ala Ala Met Ile Ala Cys His Gly Leu His Ser Gly Val
385                 390                 395                 400

Leu Asp Leu Lys Leu Gln Trp Ser Leu Asn Thr Glu Phe Gly Lys Ser
                405                 410                 415

Ser Gly Ser Val Thr Ile Thr Lys Leu Val Gly Asp Lys Ala Met Gly
                420                 425                 430

Leu Asp Gly Pro Ser His Val Phe Ala Ile Gln Lys Leu Glu Gly Thr
                435                 440                 445

Thr Glu Leu Leu Val Gly Asn Phe Ala Gly Ala Asn Pro Asn Thr Arg
450                 455                 460

Phe Ser Leu Tyr Ser Arg Trp Met Ala Ile Lys Leu Asp Gln Ala Lys
465                 470                 475                 480

Ser Ile Lys Val Leu Arg Val Leu Cys Lys Pro Arg Pro Gly Phe Ser
                485                 490                 495

Phe Tyr Gly Arg Thr Ser Phe Pro Val Gly Gly Ser Gly Gly Gly
                500                 505                 510

Met Ser Glu Leu Ile Lys Glu Asn Met His Met Lys Leu Tyr Met Glu
                515                 520                 525

Gly Thr Val Asn Asn His His Phe Lys Cys Thr Ser Glu Gly Glu Gly
                530                 535                 540

Lys Pro Tyr Glu Gly Thr Gln Thr Met Arg Ile Lys Val Val Glu Gly
545                 550                 555                 560

Gly Pro Leu Pro Phe Ala Phe Asp Ile Leu Ala Thr Ser Phe Met Tyr
                565                 570                 575

Gly Ser Arg Thr Phe Ile Asn His Thr Gln Gly Ile Pro Asp Phe Phe
                580                 585                 590

Lys Gln Ser Phe Pro Glu Gly Phe Thr Trp Glu Arg Val Thr Thr Tyr
                595                 600                 605

Glu Asp Gly Gly Val Leu Thr Ala Thr Gln Asp Thr Ser Leu Gln Asp
610                 615                 620

Gly Cys Leu Ile Tyr Asn Val Lys Ile Arg Gly Val Asn Phe Pro Ser
625                 630                 635                 640

Asn Gly Pro Val Met Gln Lys Lys Thr Leu Gly Trp Glu Ala Asn Thr
                645                 650                 655

Glu Met Leu Tyr Pro Ala Asp Gly Gly Leu Glu Gly Arg Ser Asp Met
                660                 665                 670

Ala Leu Lys Leu Val Gly Gly His Leu Ile Cys Asn Phe Lys Thr
                675                 680                 685

Thr Tyr Arg Ser Lys Lys Pro Ala Lys Asn Leu Lys Met Pro Gly Val
    690                 695                 700

Tyr Tyr Val Asp His Arg Leu Glu Arg Ile Lys Glu Ala Asp Lys Glu
```

```
                705                 710                 715                 720
Thr Tyr Val Glu Gln His Glu Val Ala Val Ala Arg Tyr Cys Asp Leu
                    725                 730                 735
Pro Ser Lys Leu Gly His Lys Leu Asn
                740                 745

<210> SEQ ID NO 10
<211> LENGTH: 744
<212> TYPE: PRT
<213> ORGANISM: Artificial
<220> FEATURE:
<223> OTHER INFORMATION: TRCP

<400> SEQUENCE: 10

Met Ser Glu Leu Ile Lys Glu Asn Met His Met Lys Leu Tyr Met Glu
1               5                   10                  15
Gly Thr Val Asn Asn His His Phe Lys Cys Thr Ser Glu Gly Glu Gly
                20                  25                  30
Lys Pro Tyr Glu Gly Thr Gln Thr Met Arg Ile Lys Val Val Glu Gly
            35                  40                  45
Gly Pro Leu Pro Phe Ala Phe Asp Ile Leu Ala Thr Ser Phe Met Tyr
        50                  55                  60
Gly Ser Arg Thr Phe Ile Asn His Thr Gln Gly Ile Pro Asp Phe Phe
65                  70                  75                  80
Lys Gln Ser Phe Pro Glu Gly Phe Thr Trp Glu Arg Val Thr Thr Tyr
                85                  90                  95
Glu Asp Gly Gly Val Leu Thr Ala Thr Gln Asp Thr Ser Leu Gln Asp
            100                 105                 110
Gly Cys Leu Ile Tyr Asn Val Lys Ile Arg Gly Val Asn Phe Pro Ser
        115                 120                 125
Asn Gly Pro Val Met Gln Lys Lys Thr Leu Gly Trp Glu Ala Asn Thr
130                 135                 140
Glu Met Leu Tyr Pro Ala Asp Gly Gly Leu Glu Gly Arg Ser Asp Met
145                 150                 155                 160
Ala Leu Lys Leu Val Gly Gly Gly His Leu Ile Cys Asn Phe Lys Thr
                165                 170                 175
Thr Tyr Arg Ser Lys Lys Pro Ala Lys Asn Leu Lys Met Pro Gly Val
            180                 185                 190
Tyr Tyr Val Asp His Arg Leu Glu Arg Ile Lys Glu Ala Asp Lys Glu
        195                 200                 205
Thr Tyr Val Glu Gln His Glu Val Ala Val Ala Arg Tyr Cys Asp Leu
    210                 215                 220
Pro Ser Lys Leu Gly His Lys Leu Asn Gly Gly Ser Gly Gly Gly
225                 230                 235                 240
Gly Leu Ala Gly Arg Gly Val Ile Tyr Ile Pro Lys Asp Cys Gln Ala
                245                 250                 255
Asn Arg Tyr Leu Gly Thr Leu Asn Ile Arg Asp Met Ile Ser Asp Phe
            260                 265                 270
Lys Gly Val Gln Tyr Glu Lys Trp Ile Thr Ala Gly Leu Val Met Pro
        275                 280                 285
Thr Phe Lys Ile Val Ile Arg Leu Pro Ala Asn Ala Phe Thr Gly Leu
    290                 295                 300
Thr Trp Val Met Ser Phe Asp Ala Tyr Asn Arg Ile Thr Ser Arg Ile
305                 310                 315                 320
Thr Ala Ser Ala Asp Pro Val Tyr Thr Leu Ser Val Pro His Trp Leu
```

```
                        325                 330                 335
Ile His His Lys Leu Gly Thr Phe Ser Cys Glu Ile Asp Tyr Gly Glu
                340                 345                 350

Leu Cys Gly His Ala Met Trp Phe Lys Ser Thr Thr Phe Glu Ser Pro
            355                 360                 365

Arg Leu His Phe Thr Cys Leu Thr Gly Asn Asn Lys Glu Leu Ala Ala
        370                 375                 380

Asp Trp Gln Ala Val Val Glu Leu Tyr Ala Glu Leu Glu Glu Ala Thr
385                 390                 395                 400

Ser Phe Leu Gly Lys Pro Thr Leu Val Phe Asp Pro Gly Val Phe Asn
                405                 410                 415

Gly Lys Phe Gln Phe Leu Thr Cys Pro Pro Ile Phe Phe Asp Leu Thr
            420                 425                 430

Ala Val Thr Ala Leu Arg Ser Ala Gly Leu Thr Leu Gly Gln Val Pro
        435                 440                 445

Met Val Gly Thr Thr Lys Val Tyr Asn Leu Asn Ser Thr Leu Val Ser
    450                 455                 460

Cys Val Leu Gly Met Gly Gly Thr Val Arg Gly Arg Val His Ile Cys
465                 470                 475                 480

Ala Pro Ile Phe Tyr Ser Ile Val Leu Trp Val Val Ser Glu Trp Asn
                485                 490                 495

Gly Thr Thr Met Asp Trp Asn Glu Leu Phe Lys Tyr Pro Gly Val Tyr
            500                 505                 510

Val Glu Glu Asp Gly Ser Phe Glu Val Lys Ile Arg Ser Pro Tyr His
        515                 520                 525

Arg Thr Pro Ala Arg Leu Leu Ala Gly Gln Ser Gln Arg Asp Met Ser
    530                 535                 540

Ser Leu Asn Phe Tyr Ala Ile Ala Gly Pro Ile Ala Pro Ser Gly Glu
545                 550                 555                 560

Thr Ala Gln Leu Pro Ile Val Val Gln Ile Asp Glu Ile Val Arg Pro
                565                 570                 575

Asp Leu Ser Leu Pro Ser Phe Glu Asp Asp Tyr Phe Val Trp Val Asp
            580                 585                 590

Phe Ser Glu Phe Thr Leu Asp Lys Glu Glu Ile Glu Ile Gly Ser Arg
        595                 600                 605

Phe Phe Asp Phe Thr Ser Asn Thr Cys Arg Val Ser Met Gly Glu Asn
    610                 615                 620

Pro Phe Ala Ala Met Ile Ala Cys His Gly Leu His Ser Gly Val Leu
625                 630                 635                 640

Asp Leu Lys Leu Gln Trp Ser Leu Asn Thr Glu Phe Gly Lys Ser Ser
                645                 650                 655

Gly Ser Val Thr Ile Thr Lys Leu Val Gly Asp Lys Ala Met Gly Leu
            660                 665                 670

Asp Gly Pro Ser His Val Phe Ala Ile Gln Lys Leu Glu Gly Thr Thr
        675                 680                 685

Glu Leu Leu Val Gly Asn Phe Ala Gly Ala Asn Pro Asn Thr Arg Phe
    690                 695                 700

Ser Leu Tyr Ser Arg Trp Met Ala Ile Lys Leu Asp Gln Ala Lys Ser
705                 710                 715                 720

Ile Lys Val Leu Arg Val Leu Cys Lys Pro Arg Pro Gly Phe Ser Phe
                725                 730                 735

Tyr Gly Arg Thr Ser Phe Pro Val
            740
```

```
<210> SEQ ID NO 11
<211> LENGTH: 761
<212> TYPE: PRT
<213> ORGANISM: Artificial
<220> FEATURE:
<223> OTHER INFORMATION: CPEG

<400> SEQUENCE: 11
```

| | | | | | | | | | | | | | | |
|---|---|---|---|---|---|---|---|---|---|---|---|---|---|---|
| Met | Gly | Leu | Ala | Gly | Arg | Gly | Val | Ile | Tyr | Ile | Pro | Lys | Asp | Cys | Gln |
| 1 | | | | 5 | | | | | 10 | | | | | 15 | |

| Ala | Asn | Arg | Tyr | Leu | Gly | Thr | Leu | Asn | Ile | Arg | Asp | Met | Ile | Ser | Asp |
|---|---|---|---|---|---|---|---|---|---|---|---|---|---|---|---|
| | | | 20 | | | | 25 | | | | 30 | | | | |

| Phe | Lys | Gly | Val | Gln | Tyr | Glu | Lys | Trp | Ile | Thr | Ala | Gly | Leu | Val | Met |
|---|---|---|---|---|---|---|---|---|---|---|---|---|---|---|---|
| | 35 | | | | 40 | | | | | 45 | | | | | |

| Pro | Thr | Phe | Lys | Ile | Val | Ile | Arg | Leu | Pro | Ala | Asn | Ala | Phe | Thr | Gly |
|---|---|---|---|---|---|---|---|---|---|---|---|---|---|---|---|
| | 50 | | | | 55 | | | | | 60 | | | | | |

| Leu | Thr | Trp | Val | Met | Ser | Phe | Asp | Ala | Tyr | Asn | Arg | Ile | Thr | Ser | Arg |
|---|---|---|---|---|---|---|---|---|---|---|---|---|---|---|---|
| 65 | | | | | 70 | | | | | 75 | | | | | 80 |

| Ile | Thr | Ala | Ser | Ala | Asp | Pro | Val | Tyr | Thr | Leu | Ser | Val | Pro | His | Trp |
|---|---|---|---|---|---|---|---|---|---|---|---|---|---|---|---|
| | | | | 85 | | | | | 90 | | | | | 95 | |

| Leu | Ile | His | His | Lys | Leu | Gly | Thr | Phe | Ser | Cys | Glu | Ile | Asp | Tyr | Gly |
|---|---|---|---|---|---|---|---|---|---|---|---|---|---|---|---|
| | | | 100 | | | | | 105 | | | | | 110 | | |

| Glu | Leu | Cys | Gly | His | Ala | Met | Trp | Phe | Lys | Ser | Thr | Thr | Phe | Glu | Ser |
|---|---|---|---|---|---|---|---|---|---|---|---|---|---|---|---|
| | | 115 | | | | | 120 | | | | | 125 | | | |

| Pro | Arg | Leu | His | Phe | Thr | Cys | Leu | Thr | Gly | Asn | Asn | Lys | Glu | Leu | Ala |
|---|---|---|---|---|---|---|---|---|---|---|---|---|---|---|---|
| | 130 | | | | | 135 | | | | | 140 | | | | |

| Ala | Asp | Trp | Gln | Ala | Val | Val | Glu | Leu | Tyr | Ala | Glu | Leu | Glu | Glu | Ala |
|---|---|---|---|---|---|---|---|---|---|---|---|---|---|---|---|
| 145 | | | | | 150 | | | | | 155 | | | | | 160 |

| Thr | Ser | Phe | Leu | Gly | Lys | Pro | Thr | Leu | Val | Phe | Asp | Pro | Gly | Val | Phe |
|---|---|---|---|---|---|---|---|---|---|---|---|---|---|---|---|
| | | | | 165 | | | | | 170 | | | | | 175 | |

| Asn | Gly | Lys | Phe | Gln | Phe | Leu | Thr | Cys | Pro | Pro | Ile | Phe | Phe | Asp | Leu |
|---|---|---|---|---|---|---|---|---|---|---|---|---|---|---|---|
| | | | 180 | | | | | 185 | | | | | 190 | | |

| Thr | Ala | Val | Thr | Ala | Leu | Arg | Ser | Ala | Gly | Leu | Thr | Leu | Gly | Gln | Val |
|---|---|---|---|---|---|---|---|---|---|---|---|---|---|---|---|
| | | | 195 | | | | | 200 | | | | | 205 | | |

| Pro | Met | Val | Gly | Thr | Thr | Lys | Val | Tyr | Asn | Leu | Asn | Ser | Thr | Leu | Val |
|---|---|---|---|---|---|---|---|---|---|---|---|---|---|---|---|
| | 210 | | | | | 215 | | | | | 220 | | | | |

| Ser | Cys | Val | Leu | Gly | Met | Gly | Gly | Thr | Val | Arg | Gly | Arg | Val | His | Ile |
|---|---|---|---|---|---|---|---|---|---|---|---|---|---|---|---|
| 225 | | | | | 230 | | | | | 235 | | | | | 240 |

| Cys | Ala | Pro | Ile | Phe | Tyr | Ser | Ile | Val | Leu | Trp | Val | Val | Ser | Glu | Trp |
|---|---|---|---|---|---|---|---|---|---|---|---|---|---|---|---|
| | | | | 245 | | | | | 250 | | | | | 255 | |

| Asn | Gly | Thr | Thr | Met | Asp | Trp | Asn | Glu | Leu | Phe | Lys | Tyr | Pro | Gly | Val |
|---|---|---|---|---|---|---|---|---|---|---|---|---|---|---|---|
| | | | 260 | | | | | 265 | | | | | 270 | | |

| Tyr | Val | Glu | Glu | Asp | Gly | Ser | Phe | Glu | Val | Lys | Ile | Arg | Ser | Pro | Tyr |
|---|---|---|---|---|---|---|---|---|---|---|---|---|---|---|---|
| | | 275 | | | | | 280 | | | | | 285 | | | |

| His | Arg | Thr | Pro | Ala | Arg | Leu | Leu | Ala | Gly | Gln | Ser | Gln | Arg | Asp | Met |
|---|---|---|---|---|---|---|---|---|---|---|---|---|---|---|---|
| | 290 | | | | | 295 | | | | | 300 | | | | |

| Ser | Ser | Leu | Asn | Phe | Tyr | Ala | Ile | Ala | Gly | Pro | Ile | Ala | Pro | Ser | Gly |
|---|---|---|---|---|---|---|---|---|---|---|---|---|---|---|---|
| 305 | | | | | 310 | | | | | 315 | | | | | 320 |

| Glu | Thr | Ala | Gln | Leu | Pro | Ile | Val | Val | Gln | Ile | Asp | Glu | Ile | Val | Arg |
|---|---|---|---|---|---|---|---|---|---|---|---|---|---|---|---|
| | | | | 325 | | | | | 330 | | | | | 335 | |

| Pro | Asp | Leu | Ser | Leu | Pro | Ser | Phe | Glu | Asp | Asp | Tyr | Phe | Val | Trp | Val |
|---|---|---|---|---|---|---|---|---|---|---|---|---|---|---|---|
| | | | 340 | | | | | 345 | | | | | 350 | | |

| Asp | Phe | Ser | Glu | Phe | Thr | Leu | Asp | Lys | Glu | Glu | Ile | Glu | Ile | Gly | Ser |
|---|---|---|---|---|---|---|---|---|---|---|---|---|---|---|---|
| | | 355 | | | | | 360 | | | | | 365 | | | |

```
Arg Phe Phe Asp Phe Thr Ser Asn Thr Cys Arg Val Ser Met Gly Glu
        370                 375                 380

Asn Pro Phe Ala Ala Met Ile Ala Cys His Gly Leu His Ser Gly Val
385                 390                 395                 400

Leu Asp Leu Lys Leu Gln Trp Ser Leu Asn Thr Glu Phe Gly Lys Ser
                405                 410                 415

Ser Gly Ser Val Thr Ile Thr Lys Leu Val Gly Asp Lys Ala Met Gly
                420                 425                 430

Leu Asp Gly Pro Ser His Val Phe Ala Ile Gln Lys Leu Glu Gly Thr
            435                 440                 445

Thr Glu Leu Leu Val Gly Asn Phe Ala Gly Ala Asn Pro Asn Thr Arg
    450                 455                 460

Phe Ser Leu Tyr Ser Arg Trp Met Ala Ile Lys Leu Asp Gln Ala Lys
465                 470                 475                 480

Ser Ile Lys Val Leu Arg Val Leu Cys Lys Pro Arg Pro Gly Phe Ser
                485                 490                 495

Phe Tyr Gly Arg Thr Ser Phe Pro Val Asp Pro Ala Phe Leu Tyr Lys
                500                 505                 510

Val Val Arg Ser Phe Gly Pro Ala Met Val Ser Lys Gly Glu Glu Leu
            515                 520                 525

Phe Thr Gly Val Val Pro Ile Leu Val Glu Leu Asp Gly Asp Val Asn
    530                 535                 540

Gly His Lys Phe Ser Val Ser Gly Glu Gly Glu Gly Asp Ala Thr Tyr
545                 550                 555                 560

Gly Lys Leu Thr Leu Lys Phe Ile Cys Thr Thr Gly Lys Leu Pro Val
                565                 570                 575

Pro Trp Pro Thr Leu Val Thr Thr Leu Thr Tyr Gly Val Gln Cys Phe
            580                 585                 590

Ser Arg Tyr Pro Asp His Met Lys Gln His Asp Phe Phe Lys Ser Ala
            595                 600                 605

Met Pro Glu Gly Tyr Val Gln Glu Arg Thr Ile Phe Phe Lys Asp Asp
    610                 615                 620

Gly Asn Tyr Lys Thr Arg Ala Glu Val Lys Phe Glu Gly Asp Thr Leu
625                 630                 635                 640

Val Asn Arg Ile Glu Leu Lys Gly Ile Asp Phe Lys Glu Asp Gly Asn
                645                 650                 655

Ile Leu Gly His Lys Leu Glu Tyr Asn Tyr Asn Ser His Asn Val Tyr
            660                 665                 670

Ile Met Ala Asp Lys Gln Lys Asn Gly Ile Lys Val Asn Phe Lys Ile
    675                 680                 685

Arg His Asn Ile Glu Asp Gly Ser Val Gln Leu Ala Asp His Tyr Gln
690                 695                 700

Gln Asn Thr Pro Ile Gly Asp Gly Pro Val Leu Leu Pro Asp Asn His
705                 710                 715                 720

Tyr Leu Ser Thr Gln Ser Ala Leu Ser Lys Asp Pro Asn Glu Lys Arg
                725                 730                 735

Asp His Met Val Leu Leu Glu Phe Val Thr Ala Ala Gly Ile Thr Leu
            740                 745                 750

Gly Met Asp Glu Leu Tyr Lys Thr Ser
            755                 760

<210> SEQ ID NO 12
<211> LENGTH: 231
```

```
<212> TYPE: PRT
<213> ORGANISM: Artificial
<220> FEATURE:
<223> OTHER INFORMATION: TR

<400> SEQUENCE: 12

Met Ser Glu Leu Ile Lys Glu Asn Met His Met Lys Leu Tyr Met Glu
1               5                   10                  15

Gly Thr Val Asn Asn His His Phe Lys Cys Thr Ser Glu Gly Glu Gly
                20                  25                  30

Lys Pro Tyr Glu Gly Thr Gln Thr Met Arg Ile Lys Val Val Glu Gly
            35                  40                  45

Gly Pro Leu Pro Phe Ala Phe Asp Ile Leu Ala Thr Ser Phe Met Tyr
        50                  55                  60

Gly Ser Arg Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Pro Ser
        115                 120                 125

Asn Gly Pro Val Met Gln Lys Lys Thr Leu Gly Trp Glu Ala Asn Thr
130                 135                 140

Glu Met Leu Tyr Pro Ala Asp Gly Gly Leu Glu Gly Arg Ser Asp Met
145                 150                 155                 160

Ala Leu Lys Leu Val Gly Gly His Leu Ile Cys Asn Phe Lys Thr
                165                 170                 175

Thr Tyr Arg Ser Lys Lys Pro Ala Lys Asn Leu Lys Met Pro Gly Val
            180                 185                 190

Tyr Tyr Val Asp His Arg Leu Glu Arg Ile Lys Glu Ala Asp Lys Glu
        195                 200                 205

Thr Tyr Val Glu Gln His Glu Val Ala Val Ala Arg Tyr Cys Asp Leu
    210                 215                 220

Pro Ser Lys Leu Gly His Asn
225                 230

<210> SEQ ID NO 13
<211> LENGTH: 15
<212> TYPE: PRT
<213> ORGANISM: Artificial
<220> FEATURE:
<223> OTHER INFORMATION: Linker

<400> SEQUENCE: 13

Asp Pro Ala Phe Leu Tyr Lys Val Val Arg Ser Phe Gly Pro Ala
1               5                   10                  15

<210> SEQ ID NO 14
<211> LENGTH: 131
<212> TYPE: PRT
<213> ORGANISM: Artificial
<220> FEATURE:
<223> OTHER INFORMATION: Nb126

<400> SEQUENCE: 14

Gln Val Gln Leu Gln Glu Ser Gly Gly Gly Ser Val Gln Val Gly Gly
1               5                   10                  15

Ser Leu Arg Leu Ala Cys Ala Ala Ser Gly Asp Thr Phe Ser Gly Tyr
```

```
                20                  25                  30

Leu Ala Ala Trp Phe Arg Gln Ala Pro Gly Lys Glu Arg Glu Gly Val
        35                  40                  45

Ala Ala Ile Asn Ser Val Arg His Thr Thr Ser Tyr Ala Asn Ser Val
    50                  55                  60

Lys Gly Arg Phe Thr Ile Ser Lys Asp Asn Ala Asp Asn Met Met Tyr
 65                 70                  75                  80

Leu Glu Met Asn Ser Leu Lys Pro Glu Asp Thr Ala Ile Tyr Tyr Cys
                85                  90                  95

Ala Ala Ala Asp Ala Ile Gly Leu Ala Glu Tyr Trp Ser Thr Pro Thr
            100                 105                 110

Leu Ser Ala Ala Arg Tyr Lys Tyr Trp Gly Gln Gly Thr Gln Val Thr
        115                 120                 125

Val Ser Ser
    130

<210> SEQ ID NO 15
<211> LENGTH: 131
<212> TYPE: PRT
<213> ORGANISM: Artificial
<220> FEATURE:
<223> OTHER INFORMATION: Nb101

<400> SEQUENCE: 15

Gln Val Gln Leu Gln Glu Ser Gly Gly Gly Ser Val Gln Val Gly Gly
 1               5                  10                  15

Ser Leu Arg Leu Ala Cys Ala Ala Ser Gly Asp Thr Phe Ser Gly Tyr
            20                  25                  30

Leu Ala Ala Trp Phe Arg Gln Ala Pro Gly Lys Glu Arg Glu Gly Val
        35                  40                  45

Ala Ala Ile Asn Ser Val Arg His Thr Thr Ser Tyr Ala Asp Ser Val
    50                  55                  60

Lys Gly Arg Phe Thr Ile Ser Lys Asp Asn Ala Asp Asn Met Met Tyr
 65                 70                  75                  80

Leu Glu Met Asn Gly Leu Lys Pro Glu Asp Thr Ala Ile Tyr Tyr Cys
                85                  90                  95

Ala Ala Ala Asp Ala Ile Gly Leu Ala Glu Tyr Trp Ser Thr Pro Thr
            100                 105                 110

Leu Ser Ala Ala Arg Tyr Lys Tyr Trp Gly Gln Gly Thr Gln Val Thr
        115                 120                 125

Val Ser Ser
    130

<210> SEQ ID NO 16
<211> LENGTH: 131
<212> TYPE: PRT
<213> ORGANISM: Artificial
<220> FEATURE:
<223> OTHER INFORMATION: Nb23

<400> SEQUENCE: 16

Gln Val Gln Leu Gln Glu Ser Gly Gly Gly Ser Val Gln Val Gly Gly
 1               5                  10                  15

Ser Leu Arg Val Ala Cys Ala Ala Ser Gly Asp Thr Phe Ser Gly Tyr
            20                  25                  30

Leu Ala Ala Trp Phe Arg Gln Ala Pro Gly Lys Gly Arg Glu Gly Val
        35                  40                  45
```

```
Ala Ala Ile Asn Ser Lys Arg His Thr Thr Ser Tyr Ala Asp Ser Val
        50                  55                  60

Lys Gly Arg Phe Thr Ile Ser Lys Asp Asn Ala Asp Asn Ile Met Tyr
 65                  70                  75                  80

Leu Glu Met Asn Ser Leu Lys Pro Glu Asp Thr Ala Ile Tyr Tyr Cys
                 85                  90                  95

Ala Ala Ala Asp Ala Ile Gly Leu Ala Glu Tyr Trp Ser Thr Pro Thr
            100                 105                 110

Leu Ser Ala Ala Arg Tyr Lys Tyr Trp Gly Gln Gly Thr Gln Val Thr
            115                 120                 125

Val Ser Ser
    130

<210> SEQ ID NO 17
<211> LENGTH: 131
<212> TYPE: PRT
<213> ORGANISM: Artificial
<220> FEATURE:
<223> OTHER INFORMATION: Nb75

<400> SEQUENCE: 17

Gln Val Gln Leu Gln Glu Ser Gly Gly Gly Ser Val Gln Ala Gly Gly
  1               5                  10                  15

Ser Leu Arg Leu Ser Cys Val Ala Ser Glu Tyr Pro Ser Ser Ser Thr
                 20                  25                  30

Ala Met Ala Trp Phe Arg Gln Ala Pro Gly Lys Glu Arg Glu Gly Val
             35                  40                  45

Ala Ala Ile Asn Ser Val Arg His Thr Thr Ser Tyr Ala Asp Ser Val
        50                  55                  60

Lys Gly Arg Phe Thr Ile Ser Lys Asp Asn Ala Asp Asn Met Met Tyr
 65                  70                  75                  80

Leu Glu Met Asn Ser Leu Lys Pro Glu Asp Thr Ala Ile Tyr Tyr Cys
                 85                  90                  95

Ala Ala Ala Asp Ala Ile Gly Leu Ala Glu Tyr Trp Ser Thr Pro Thr
            100                 105                 110

Leu Ser Ala Ala Arg Tyr Lys Tyr Trp Gly Gln Gly Thr Gln Val Thr
            115                 120                 125

Val Ser Ser
    130

<210> SEQ ID NO 18
<211> LENGTH: 131
<212> TYPE: PRT
<213> ORGANISM: Artificial
<220> FEATURE:
<223> OTHER INFORMATION: Nb71

<400> SEQUENCE: 18

Gln Val Gln Leu Gln Glu Ser Gly Gly Gly Ala Val Gln Pro Gly Gly
  1               5                  10                  15

Ser Leu Lys Leu Ser Cys Glu Ala Ser Gly Asp Val Pro Glu Asn Gly
                 20                  25                  30

Tyr Met Ala Trp Phe Arg Gln Ala Pro Gly Lys Glu Arg Glu Gly Val
             35                  40                  45

Ala Ala Ile Asn Ser Val Arg His Thr Thr Ser Tyr Ala Asp Ser Val
        50                  55                  60

Lys Gly Arg Phe Thr Ile Ser Lys Asp Asn Ala Asp Asn Met Met Tyr
 65                  70                  75                  80
```

```
Leu Glu Met Asn Ser Leu Lys Pro Glu Asp Thr Ala Ile Tyr Tyr Cys
                85                  90                  95

Ala Ala Ala Asp Ala Ile Gly Leu Ala Glu Tyr Trp Ser Thr Pro Thr
            100                 105                 110

Leu Ser Ala Ala Arg Tyr Lys Tyr Trp Gly Gln Gly Thr Gln Val Thr
        115                 120                 125

Val Ser Ser
    130

<210> SEQ ID NO 19
<211> LENGTH: 1000
<212> TYPE: PRT
<213> ORGANISM: Artificial
<220> FEATURE:
<223> OTHER INFORMATION: TRCPEG

<400> SEQUENCE: 19

Met Ser Glu Leu Ile Lys Glu Asn Met His Met Lys Leu Tyr Met Glu
1               5                   10                  15

Gly Thr Val Asn Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Met Tyr
    50                  55                  60

Gly Ser Arg Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Pro Ser
        115                 120                 125

Asn Gly Pro Val Met Gln Lys Lys Thr Leu Gly Trp Glu Ala Asn Thr
    130                 135                 140

Glu Met Leu Tyr Pro Ala Asp Gly Gly Leu Glu Gly Arg Ser Asp Met
145                 150                 155                 160

Ala Leu Lys Leu Val Gly Gly His Leu Ile Cys Asn Phe Lys Thr
                165                 170                 175

Thr Tyr Arg Ser Lys Lys Pro Ala Lys Asn Leu Lys Met Pro Gly Val
            180                 185                 190

Tyr Tyr Val Asp His Arg Leu Glu Arg Ile Lys Glu Ala Asp Lys Glu
        195                 200                 205

Thr Tyr Val Glu Gln His Glu Val Ala Val Ala Arg Tyr Cys Asp Leu
    210                 215                 220

Pro Ser Lys Leu Gly His Lys Leu Asn Gly Gly Ser Gly Gly Gly
225                 230                 235                 240

Gly Leu Ala Gly Arg Gly Val Ile Tyr Ile Pro Lys Asp Cys Gln Ala
            245                 250                 255

Asn Arg Tyr Leu Gly Thr Leu Asn Ile Arg Asp Met Ile Ser Asp Phe
        260                 265                 270

Lys Gly Val Gln Tyr Glu Lys Trp Ile Thr Ala Gly Leu Val Met Pro
    275                 280                 285

Thr Phe Lys Ile Val Ile Arg Leu Pro Ala Asn Ala Phe Thr Gly Leu
290                 295                 300
```

-continued

```
Thr Trp Val Met Ser Phe Asp Ala Tyr Asn Arg Ile Thr Ser Arg Ile
305                 310                 315                 320

Thr Ala Ser Ala Asp Pro Val Tyr Thr Leu Ser Val Pro His Trp Leu
            325                 330                 335

Ile His His Lys Leu Gly Thr Phe Ser Cys Glu Ile Asp Tyr Gly Glu
                340                 345                 350

Leu Cys Gly His Ala Met Trp Phe Lys Ser Thr Thr Phe Glu Ser Pro
                    355                 360                 365

Arg Leu His Phe Thr Cys Leu Thr Gly Asn Asn Lys Glu Leu Ala Ala
                370                 375                 380

Asp Trp Gln Ala Val Val Glu Leu Tyr Ala Glu Leu Glu Glu Ala Thr
385                 390                 395                 400

Ser Phe Leu Gly Lys Pro Thr Leu Val Phe Asp Pro Gly Val Phe Asn
                    405                 410                 415

Gly Lys Phe Gln Phe Leu Thr Cys Pro Pro Ile Phe Phe Asp Leu Thr
                420                 425                 430

Ala Val Thr Ala Leu Arg Ser Ala Gly Leu Thr Leu Gly Gln Val Pro
            435                 440                 445

Met Val Gly Thr Thr Lys Val Tyr Asn Leu Asn Ser Thr Leu Val Ser
450                 455                 460

Cys Val Leu Gly Met Gly Gly Thr Val Arg Gly Arg Val His Ile Cys
465                 470                 475                 480

Ala Pro Ile Phe Tyr Ser Ile Val Leu Trp Val Val Ser Glu Trp Asn
                    485                 490                 495

Gly Thr Thr Met Asp Trp Asn Glu Leu Phe Lys Tyr Pro Gly Val Tyr
                500                 505                 510

Val Glu Glu Asp Gly Ser Phe Glu Val Lys Ile Arg Ser Pro Tyr His
                515                 520                 525

Arg Thr Pro Ala Arg Leu Leu Ala Gly Gln Ser Gln Arg Asp Met Ser
530                 535                 540

Ser Leu Asn Phe Tyr Ala Ile Ala Gly Pro Ile Ala Pro Ser Gly Glu
545                 550                 555                 560

Thr Ala Gln Leu Pro Ile Val Val Gln Ile Asp Glu Ile Val Arg Pro
                565                 570                 575

Asp Leu Ser Leu Pro Ser Phe Glu Asp Asp Tyr Phe Val Trp Val Asp
            580                 585                 590

Phe Ser Glu Phe Thr Leu Asp Lys Glu Glu Ile Glu Ile Gly Ser Arg
    595                 600                 605

Phe Phe Asp Phe Thr Ser Asn Thr Cys Arg Val Ser Met Gly Glu Asn
    610                 615                 620

Pro Phe Ala Ala Met Ile Ala Cys His Gly Leu His Ser Gly Val Leu
625                 630                 635                 640

Asp Leu Lys Leu Gln Trp Ser Leu Asn Thr Glu Phe Gly Lys Ser Ser
                645                 650                 655

Gly Ser Val Thr Ile Thr Lys Leu Val Gly Asp Lys Ala Met Gly Leu
                660                 665                 670

Asp Gly Pro Ser His Val Phe Ala Ile Gln Lys Leu Glu Gly Thr Thr
                675                 680                 685

Glu Leu Leu Val Gly Asn Phe Ala Gly Ala Asn Pro Asn Thr Arg Phe
                690                 695                 700

Ser Leu Tyr Ser Arg Trp Met Ala Ile Lys Leu Asp Gln Ala Lys Ser
705                 710                 715                 720
```

```
Ile Lys Val Leu Arg Val Leu Cys Lys Pro Arg Pro Gly Phe Ser Phe
                725                 730                 735

Tyr Gly Arg Thr Ser Phe Pro Val Asp Pro Ala Phe Leu Tyr Lys Val
            740                 745                 750

Val Arg Ser Phe Gly Pro Ala Met Val Ser Lys Gly Glu Glu Leu Phe
        755                 760                 765

Thr Gly Val Val Pro Ile Leu Val Glu Leu Asp Gly Asp Val Asn Gly
    770                 775                 780

His Lys Phe Ser Val Ser Gly Glu Gly Glu Gly Asp Ala Thr Tyr Gly
785                 790                 795                 800

Lys Leu Thr Leu Lys Phe Ile Cys Thr Thr Gly Lys Leu Pro Val Pro
                805                 810                 815

Trp Pro Thr Leu Val Thr Thr Leu Thr Tyr Gly Val Gln Cys Phe Ser
            820                 825                 830

Arg Tyr Pro Asp His Met Lys Gln His Asp Phe Phe Lys Ser Ala Met
        835                 840                 845

Pro Glu Gly Tyr Val Gln Glu Arg Thr Ile Phe Phe Lys Asp Asp Gly
    850                 855                 860

Asn Tyr Lys Thr Arg Ala Glu Val Lys Phe Glu Gly Asp Thr Leu Val
865                 870                 875                 880

Asn Arg Ile Glu Leu Lys Gly Ile Asp Phe Lys Glu Asp Gly Asn Ile
                885                 890                 895

Leu Gly His Lys Leu Glu Tyr Asn Tyr Asn Ser His Asn Val Tyr Ile
            900                 905                 910

Met Ala Asp Lys Gln Lys Asn Gly Ile Lys Val Asn Phe Lys Ile Arg
        915                 920                 925

His Asn Ile Glu Asp Gly Ser Val Gln Leu Ala Asp His Tyr Gln Gln
    930                 935                 940

Asn Thr Pro Ile Gly Asp Gly Pro Val Leu Leu Pro Asp Asn His Tyr
945                 950                 955                 960

Leu Ser Thr Gln Ser Ala Leu Ser Lys Asp Pro Asn Glu Lys Arg Asp
                965                 970                 975

His Met Val Leu Leu Glu Phe Val Thr Ala Ala Gly Ile Thr Leu Gly
            980                 985                 990

Met Asp Glu Leu Tyr Lys Thr Ser
        995                 1000
```

<210> SEQ ID NO 20
<211> LENGTH: 385
<212> TYPE: PRT
<213> ORGANISM: Artificial
<220> FEATURE:
<223> OTHER INFORMATION: Nb23EGFP

<400> SEQUENCE: 20

```
Gln Val Gln Leu Gln Glu Ser Gly Gly Gly Ser Val Gln Val Gly Gly
1               5                   10                  15

Ser Leu Arg Val Ala Cys Ala Ala Ser Gly Asp Thr Phe Ser Gly Tyr
                20                  25                  30

Leu Ala Ala Trp Phe Arg Gln Ala Pro Gly Lys Gly Arg Glu Gly Val
            35                  40                  45

Ala Ala Ile Asn Ser Lys Arg His Thr Thr Ser Tyr Ala Asp Ser Val
        50                  55                  60

Lys Gly Arg Phe Thr Ile Ser Lys Asp Asn Ala Asp Asn Ile Met Tyr
65                  70                  75                  80
```

Leu Glu Met Asn Ser Leu Lys Pro Glu Asp Thr Ala Ile Tyr Tyr Cys
                85                  90                  95

Ala Ala Ala Asp Ala Ile Gly Leu Ala Glu Tyr Trp Ser Thr Pro Thr
            100                 105                 110

Leu Ser Ala Ala Arg Tyr Lys Tyr Trp Gly Gln Gly Thr Gln Val Thr
        115                 120                 125

Val Ser Ser Gly Gly Gly Ser Gly Gly Gly Met Val Ser Lys Gly Glu
    130                 135                 140

Glu Leu Phe Thr Gly Val Val Pro Ile Leu Val Glu Leu Asp Gly Asp
145                 150                 155                 160

Val Asn Gly His Lys Phe Ser Val Ser Gly Glu Gly Glu Gly Asp Ala
            165                 170                 175

Thr Tyr Gly Lys Leu Thr Leu Lys Phe Ile Cys Thr Thr Gly Lys Leu
        180                 185                 190

Pro Val Pro Trp Pro Thr Leu Val Thr Thr Leu Thr Tyr Gly Val Gln
            195                 200                 205

Cys Phe Ser Arg Tyr Pro Asp His Met Lys Gln His Asp Phe Phe Lys
210                 215                 220

Ser Ala Met Pro Glu Gly Tyr Val Gln Glu Arg Thr Ile Phe Phe Lys
225                 230                 235                 240

Asp Asp Gly Asn Tyr Lys Thr Arg Ala Glu Val Lys Phe Glu Gly Asp
            245                 250                 255

Thr Leu Val Asn Arg Ile Glu Leu Lys Gly Ile Asp Phe Lys Glu Asp
        260                 265                 270

Gly Asn Ile Leu Gly His Lys Leu Glu Tyr Asn Tyr Asn Ser His Asn
            275                 280                 285

Val Tyr Ile Met Ala Asp Lys Gln Lys Asn Gly Ile Lys Val Asn Phe
290                 295                 300

Lys Ile Arg His Asn Ile Glu Asp Gly Ser Val Gln Leu Ala Asp His
305                 310                 315                 320

Tyr Gln Gln Asn Thr Pro Ile Gly Asp Gly Pro Val Leu Leu Pro Asp
            325                 330                 335

Asn His Tyr Leu Ser Thr Gln Ser Ala Leu Ser Lys Asp Pro Asn Glu
        340                 345                 350

Lys Arg Asp His Met Val Leu Leu Glu Phe Val Thr Ala Ala Gly Ile
            355                 360                 365

Thr Leu Gly Met Asp Glu Leu Tyr Lys Thr Ser His His His His His
        370                 375                 380

His
385

<210> SEQ ID NO 21
<211> LENGTH: 686
<212> TYPE: PRT
<213> ORGANISM: Artificial
<220> FEATURE:
<223> OTHER INFORMATION: Nb23ALP

<400> SEQUENCE: 21

Gln Val Gln Leu Gln Glu Ser Gly Gly Gly Ser Val Gln Val Gly Gly
1               5                   10                  15

Ser Leu Arg Val Ala Cys Ala Ala Ser Gly Asp Thr Phe Ser Gly Tyr
            20                  25                  30

Leu Ala Ala Trp Phe Arg Gln Ala Pro Gly Lys Gly Arg Glu Gly Val
        35                  40                  45

```
Ala Ala Ile Asn Ser Lys Arg His Thr Thr Ser Tyr Ala Asp Ser Val
 50                  55                  60

Lys Gly Arg Phe Thr Ile Ser Lys Asp Asn Ala Asp Asn Ile Met Tyr
 65                  70                  75                  80

Leu Glu Met Asn Ser Leu Lys Pro Glu Asp Thr Ala Ile Tyr Tyr Cys
                 85                  90                  95

Ala Ala Ala Asp Ala Ile Gly Leu Ala Glu Tyr Trp Ser Thr Pro Thr
                100                 105                 110

Leu Ser Ala Ala Arg Tyr Lys Tyr Trp Gly Gln Gly Thr Gln Val Thr
                115                 120                 125

Val Ser Ser Gly Gly Gly Ser Gly Gly Gly Val Lys Gln Ser Thr Ile
130                 135                 140

Ala Leu Ala Leu Leu Pro Leu Leu Phe Thr Pro Val Thr Lys Ala Arg
145                 150                 155                 160

Thr Pro Glu Met Pro Leu Gln Thr Gln Ala Thr Ser Arg Glu Glu Pro
                165                 170                 175

Pro Arg Leu Pro Ser Lys His Arg Pro Gly Val Lys Thr Gln Ala Thr
                180                 185                 190

Ser Arg Glu Glu Pro Pro Arg Leu Pro Ser Lys His Arg Pro Gly Val
                195                 200                 205

Lys Thr Gln Ala Thr Ser Arg Glu Glu Pro Pro Arg Leu Pro Ser Lys
210                 215                 220

His Arg Pro Gly Val Lys Thr Gln Ala Thr Ser Arg Glu Glu Pro Pro
225                 230                 235                 240

Arg Leu Pro Ser Lys His Arg Pro Gly Val Lys Thr Gln Ala Thr Ser
                245                 250                 255

Leu Glu Val Leu Glu Asn Arg Ala Ala Gln Gly Asp Ile Thr Ala Pro
                260                 265                 270

Gly Gly Ala Arg Arg Leu Thr Gly Asp Gln Thr Ala Ala Leu Arg Asp
                275                 280                 285

Ser Leu Ser Asp Lys Pro Ala Lys Asn Ile Ile Leu Leu Ile Gly Asp
                290                 295                 300

Gly Met Gly Asp Ser Glu Ile Thr Ala Ala Arg Asn Tyr Ala Glu Gly
305                 310                 315                 320

Ala Gly Gly Phe Phe Lys Gly Ile Asp Ala Leu Pro Leu Thr Gly Gln
                325                 330                 335

Tyr Thr His Tyr Ala Leu Asn Lys Lys Thr Gly Lys Pro Asp Tyr Val
                340                 345                 350

Thr Asp Ser Ala Ala Ser Ala Thr Ala Trp Ser Thr Gly Val Lys Thr
                355                 360                 365

Tyr Asn Gly Ala Leu Gly Val Asp Ile His Glu Lys Asp His Pro Thr
                370                 375                 380

Ile Leu Glu Met Ala Lys Ala Ala Gly Leu Ala Thr Gly Asn Val Ser
385                 390                 395                 400

Thr Ala Glu Leu Gln Asp Ala Thr Pro Ala Ala Leu Val Ala His Val
                405                 410                 415

Thr Ser Arg Lys Cys Tyr Gly Pro Ser Ala Thr Ser Glu Lys Cys Pro
                420                 425                 430

Gly Asn Ala Leu Glu Lys Gly Gly Lys Gly Ser Ile Thr Glu Gln Leu
                435                 440                 445

Leu Asn Ala Arg Ala Asp Val Thr Leu Gly Gly Gly Ala Lys Thr Phe
450                 455                 460

Ala Glu Thr Ala Thr Ala Gly Glu Trp Gln Gly Lys Thr Leu Arg Glu
```

-continued

```
            465                 470                 475                 480
    Gln Ala Gln Ala Arg Gly Tyr Gln Leu Val Ser Asp Ala Ala Ser Leu
                        485                 490                 495

Asn Ser Val Thr Glu Ala Asn Gln Gln Lys Pro Leu Leu Gly Leu Phe
                        500                 505                 510

Ala Asp Gly Asn Met Pro Val Arg Trp Leu Gly Pro Lys Ala Thr Tyr
                        515                 520                 525

His Gly Asn Ile Asp Lys Pro Ala Val Thr Cys Thr Pro Asn Pro Gln
                        530                 535                 540

Arg Asn Asp Ser Val Pro Thr Leu Ala Gln Met Thr Asp Lys Ala Ile
    545                 550                 555                 560

Glu Leu Leu Ser Lys Asn Glu Lys Gly Phe Phe Leu Gln Val Glu Gly
                        565                 570                 575

Ala Ser Ile Asp Lys Gln Asp His Ala Ala Asn Pro Cys Gly Gln Ile
                        580                 585                 590

Gly Glu Thr Val Asp Leu Asp Glu Ala Val Gln Arg Ala Leu Glu Phe
                        595                 600                 605

Ala Lys Lys Glu Gly Asn Thr Leu Val Ile Val Thr Ala Asp His Ala
        610                 615                 620

His Ala Ser Gln Ile Val Ala Pro Asp Thr Lys Ala Pro Gly Leu Thr
    625                 630                 635                 640

Gln Ala Leu Asn Thr Lys Asp Gly Ala Val Met Val Met Ser Tyr Gly
                        645                 650                 655

Asn Ser Glu Glu Asp Ser Gln Glu His Thr Gly Ser Gln Leu Arg Ile
                        660                 665                 670

Ala Ala Tyr Gly Pro His Ala Ala His His His His His
                        675                 680                 685
```